United States Patent
Lee et al.

(10) Patent No.: US 10,370,588 B2
(45) Date of Patent: Aug. 6, 2019

(54) ORGANOMETALLIC COMPOUND AND ORGANIC LIGHT-EMITTING DEVICE INCLUDING THE SAME

(71) Applicant: Samsung Electronics Co., Ltd., Suwon-si, Gyeonggi-do (KR)

(72) Inventors: Jungin Lee, Seoul (KR); Yoonhyun Kwak, Seoul (KR); Sunyoung Lee, Seoul (KR); Ohyun Kwon, Yongin-si (KR); Seungyeon Kwak, Yongin-si (KR); Jiyoun Lee, Incheon (KR); Seokhwan Hong, Seoul (KR); Aram Jeon, Suwon-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 414 days.

(21) Appl. No.: 14/859,895

(22) Filed: Sep. 21, 2015

(65) Prior Publication Data
US 2016/0190484 A1    Jun. 30, 2016

(30) Foreign Application Priority Data
Dec. 30, 2014    (KR) .................. 10-2014-0194325

(51) Int. Cl.
| H01L 51/00 | (2006.01) |
| C09K 11/06 | (2006.01) |
| C07F 15/00 | (2006.01) |
| H01L 51/50 | (2006.01) |

(52) U.S. Cl.
CPC .......... *C09K 11/06* (2013.01); *C07F 15/0033* (2013.01); *C07F 15/0086* (2013.01); *H01L 51/0081* (2013.01); *H01L 51/0085* (2013.01); C09K 2211/1007 (2013.01); C09K 2211/1029 (2013.01); C09K 2211/1096 (2013.01); C09K 2211/185 (2013.01); H01L 51/5016 (2013.01)

(58) Field of Classification Search
CPC .. C07F 15/0033; C07F 15/0086; C09K 11/06; C09K 2211/1007; C09K 2211/1029; C09K 2211/1096; C09K 2211/185; H01L 51/0094; H01L 51/5012
See application file for complete search history.

(56) References Cited

U.S. PATENT DOCUMENTS 7,563,898 B2    7/2009 Seo et al.
2015/0090974 A1*  4/2015 Kim ................ C09K 11/06
                                                    257/40

FOREIGN PATENT DOCUMENTS

| KR | 1020130110934 A | 10/2013 | |
| KR | 101344787 B1 * | 12/2013 | ............ C09K 11/06 |
| WO | 2008078800 A1 | 7/2008 | |
| WO | 2013107487 A1 | 7/2013 | |

* cited by examiner

*Primary Examiner* — Jennifer A Chriss
*Assistant Examiner* — Sean M DeGuire
(74) *Attorney, Agent, or Firm* — Cantor Colburn LLP

(57) ABSTRACT

An organometallic compound represented by Formula 1:

$$M(L_1)_{n1}(L_2)_{n2} \quad \text{Formula 1}$$

wherein in Formula 1, M, $L_1$, $L_2$, n1, and n2 are the same as described in the specification.

4 Claims, 1 Drawing Sheet

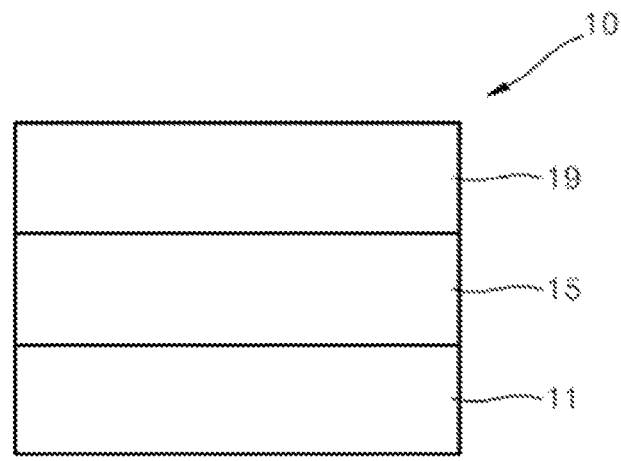

ORGANOMETALLIC COMPOUND AND ORGANIC LIGHT-EMITTING DEVICE INCLUDING THE SAME

CROSS-REFERENCE TO RELATED APPLICATION

This application claims the benefit of Korean Patent Application No. 10-2014-0194325, filed on Dec. 30, 2014, in the Korean Intellectual Property Office, the disclosure of which is incorporated herein in its entirety by reference.

BACKGROUND

1. Field

One or more exemplary embodiments relate an organometallic compound and an organic light-emitting device including the same.

2. Description of the Related Art

Organic light-emitting devices are self-emission devices that have wide viewing angles, high contrast ratios, and short response times. OLEDs also exhibit excellent brightness, driving voltage, and response speed characteristics, and produce multicolored images.

A typical organic light-emitting device may include an anode, a cathode, and an organic layer, wherein the organic layer is disposed between the anode and the cathode and includes an emission layer. The organic light-emitting device may also include a hole transport region between the anode and the emission layer, and an electron transport region between the emission layer and the cathode. Holes provided from the anode may move toward the emission layer through the hole transport region, and electrons provided from the cathode may move toward the emission layer through the electron transport region. Such holes and electrons may be recombined in the emission layer to produce excitons. These excitons may change from an excited state to a ground state, thereby generating light.

Various types of organic light emitting devices are known. However, there still remains a need in OLEDs having low driving voltage, high efficiency, high brightness, and long lifespan.

SUMMARY

One or more exemplary embodiments include a novel organometallic compound and an organic light-emitting device including the same.

Additional aspects will be set forth in part in the description which follows and, in part, will be apparent from the description, or may be learned by practice of the presented embodiments.

According to one or more exemplary embodiments, there is provided an organometallic compound represented by Formula 1:

Formula 1

$M(L_1)_{n1}(L_2)_{n2}$

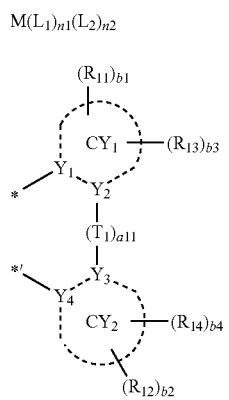

Formula 2A

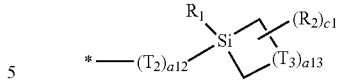

Formula 2B

In Formula 1, M may be selected from Ir, Pt, Os, Ti, Zr, Hf, Eu, Tb, Tm, and Rh;

$L_1$ may be selected from ligands represented by Formula 2A, and n1 may be 1, 2, or 3, wherein when n1 is 2 or more, 2 or more groups $L_1$ may be identical to or different from each other; and $L_2$ may be selected from a monovalent organic ligand, a divalent organic ligand, a trivalent organic ligand, and a tetravalent organic ligand, and n2 may be 0, 1, 2, 3 or 4, wherein when n2 is 2 or more, 2 or more groups $L_2$ may be identical to or different from each other.

In Formula 1, $L_1$ and $L_2$ may be different from each other.

In Formula 2A, $Y_1$ to $Y_4$ may be each independently C or N, $Y_1$ and $Y_2$ may be connected to each other via a single bond or a double bond, and $Y_3$ and $Y_4$ may be connected to each other via a single bond or a double bond; and $CY_1$ and $CY_2$ may be each independently selected from a $C_5$-$C_{60}$ carbocyclic group and a $C_1$-$C_{60}$ heterocyclic group, and may be optionally connected to each other via a first linking group.

In Formula 2A, $T_1$ may be a substituted or unsubstituted $C_1$-$C_3$ alkylene group.

In Formula 2B, $T_2$ may be selected from a substituted or unsubstituted $C_1$-$C_{10}$ alkylene group, a substituted or unsubstituted $C_2$-$C_{10}$ alkenylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted monovalent non-aromatic condensed polycyclic group, and a substituted or unsubstituted monovalent non-aromatic condensed heteropolycyclic group; and $T_3$ may be selected from —O—, —S—, a substituted or unsubstituted $C_1$-$C_7$ alkylene group, and a substituted or unsubstituted $C_2$-$C_7$ alkenylene group.

In Formulae 2A and 2B, a11 to a13 may be each independently an integer selected from 0 to 3; and $R_1$, $R_2$, $R_{11}$, and $R_{12}$ may be each independently selected from a hydrogen, a deuterium, —F, —Cl, —Br, —I, —SF$_5$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N(Q$_1$)(Q$_2$), —Si(Q$_3$)(Q$_4$)(Q$_5$), —B(Q$_6$)(Q$_7$), and —P(=O)(Q$_8$)(Q$_9$).

In Formula 2A, b1 and b2 may be each independently an integer selected from 0 to 4, and in Formula 2B, c1 may be an integer selected from 0 to 16.

In Formula 2A, R$_{13}$ and R$_{14}$ may be each independently a group represented by Formula 2B;

b3 and b4 may be each independently an integer selected from 0 to 4, wherein a sum of b3 and b4 (b3+b4) may be 1 or more;

* and *' each indicates a binding site to M of Formula 1; and at least one of substituents of the substituted C$_1$-C$_{10}$ alkylene group, the substituted C$_2$-C$_{10}$ alkenylene group, the substituted C$_3$-C$_{10}$ cycloalkylene group, the substituted C$_1$-C$_{10}$ heterocycloalkylene group, the substituted C$_3$-C$_{10}$ cycloalkenylene group, the substituted C$_1$-C$_{10}$ heterocycloalkenylene group, the substituted C$_6$-C$_{60}$ arylene group, the substituted C$_1$-C$_{60}$ heteroarylene group, the substituted monovalent non-aromatic condensed polycyclic group, the substituted monovalent non-aromatic condensed heteropolycyclic group, the substituted C$_1$-C$_{60}$ alkyl group, the substituted C$_2$-C$_{60}$ alkenyl group, the substituted C$_2$-C$_{60}$ alkynyl group, the substituted C$_1$-C$_{60}$ alkoxy group, the substituted C$_3$-C$_{10}$ cycloalkyl group, the substituted C$_1$-C$_{10}$ heterocycloalkyl group, the substituted C$_3$-C$_{10}$ cycloalkenyl group, the substituted C$_1$-C$_{10}$ heterocycloalkenyl group, the substituted C$_6$-C$_{60}$ aryl group, the substituted C$_6$-C$_{60}$ aryloxy group, the substituted C$_6$-C$_{60}$ arylthio group, the substituted C$_1$-C$_{60}$ heteroaryl group, the substituted monovalent non-aromatic condensed polycyclic group, and the substituted monovalent non-aromatic condensed heteropolycyclic group may be selected from:

a deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{60}$ alkyl group, a C$_2$-C$_{60}$ alkenyl group, a C$_2$-C$_{60}$ alkynyl group, and a C$_1$-C$_{60}$ alkoxy group;

a C$_1$-C$_{60}$ alkyl group, a C$_2$-C$_{60}$ alkenyl group, a C$_2$-C$_{60}$ alkynyl group, and a C$_1$-C$_{60}$ alkoxy group, each substituted with at least one of a deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, a monovalent non-aromatic condensed heteropolycyclic group, —N(Q$_{11}$)(Q$_{12}$), —Si(Q$_{13}$)(Q$_{14}$)(Q$_{15}$), —B(Q$_{16}$)(Q$_{17}$), and —P(=O)(Q$_{18}$)(Q$_{19}$);

a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, and a monovalent non-aromatic condensed heteropolycyclic group;

a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, and a monovalent non-aromatic condensed heteropolycyclic group, each substituted with at least one of a deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, a monovalent non-aromatic condensed heteropolycyclic group, —N(Q$_{21}$)(Q$_{22}$), —Si(Q$_{23}$)(Q$_{24}$)(Q$_{25}$), —B(Q$_{26}$)(Q$_{27}$), and —P(=O)(Q$_{28}$)(Q$_{29}$); and —N(Q$_{31}$)(Q$_{32}$), —Si(Q$_{33}$)(Q$_{34}$)(Q$_{35}$), —B(Q$_{36}$)(Q$_{37}$), and —P(=O)(Q$_{38}$)(Q$_{39}$), wherein Q$_1$ to Q$_9$, Q$_{11}$ to Q$_{19}$, Q$_{21}$ to Q$_{29}$, and Q$_{31}$ to Q$_{39}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted C$_1$-C$_{60}$ alkyl group, a substituted or unsubstituted C$_2$-C$_{60}$ alkenyl group, a substituted or unsubstituted C$_2$-C$_{60}$ alkynyl group, a substituted or unsubstituted C$_1$-C$_{60}$ alkoxy group, a substituted or unsubstituted C$_3$-C$_{10}$ cycloalkyl group, a substituted or unsubstituted C$_1$-C$_{10}$ heterocycloalkyl group, a substituted or unsubstituted C$_3$-C$_{10}$ cycloalkenyl group, a substituted or unsubstituted C$_1$-C$_{10}$ heterocycloalkenyl group, a substituted or unsubstituted C$_6$-C$_{60}$ aryl group, a substituted or unsubstituted C$_6$-C$_{60}$ aryloxy group, a substituted or unsubstituted C$_6$-C$_{60}$ arylthio group, a substituted or unsubstituted C$_1$-C$_{60}$ heteroaryl group, a substituted or unsubstituted monovalent non-aromatic condensed polycyclic group, and a substituted or unsubstituted monovalent non-aromatic condensed heteropolycyclic group.

According to one or more exemplary embodiments, there is provided an organic light-emitting device including a first electrode; a second electrode; and an organic layer disposed between the first electrode and the second electrode, wherein the organic layer includes an emission layer and at least one of the organometallic compounds of Formula 1.

The organometallic compound may be included in the emission layer.

The organometallic compound included in the emission layer may serve as a dopant, and the emission layer may further include a host.

BRIEF DESCRIPTION OF THE DRAWINGS

These and/or other aspects will become apparent and more readily appreciated from the following description of the exemplary embodiments, taken in conjunction with the accompanying drawings in which:

The FIGURE illustrates a schematic view of an organic light-emitting according to an embodiment.

DETAILED DESCRIPTION

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the FIGURES, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

There is provided an organometallic compound represented by Formula 1 below:

$$M(L_1)_{n1}(L_2)_{n2} \qquad \text{Formula 1}$$

In Formula 1, M may be selected from iridium (Ir), platinum (Pt), osmium (Os), titanium (Ti), zirconium (Zr), hafnium (Hf), europium (Eu), terbium (Tb), thulium (Tm), and rhodium (Rh).

For example, M in Formula 1 may be selected from Ir, Pt, Os, and Rh.

In an exemplary embodiment, M in Formula 1 may be selected from Ir and Pt, but the embodiment is not limited thereto.

In Formula 1, $L_1$ may be a ligand represented by Formula 2A below, and n1 may be 1, 2, or 3, wherein when n1 is 2 or more, 2 or more groups $L_1$ may be identical to or different from each other:

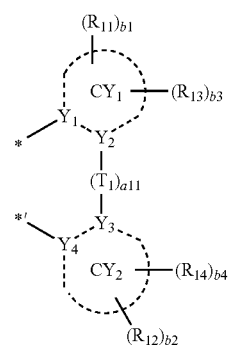

Formula 2A

In Formula 2A, $R_{13}$ and $R_{14}$ may be each independently a group represented by Formula 2B below:

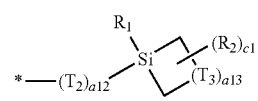

Formula 2B

Formulae 2A and 2B may be understood by referring to the descriptions provided below.

In Formula 1, $L_2$ may be selected from a monovalent organic ligand, a divalent organic ligand, a trivalent organic ligand, and a tetravalent organic ligand, and n2 may be 0, 1, 2, 3 or 4, wherein n2 is 2 or more, 2 or more groups $L_2$ may be identical to or different from each other.

In Formula 1, $L_1$ and $L_2$ may be different from each other.

For example, n1 in Formula 1 may be 1.

In some exemplary embodiments, the organometallic compound of Formula 1 may be neutral (i.e., may not comprise an ionic group), may not be a form of a base consisting of a pair or ions.

In an exemplary embodiment, in Formula 1, M may be Ir and a sum of n1 and n2 (n1+n2) may be 3; or M may be Pt and a sum of n1 and n2 (n1+n2) may be 2. Here, the organometallic compound of Formula 1 may be neutral (i.e., may not be in a form of a base consisting of a pair or ions).

In Formula 2A, $Y_1$ to $Y_4$ may be each independently carbon (C) or nitrogen (N), $Y_1$ and $Y_2$ may be connected to each other via a single bond or a double bond, and $Y_3$ and $Y_4$ may be connected to each other via a single bond or a double bond.

For example, in Formula 2A, $Y_1$ may be N and $Y_2$ to $Y_4$ may be C.

In Formula 2A, $CY_1$ and $CY_2$ may be each independently selected from a $C_5$-$C_{60}$ carbocyclic group, and a $C_1$-$C_{60}$ heterocyclic group, and may be optionally connected to each other via a first linking group. Here, the $C_5$-$C_{60}$ carbocyclic group and the $C_1$-$C_{60}$ heterocyclic group may be "a monocyclic group" or "a polycyclic group".

In an exemplary embodiment, in Formula 2A, $CY_1$ and $CY_2$ may be each independently selected from a benzene, a naphthalene, a fluorene, a spiro-fluorene, an indene, a pyrrole, a thiophene, a furan, an imidazole, a pyrazole, a thiazole, an isothiazole, an oxazole, an isooxazole, a pyridine, a pyrazine, a pyrimidine, a pyridazine, a quinoline, an isoquinoline, a benzoquinoline, a quinoxaline, a quinazoline, a carbazole, a benzoimidazole, a benzofuran, a benzothiophene, an isobenzothiophene, a benzooxazole, an isobenzooxazole, a triazole, a tetrazole, an oxadiazole, a triazine, a dibenzofuran, a dibenzothiophene, and 5,6,7,8-tetrahydroisoquinoline.

In some exemplary embodiments, in Formula 2A, $CY_1$ may be selected from a pyridine, a pyrimidine, a pyrazine, a triazine, a quinoline, an isoquinoline, a quinazoline, a quinoxaline, a triazole, an imidazole, a pyrazole, and 5,6,7,8-tetrahydroisoquinoline; and $CY_2$ may be selected from a benzene, a naphthalene, a pyridine, a pyrimidine, a pyrazine, a triazine, a quinoline, an isoquinoline, a quinazoline, a quinoxaline, a fluorene, a carbazole, a dibenzofuran, and a dibenzothiophene.

In an exemplary embodiment, in Formula 2A, $CY_1$ may be a pyridine and $CY_2$ may be selected from a benzene, a fluorene, a carbazole, a dibenzofuran, and a dibenzothiophene.

In some exemplary embodiments, in Formula 2A, $CY_1$ may be a pyridine and $CY_2$ may be a benzene.

In Formula 2A, $CY_1$ and $CY_2$ may be further connected to each other via a first linking group, wherein the first linking group is represented by Formula 6 below:

$$*-(Z_{31})_{b10}-*' \qquad \text{Formula 6}$$

In Formula 6, $Z_{31}$ may be selected from $*-O-*'$, $*-S-*'$, $*-N(Q_{41})-*'$, $*-C(Q_{42})(Q_{43})-*'$, $*-C(Q_{44})=C(Q_{45})-*'$, and

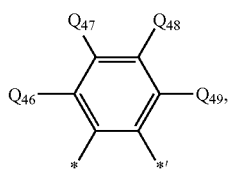

wherein $Q_{41}$ to $Q_{49}$ may be each independently selected from:

a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group; a $C_1$-$C_{20}$ alkyl group and a $C_1$-$C_{20}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a pyridinyl group, and a pyrimidinyl group; and a phenyl group, a naphthyl group, a pyridinyl group, and a pyrimidinyl group; and b10 may be an integer selected from 1 to 10, wherein when b10 is 2 or more, 2 or more groups $Z_{31}$ may be identical to or different from each other.

For example, in Formula 6, $Q_{41}$ to $Q_{49}$ may be each independently selected from:

a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group; a $C_1$-$C_{20}$ alkyl group and a $C_1$-$C_{20}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a pyridinyl group, and a pyrimidinyl group; and a phenyl group, a naphthyl group, a pyridinyl group, and a pyrimidinyl group, but they are not limited thereto.

For example, in Formula 2, $CY_1$ and $CY_2$ may be connected to each other via a single bond or a first linking group, wherein the first linking group may be represented by $*-C(Q_{44})=C(Q_{45})-*'$ or

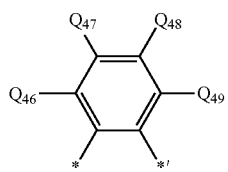

(wherein in Formula 6, b10 is 1), and wherein $Q_{44}$ to $Q_{49}$ may be each independently selected from a hydrogen, a $C_1$-$C_{10}$ alkyl group, and a $C_1$-$C_{10}$ alkoxy group, but they are not limited thereto.

In an exemplary embodiment, in Formula 2A, $Y_1$ may be N, $Y_2$ to $Y_4$ may be C, $CY_1$ may be selected from a pyridine, a pyrimidine, a pyrazine, a triazine, a triazole, an imidazole, and a pyrazole, and $CY_2$ may be selected from a benzene, a naphthalene, a pyridine, a pyrimidine, a pyrazine, a fluorene, a carbazole, a dibenzofuran, and a dibenzothiophene.

In Formula 2A, $T_1$ may be selected from a substituted or unsubstituted $C_1$-$C_3$ alkylene group.

In Formula 2B, $T_2$ may be selected from a substituted or unsubstituted $C_1$-$C_{10}$ alkylene group, a substituted or unsubstituted $C_2$-$C_{10}$ alkenylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted monovalent non-aromatic condensed polycyclic group, and a substituted or unsubstituted monovalent non-aromatic condensed heteropolycyclic group.

In Formula 2B, $T_3$ may be selected from —O—, —S—, a substituted or unsubstituted $C_1$-$C_7$ alkylene group, and a substituted or unsubstituted $C_2$-$C_7$ alkenylene group.

In an exemplary embodiment, in Formulae 2A and 2B, a11 denotes the number of $T_1$, and may be an integer selected from 0 to 3. When a11 is 0, -$(T_1)_{a11}$- may be a single bond. When a11 is 2 or more, 2 or more groups $T_1$ may be identical to or different from each other. When a12 is 0, -$(T_2)_{a12}$- may be a single bond. When a12 is 2 or more, 2 or more groups $T_2$ may be identical to or different from each other. When a13 is 0, -$(T_3)_{a13}$- may be a single bond. When a13 is 2 or more, 2 or more groups $T_3$ may be identical to or different from each other.

For example, in Formulae 2A and 2B, a11 to a13 may be 0, 1, or 2. For example, in Formulae 2A and 2B, a11 to a13 may be 0 or 1.

In an exemplary embodiment, $T_1$ in Formula 2A may be selected from:

a methylene group and an ethylene group; and a methylene group and an ethylene group, each substituted with at least one of a deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, and a naphthyl group;

$T_2$ in Formula 2B may be selected from:

a $C_1$-$C_5$ alkylene group, a cyclopentylene group, a cyclohexylene group, a cycloheptylene group, a cyclooctylene group, a cyclopentenylene group, a cyclohexenylene group, a cycloheptenylene group, a phenylene group, a naphthylene group, a fluorenylene group, a phenanthrenylene group, an anthracenylene group, a fluoranthenylene group, a triphenylenylene group, a pyrenylene group, a chrysenylene group, a pyrrolylene group, a thiophenylene group, a furanylene group, an imidazolylene group, a pyrazolylene group, a thiazolylene group, an isothiazolylene group, an oxazolylene group, an isooxazolylene group, a pyridinylene group, a pyrazinylene group, a pyrimidinylene group, a pyridazinylene group, an isoindolylene group, an indolylene group, an indazolyl group, a purinylene group, a quinolinylene group, an isoquinolinylene group, a benzoquinolinylene group, a quinoxalinylene group, a quinazolinylene group, a cinnolinylene group, a carbazolylene group, a phenanthrolinylene group, a benzoimidazolylene group, a benzofuranylene group, a benzothiophenylene group, an isobenzothiazolylene group, a benzooxazolylene group, an isobenzooxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, an imidazopyridinylene group, and an imidazopyrimidinylene group; and a $C_1$-$C_5$ alkylene group, a cyclopentylene group, a cyclohexylene group, a cycloheptylene group, a cyclooctylene group, a cyclopentenylene group, a cyclohexenylene group, a cycloheptenylene group, a phenylene group, a naphthylene group, a fluorenylene group, a phenanthrenylene group, an anthracenylene group, a fluoranthenylene group, a triphenylenylene group, a pyrenylene group, a chrysenylene group, a pyrrolylene group, a thiophenylene group, a furanylene group, an imidazolylene group, a pyrazolylene group, a thiazolylene group, an isothiazolylene group, an oxazolylene group, an isooxazolylene group, a pyridinylene group, a pyrazinylene group, a pyrimidinylene group, a pyridazinylene group, an isoindolylene group, an indolylene group, an indazolyl group, a purinylene group, a quinolinylene group, an isoquinolinylene group, a benzoquinolinylene group, a quinoxalinylene group, a quinazolinylene group, a cinnolinylene group, a carbazolylene group, a phenanthrolinylene group, a benzoimidazolylene group, a benzofuranylene group, a benzothiophenylene group, an isobenzothiazolylene group, a benzooxazolylene group, an isobenzooxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, an imidazopyridinylene group, and an imidazopyrimidinylene group, each substituted with at least one of a deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclooctyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and a11 and a12 in Formulae 2A and 2B may be each independently 0, 1, or 2.

In some exemplary embodiments, $T_1$ in Formula 2A may be selected from:

a methylene group; and a methylene group substituted with at least one of a deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, and a naphthyl group;

$T_2$ in Formula 2B may be selected from a $C_1$-$C_5$ alkylene group, a cyclopentylene group, a cyclohexylene group, a cycloheptylene group, a cyclooctylene group, a cyclopentenylene group, a cyclohexenylene group, a cycloheptenylene group, a phenylene group, a naphthylene group, a fluorenylene group, a phenanthrenylene group, a triphenylenylene group, a pyrenylene group, a chrysenylene group, a pyridinylene group, a pyrimidinylene group, a carbazolylene group, a triazinylene group, a dibenzofuranylene group, and a dibenzothiophenylene group; and a $C_1$-$C_5$ alkylene group, a cyclopentylene group, a cyclohexylene group, a cycloheptylene group, a cyclooctylene group, a cyclopentenylene group, a cyclohexenylene group, a cycloheptenylene group, a phenylene group, a naphthylene group, a fluorenylene group, a phenanthrenylene group, a triphenylenylene group, a pyrenylene group, a chrysenylene group, a pyridinylene group, a pyrimidinylene group, a carbazolylene group, a triazinylene group, a dibenzofuranylene group, and a dibenzothiophenylene group, each substituted with at least one of a deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, and a naphthyl group; and a11 and a12 in Formulae 2A and 2B may be each independently 0 or 1.

In some other exemplary embodiments, a11 and a12 in Formulae 2A and 2B may be all 0, but they are not limited thereto.

$T_3$ in Formula 2B may be selected from a substituted or unsubstituted $C_1$-$C_4$ alkylene group, and a13 in Formula 2B may be 0 or 1.

In Formulae 2A and 2B, $R_1$, $R_2$, $R_{11}$, and $R_{12}$ may be each independently selected from a hydrogen, a deuterium, —F, —Cl, —Br, —I, —$SF_5$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$N(Q_1)(Q_2)$, —$Si(Q_3)(Q_4)(Q_5)$, —$B(Q_6)(Q_7)$, and —$P(=O)(Q_8)(Q_9)$.

For example, in Formulae 2A and 2B, $R_1$, $R_2$, $R_{11}$, and $R_{12}$ may be each independently selected from:

a hydrogen, a deuterium, —F, —Cl, —Br, —I, —$SF_5$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one of a deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{14}$ aryl group, a $C_1$-$C_{14}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{14}$ aryl group, a $C_1$-$C_{14}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{14}$ aryl group, a $C_1$-$C_{14}$ heteroaryl group, a monovalent non-aromatic condensed polycyclic group, and a monovalent non-aromatic condensed heteropolycyclic group, each substituted with at least one of a deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{14}$ aryl group, a $C_1$-$C_{14}$ heteroaryl group, a monovalent non-aromatic condensed polycyclic group, and a monovalent non-aromatic condensed heteropolycyclic group; and —$N(Q_1)(Q_2)$, —$Si(Q_3)(Q_4)(Q_5)$, —$B(Q_6)(Q_7)$, and —$P(=O)(Q_8)(Q_9)$, wherein $Q_1$ to $Q_9$ may be each independently selected from a substituted or unsubstituted $C_1$-$C_{20}$ alkyl group, a substituted or unsubstituted $C_1$-$C_{20}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{14}$ aryl group, a substituted or unsubstituted $C_1$-$C_{14}$ heteroaryl group, a substituted or unsubstituted monovalent non-aromatic condensed polycyclic group, and a substituted or unsubstituted monovalent non-aromatic condensed heteropolycyclic group.

In some exemplary embodiments, in Formulae 2A and 2B, $R_1$, $R_2$, $R_{11}$, and $R_{12}$ may be each independently selected from:

a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —$SF_5$, $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one of a deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a cyclopentyl group, a cyclohexyl group, a cycloheptyl group, a cyclooctyl group, an adamantanyl group, a norbornanyl group, a cyclopentenyl group, a cyclohexenyl group, a cycloheptenyl group, a phenyl group, a naphthyl group, a pyridinyl group, and a pyrimidinyl group;

a cyclopentyl group, a cyclohexyl group, a cycloheptyl group, a cyclooctyl group, an adamantanyl group, a norbornanyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a cyclopentyl group, a cyclohexyl group, a cycloheptyl group, a cyclooctyl group, an adamantanyl group, a norbornanyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one of a deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and —B($Q_6$)($Q_7$) and —P(=O)($Q_8$)($Q_9$), wherein $Q_6$ to $Q_9$ may be each independently selected from —$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, and —$CD_2CDH_2$;

an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group; and an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group, each substituted with at least one of a deuterium, a $C_1$-$C_{10}$ alkyl group, and a phenyl group, but they are not limited thereto.

In an exemplary embodiment, in Formulae 2A and 2B, $R_1$, $R_2$, $R_{11}$, and $R_{12}$ may be each independently selected from:

a hydrogen, a deuterium, —F, a cyano group, a nitro group, —$SF_5$, a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl (adamantyl) group, a norbornanyl (norbornyl) group, a cyclopentenyl group, a cyclohexenyl group, a cycloheptenyl group, a phenyl group, a naphthyl group, a pyridinyl group, and a pyrimidinyl group;

a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornanyl group, a cyclopentenyl group, a cyclohexenyl group, a cycloheptenyl group, a phenyl group, a naphthyl group, a pyridinyl group, and a pyrimidinyl group, each substituted with at least one of a deuterium, —F, —CD₃, —CD₂H, —CDH₂, —CF₃, —CF₂H, —CFH₂, a cyano group, a nitro group, a C₁-C₁₀ alkyl group, a C₁-C₁₀ alkoxy group, a cyclopentyl group, a cyclohexyl group, a cycloheptyl group, a cyclooctyl group, an adamantanyl group, a norbornanyl group, a cyclopentenyl group, a cyclohexenyl group, a cycloheptenyl group, a phenyl group, a naphthyl group, a pyridinyl group, and a pyrimidinyl group; and —B(Q₆)(Q₇) and —P(=O)(Q₈)(Q₉), wherein Q₆ to Q₉ may be each independently selected from —CH₃, —CD₃, —CD₂H, —CDH₂, —CH₂CH₃, —CH₂CD₃, —CH₂CD₂H, —CH₂CDH₂, —CHDCH₃, —CHDCD₂H, —CHDCDH₂, —CHDCD₃, —CD₂CD₃, —CD₂CD₂H, and —CD₂CDH₂;

an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group; and an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group, each substituted with at least one of a deuterium, a C₁-C₁₀ alkyl group, and a phenyl group. In some exemplary embodiments, in Formulae 2A and 2B, R₁, R₂, R₁₁, and R₁₂ may be each independently selected from a hydrogen, a deuterium, —F, a cyano group, a nitro group, —SF₅, —CH₃, —CD₃, —CD₂H, —CDH₂, —CF₃, —CF₂H, —CFH₂, groups represented by Formulae 9-1 to 9-17 below, and groups represented by Formulae 10-1 to 10-30 below, but they are not limited thereto:

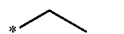
Formula 9-1

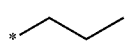
Formula 9-2

Formula 9-3

Formula 9-4

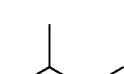
Formula 9-5

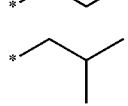
Formula 9-6

Formula 9-7

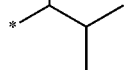
Formula 9-8

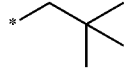
Formula 9-9

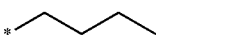
Formula 9-10

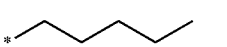
Formula 9-11

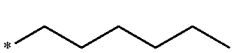
Formula 9-12

Formula 9-13

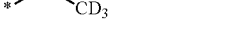
Formula 9-14

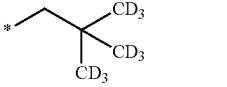
Formula 9-15

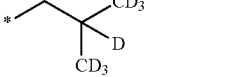
Formula 9-16

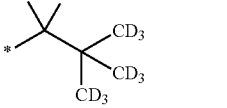
Formula 9-17

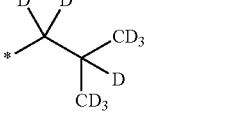
Formula 10-1

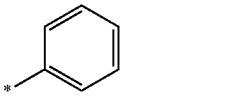
Formula 10-2

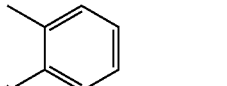
Formula 10-3

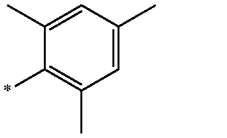
Formula 10-4

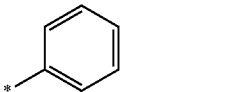
Formula 10-5

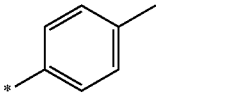
Formula 10-6

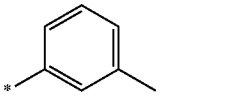
Formula 10-7

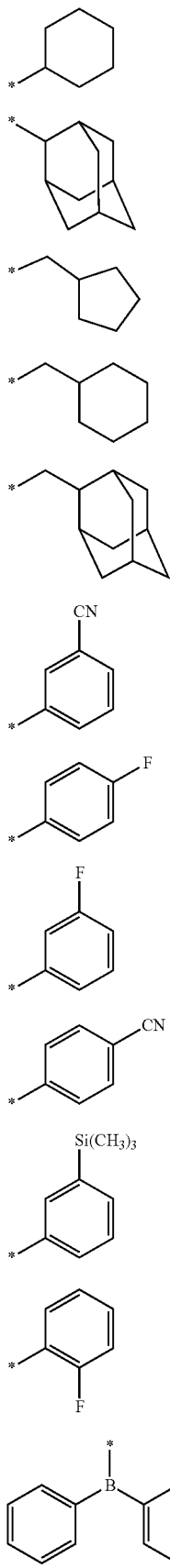
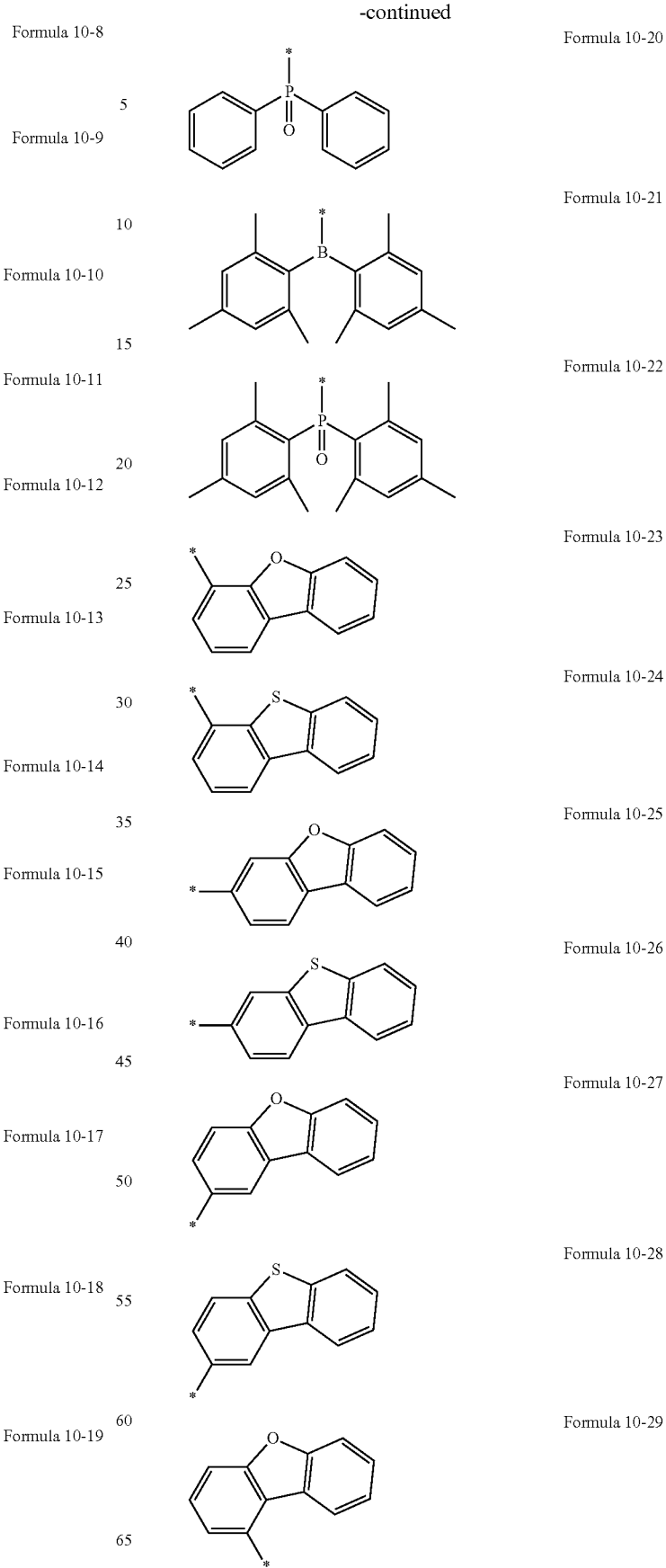

-continued

Formula 10-30

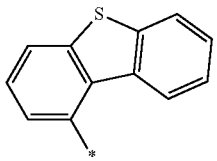

In Formula 2A, b1 and b2 may be each independently an integer selected from 0 to 4. In Formula 2B, c1 may be an integer selected from 0 to 16.

In Formula 2A, b1 denotes the number of $R_{11}$. When b1 is 2 or more, 2 or more groups $R_{11}$ may be identical to or different from each other. In Formula 2A, b2 denotes the number of groups $R_{12}$. When b2 is 2 or more, 2 or more groups $R_{12}$ may be identical to or different from each other. In Formula 2B, c1 denotes the number of $R_2$. When c1 is 2 or more, 2 or more groups $R_2$ may be identical to or different from each other.

When b1 is 2 or more, 2 or more groups $R_{11}$ may be optionally linked to each other to form a saturated or unsaturated ring (for example, a benzene, a naphthalene, a cyclohexane, an adamantane or a norbornane). When b2 is 2 or more, 2 or more groups $R_{12}$ may be optionally linked to each other to form a saturated or unsaturated ring (for example, a benzene, a naphthalene, a cyclohexane, an adamantane or a norbornane).

In Formula 2A, $R_{13}$ and $R_{14}$ may be each independently the group of Formula 2B, b3 denotes the number of groups $R_{13}$, b4 denotes the number of groups $R_{14}$, b3 and b4 may be each independently an integer selected from 0 to 4, and a sum of b3 and b4 (b3+b4) may be 1 or more. Thus, the ligand of Formula 2A may include at least one substituent represented by Formula 2B.

For example, in Formula 2A,
b3=1 and b4=0;
b3=0 and b4=1;
b3=1 and b4=1;
b3=2 and b4=0;
b3=0 and b4=2;
b3=1 and b4=2; or
b3=2 and b4=1, but they are not limited thereto.

For example, in Formula 2A, $R_{13}$ and $R_{14}$ may be each independently selected from groups represented by Formulae 2B-1 to 2B-5 below:

Formula 2B-1

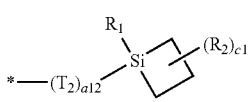

Formula 2B-2

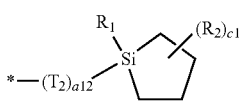

Formula 2B-3

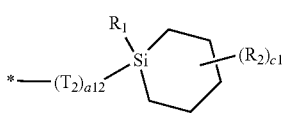

Formula 2B-4

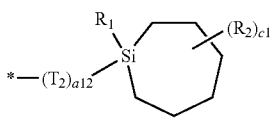

Formula 2B-5

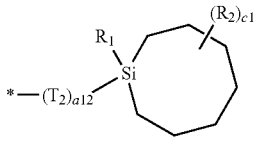

In Formulae 2B-1 to 2B-5, $T_2$, a12, $R_1$, $R_2$, and c1 are defined the same as those provided herein.

For example, in Formulae 2B-1 to 2B-5, $T_2$ may be selected from:

a $C_1$-$C_5$ alkylene group, a cyclopentylene group, a cyclohexylene group, a cycloheptylene group, a cyclooctylene group, a cyclopentenylene group, a cyclohexenylene group, a cycloheptenylene group, a phenylene group, a naphthylene group, a fluorenylene group, a phenanthrenylene group, a triphenylenylene group, a pyrenylene group, a chrysenylene group, a pyridinylene group, a pyrimidinylene group, a carbazolylene group, a triazinylene group, a dibenzofuranylene group, and a dibenzothiophenylene group; and a $C_1$-$C_5$ alkylene group, a cyclopentylene group, a cyclohexylene group, a cycloheptylene group, a cyclooctylene group, a cyclopentenylene group, a cyclohexenylene group, a cycloheptenylene group, a phenylene group, a naphthylene group, a fluorenylene group, a phenanthrenylene group, a triphenylenylene group, a pyrenylene group, a chrysenylene group, a pyridinylene group, a pyrimidinylene group, a carbazolylene group, a triazinylene group, a dibenzofuranylene group, and a dibenzothiophenylene group, each substituted with at least one of a deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, and a naphthyl group;

a12 may be 0 or 1;

$R_1$ and $R_2$ may be each independently selected from:

a hydrogen, a deuterium, —F, a cyano group, a nitro group, —SF$_5$, a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornanyl group, a cyclopentenyl group, a cyclohexenyl group, a cycloheptenyl group, a phenyl group, a naphthyl group, a pyridinyl group, and a pyrimidinyl group;

a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornanyl group, a cyclopentenyl group, a cyclohexenyl group, a cycloheptenyl group, a phenyl group, a naphthyl group, a pyridinyl group, and a pyrimidinyl group, each substituted with at least one of a deuterium, —F, —CD$_3$, —CD$_2$H, —CDH$_2$, —CF$_3$, —CF$_2$H, —CFH$_2$, a cyano group, a nitro group, a $C_1$-$C_{10}$ alkyl group, a $C_1$-$C_{10}$ alkoxy group, a cyclopentyl group, a cyclohexyl group, a cycloheptyl group, a cyclooctyl group, an adamantanyl group, a norbornanyl group, a cyclopentenyl group, a cyclohexenyl group, a cycloheptenyl group, a phenyl group, a naphthyl group, a pyridinyl group, and a pyrimidinyl group; and —B(Q$_6$)(Q$_7$) and —P(=O)(Q$_8$)(Q$_9$), wherein Q$_6$ to Q$_9$ may be each independently selected from:

—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;

an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group; and an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group, each substituted with at least one of a deuterium, a $C_1$-$C_{10}$ alkyl group and a phenyl group; and c1 may be an integer selected from 0 to 6.

In some exemplary embodiments, in Formula 2A, $R_{13}$ and $R_{14}$ may be each independently selected from groups represented by Formulae 2B(1) to 2B(18) below:

Formula 2B(1)

Formula 2B(2)

Formula 2B(3)

Formula 2B(4)

Formula 2B(5)

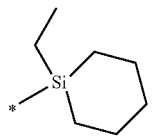

Formula 2B(6)

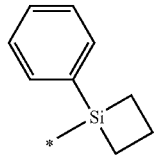

Formula 2B(7)

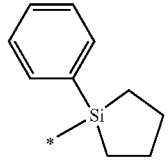

Formula 2B(8)

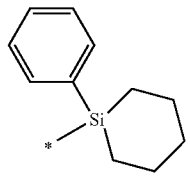

Formula 2B(9)

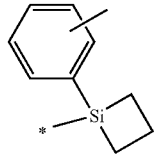

Formula 2B(10)

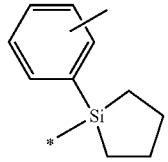

Formula 2B(11)

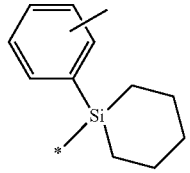

Formula 2B(12)

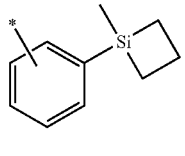

Formula 2B(13)

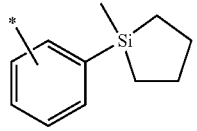

Formula 2B(14)

-continued
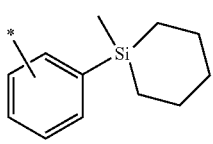
Formula 2B(15)
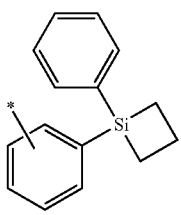
Formula 2B(16)
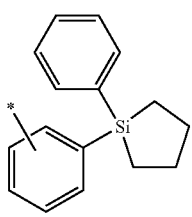
Formula 2B(17)
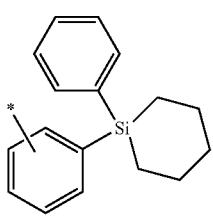
Formula 2B(18)
In some other exemplary embodiments, in Formula 1, $L_1$ may be selected from ligands represented by Formulae 2A-1 to 2A-45 below:
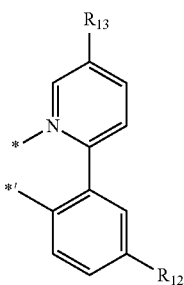
Formula 2A-1
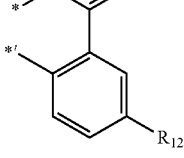
Formula 2A-2
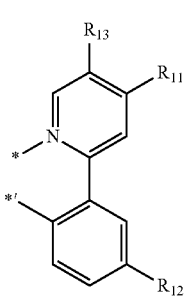
Formula 2A-3
Formula 2A-4
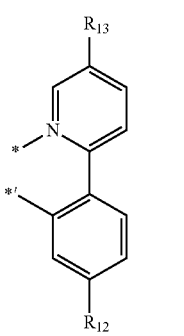
Formula 2A-5
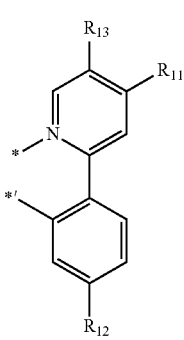
Formula 2A-6
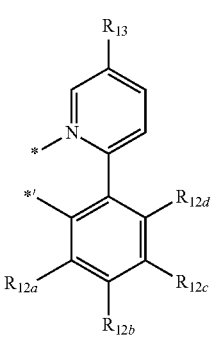
Formula 2A-7

Formula 2A-8
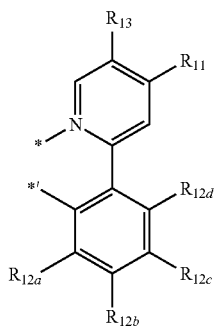
Formula 2A-9
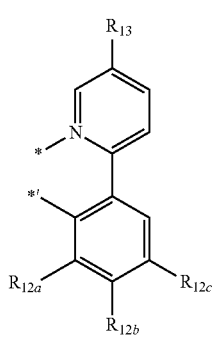
Formula 2A-10
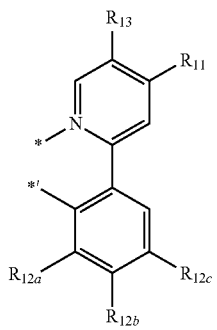
Formula 2A-11
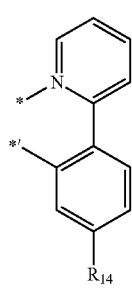
Formula 2A-12
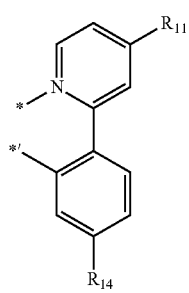
Formula 2A-13
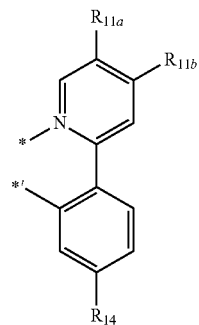
Formula 2A-14
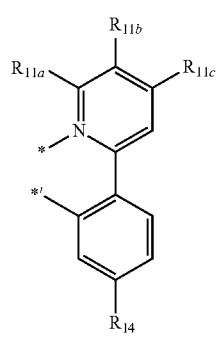
Formula 2A-15
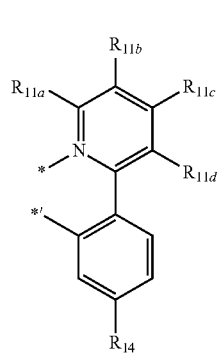
Formula 2A-16
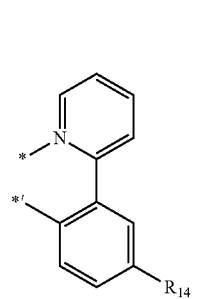
Formula 2A-17
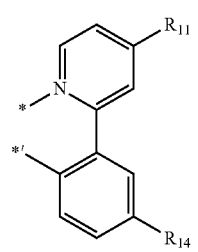

-continued
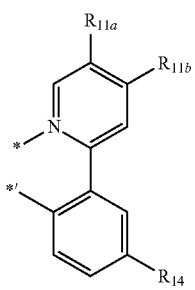
Formula 2A-18
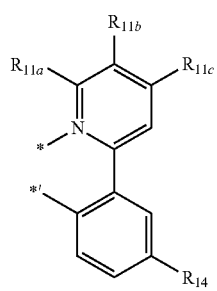
Formula 2A-19
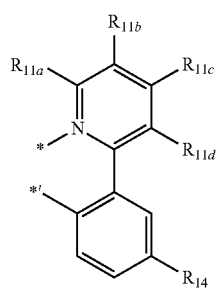
Formula 2A-20
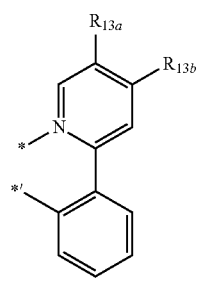
Formula 2A-21
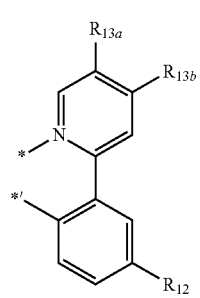
Formula 2A-22
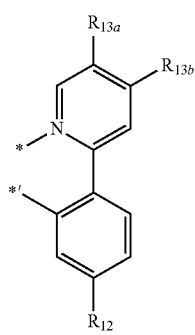
Formula 2A-23
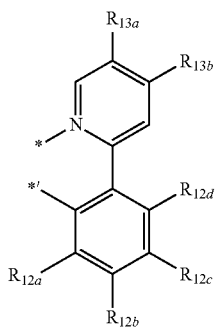
Formula 2A-24
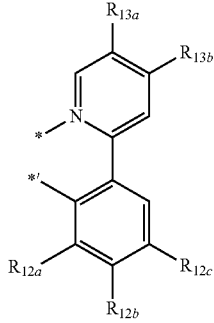
Formula 2A-25
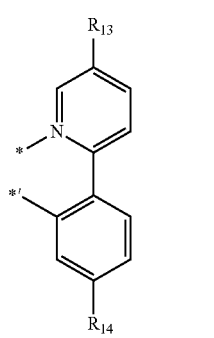
Formula 2A-26
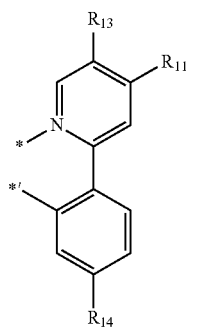
Formula 2A-27

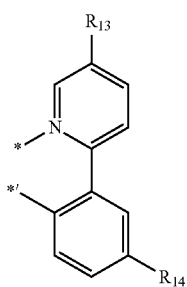
Formula 2A-28
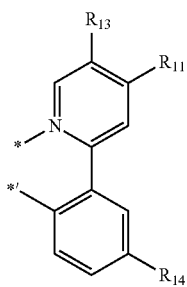
Formula 2A-29
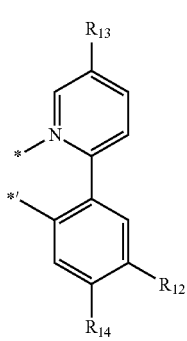
Formula 2A-30
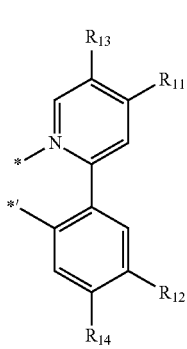
Formula 2A-31
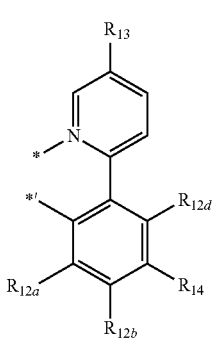
Formula 2A-32
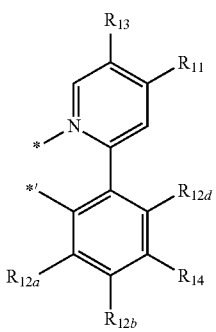
Formula 2A-33
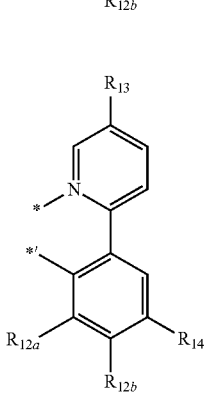
Formula 2A-34
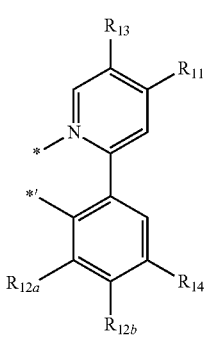
Formula 2A-35
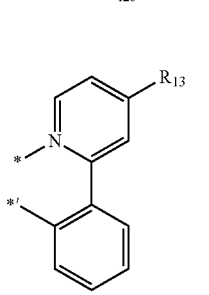
Formula 2A-36
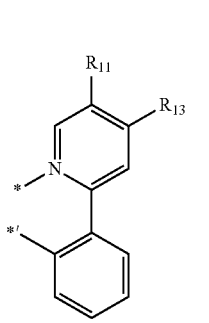
Formula 2A-37

-continued

Formula 2A-38
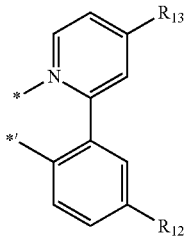

Formula 2A-39
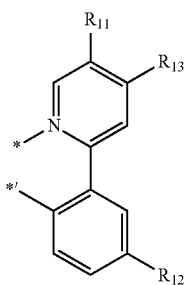

Formula 2A-40
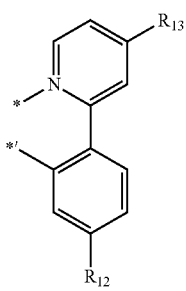

Formula 2A-41
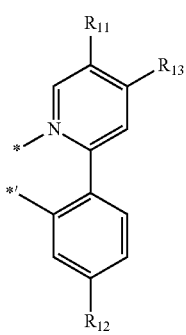

Formula 2A-42
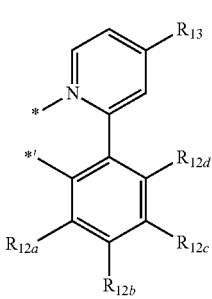

-continued

Formula 2A-43
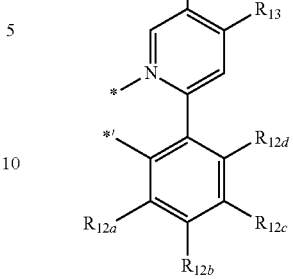

Formula 2A-44
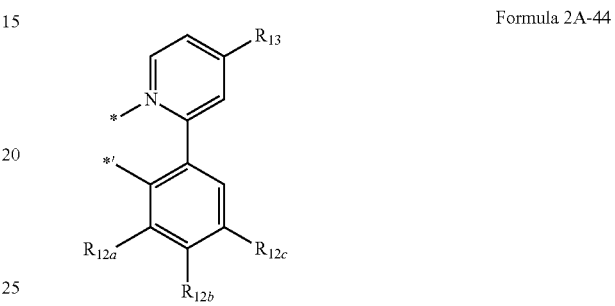

Formula 2A-45
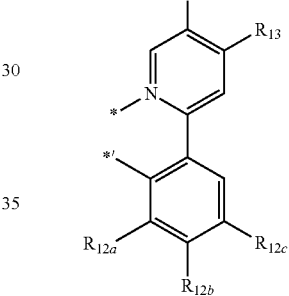

In Formulae 2A-1 to 2A-45, $R_{11}$ to $R_{14}$ are each independently defined in the same way as above, $R_{11a}$ to $R_{11c}$ are defined in the same way as group $R_{11}$, $R_{12a}$ to $R_{12c}$ are defined in the same way as group $R_{12}$, $R_{13a}$, and $R_{13b}$ are defined in the same way as group $R_{13}$, wherein $R_{11}$, $R_{11a}$ to $R_{11c}$, $R_{12}$, and $R_{12a}$ to $R_{12c}$ are not a hydrogen.

For example, in Formula 2A-1 to 2A-45, $R_{11}$, $R_{11a}$ to $R_{11c}$, $R_{12}$, and $R_{12a}$ to $R_{12c}$ may be each independently selected from:

a deuterium, —F, a cyano group, a nitro group, —SF$_5$, a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornanyl group, a cyclopentenyl group, a cyclohexenyl group, a cycloheptenyl group, a phenyl group, a naphthyl group, a pyridinyl group, and a pyrimidinyl group;

a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornanyl group, a cyclopentenyl group, a cyclohexenyl group, a cycloheptenyl group, a phenyl group, a naphthyl group, a pyridinyl group, and a pyrimidinyl group, each substituted with at least one of a deuterium, —F, —CD$_3$, —CD$_2$H, —CDH$_2$, —CF$_3$, —CF$_2$H, —CFH$_2$, a cyano group, a nitro group, a C$_1$-C$_{10}$ alkyl group, a C$_1$-C$_{10}$ alkoxy group, a cyclopentyl group, a cyclohexyl group, a cycloheptyl group, a cyclooctyl group, an adamantanyl group, a norbornanyl group, a cyclopentenyl group, a cyclohexenyl group, a cycloheptenyl group, a phenyl group, a naphthyl group, a pyridinyl group, and a pyrimidinyl group; and —B(Q$_6$)(Q$_7$), and —P(=O)(Q$_8$)(Q$_9$), wherein Q$_6$ to Q$_9$ may be each independently selected from:

—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;

an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group; and an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group, each substituted with at least one of a deuterium, a C$_1$-C$_{10}$ alkyl group, and a phenyl group; and R$_{13}$ and R$_{14}$ may be each independently selected from the groups of Formulae 2B-1 to 2B-5 above, but they are not limited thereto.

In some exemplary embodiments, in Formulae 2A-1 to 2A-45,

R$_{11}$, R$_{11a}$ to R$_{11c}$, R$_{12}$, and R$_{12a}$ to R$_{12c}$ may be each independently selected from a deuterium, —F, a cyano group, a nitro group, —SF$_5$, —CH$_3$, —CD$_3$, —CD$_2$H, —CDH$_2$, —CF$_3$, —CF$_2$H, —CFH$_2$, the groups of Formulae 9-1 to 9-17 above, and the groups of Formulae 10-1 to 10-30 above; and R$_{13}$ and R$_{14}$ may be each independently selected from the groups of Formulae 2B(1) to 2B(18) above, but they are not limited thereto.

In Formula 1, L$_2$ may be selected from ligands represented by Formulae 3A to 3G below:

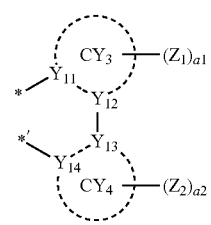
Formula 3A

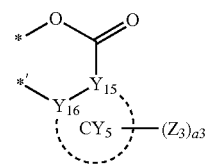
Formula 3B

Formula 3C

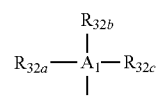
Formula 3D

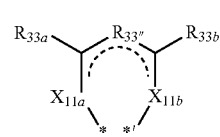
Formula 3E

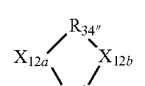
Formula 3F

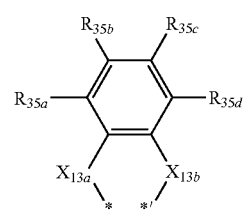
Formula 3G

In Formulae 3A to 3G,

Y$_{11}$ to Y$_{16}$ may be each independently C or N, wherein Y$_{11}$ and Y$_{12}$ may be connected to each other via a single bond or a double bond, Y$_{13}$ and Y$_{14}$ may be connected to each other via a single bond or a double bond, and Y$_{15}$ and Y$_{16}$ may be connected to each other via a single bond or a double bond;

CY$_3$ to CY$_5$ may be each independently selected from a C$_5$-C$_{60}$ carbocyclic group and a C$_2$-C$_{60}$ heterocyclic group (e.g., "a monocyclic group" or "a polycyclic group");

a1 to a3 may be each independently an integer selected from 1 to 5;

A$_1$ may be P or As;

X$_{11a}$, X$_{11b}$, X$_{12a}$, X$_{12b}$, X$_{13a}$, and X$_{13b}$ may be each independently selected from N, O, N(R$_{34}$), P(R$_{35}$)(R$_{36}$), and As(R$_{37}$)(R$_{38}$) (wherein X$_{12a}$, X$_{12b}$, X$_{13a}$, and X$_{13b}$ is not N nor O);

R$_{33''}$ and R$_{34''}$ may be each independently selected from a single bond, a double bond, a substituted or unsubstituted C$_1$-C$_5$ alkylene group, a substituted or unsubstituted C$_2$-C$_5$ alkenylene group, and a substituted or unsubstituted C$_6$-C$_{10}$ arylene group;

Z$_1$ to Z$_3$, R$_{31}$, R$_{32a}$, R$_{32b}$, R$_{32c}$, R$_{33a}$, R$_{33b}$, R$_{34}$ to R$_{38}$, R$_{35a}$, R$_{35b}$, R$_{35c}$, and R$_{35d}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$N(Q_1)(Q_2)$, —$Si(Q_3)(Q_4)(Q_5)$, —$B(Q_6)(Q_7)$, and —$P(=O)(Q_8)(Q_9)$;

* and *' each indicates a binding site to M of Formula 1; and at least one of substituents of the substituted $C_1$-$C_5$ alkylene group, the substituted $C_2$-$C_5$ alkenylene group, the substituted $C_6$-$C_{10}$ arylene group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

a deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{11})(Q_{12})$, —$Si(Q_{13})(Q_{14})(Q_{15})$, —$B(Q_{16})(Q_{17})$, and —$P(=O)(Q_{18})(Q_{19})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one of a deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{21})(Q_{22})$, —$Si(Q_{23})(Q_{24})(Q_{25})$, —$B(Q_{26})(Q_{27})$, and —$P(=O)(Q_{28})(Q_{29})$; and —$N(Q_{31})(Q_{32})$, —$Si(Q_{33})(Q_{34})(Q_{35})$, —$B(Q_{36})(Q_{37})$, and —$P(=O)(Q_{38})(Q_{39})$, wherein $Q_1$ to $Q_9$, $Q_{11}$ to $Q_{19}$, $Q_{21}$ to $Q_{29}$, and $Q_{31}$ to $Q_{39}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In an exemplary embodiment, in Formulae 3A and 3B, $CY_3$ to $CY_5$ may be each independently selected from a benzene, a naphthalene, a fluorene, a spiro-fluorene, an indene, a pyrrole, a thiophene, a furan, an imidazole, a pyrazole, a thiazole, an isothiazole, an oxazole, an isooxazole, a pyridine, a pyrazine, a pyrimidine, a pyridazine, a quinoline, an isoquinoline, a benzoquinoline, a quinoxaline, a quinazoline, a carbazole, a benzoimidazole, a benzofuran, a benzothiophene, an isobenzothiophene, a benzooxazole, an isobenzooxazole, a triazole, a tetrazole, an oxadiazole, a triazine, a dibenzofuran, a dibenzothiophene, 5,6,7,8-tetrahydroisoquinoline, and 1,2,3,4-tetrahydronaphthalene, but they are not limited thereto.

For example, in Formula 1, $L_2$ may be selected from the ligands of Formulae 3-1 to 3-118 below, but is not limited thereto:

Formula 3-1
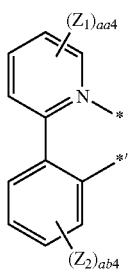
Formula 3-2
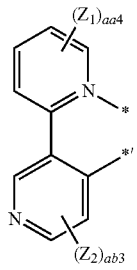
Formula 3-3
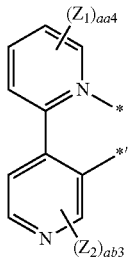
Formula 3-4
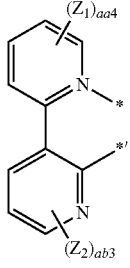
Formula 3-5
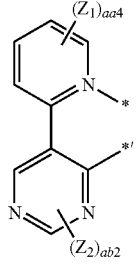
Formula 3-6
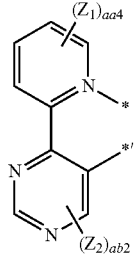
Formula 3-7
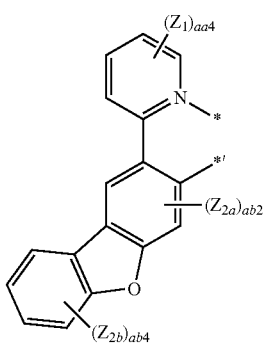
Formula 3-8
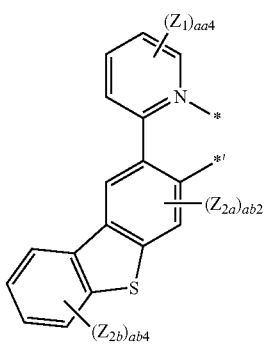
Formula 3-9
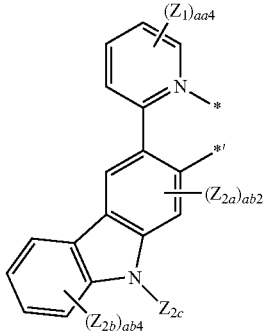
Formula 3-10
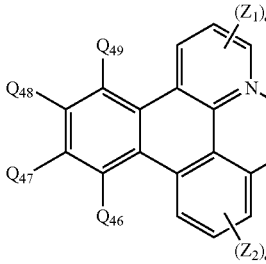
Formula 3-11
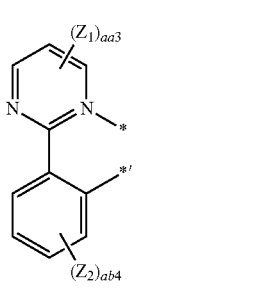

-continued
Formula 3-12
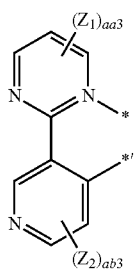
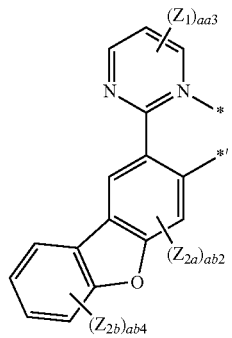
Formula 3-17
Formula 3-13
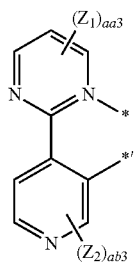
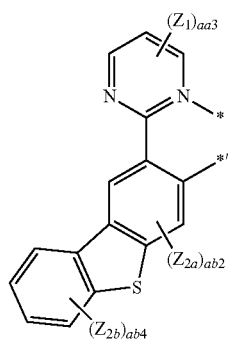
Formula 3-18
Formula 3-14
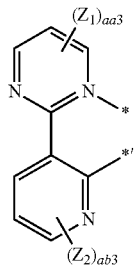
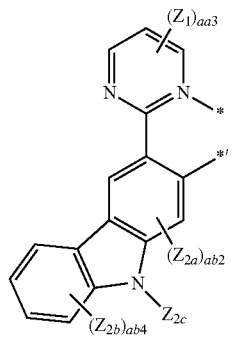
Formula 3-19
Formula 3-15
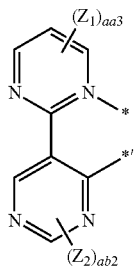
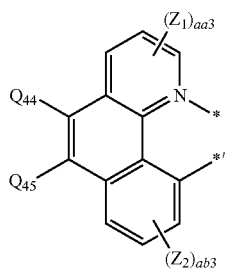
Formula 3-20
Formula 3-16
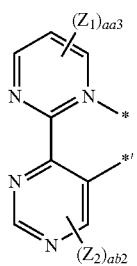
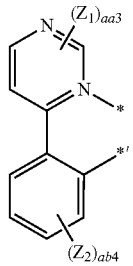
Formula 3-21

Formula 3-22

Formula 3-23

Formula 3-24

Formula 3-25

Formula 3-26

Formula 3-27

Formula 3-28

Formula 3-29

Formula 3-30

Formula 3-31

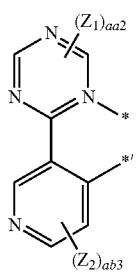
Formula 3-32
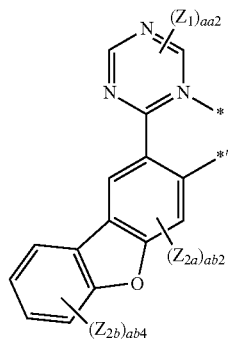
Formula 3-37
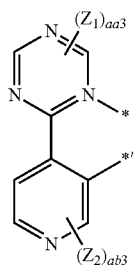
Formula 3-33
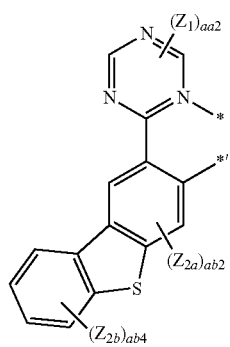
Formula 3-38
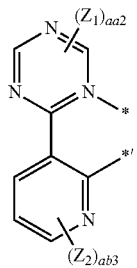
Formula 3-34
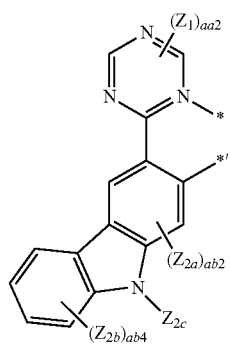
Formula 3-39
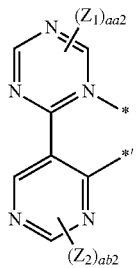
Formula 3-35
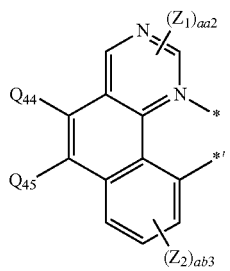
Formula 3-40
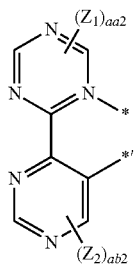
Formula 3-36
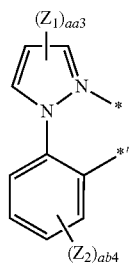
Formula 3-41

Formula 3-42 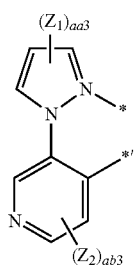
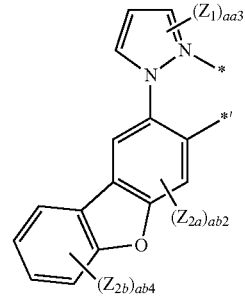 Formula 3-47
Formula 3-43 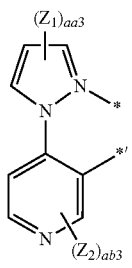
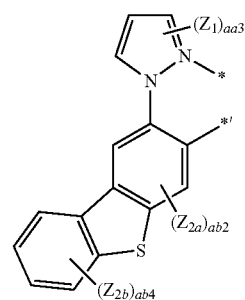 Formula 3-48
Formula 3-44 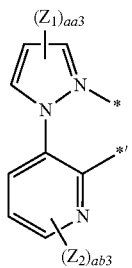
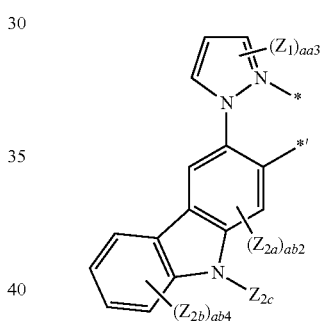 Formula 3-49
Formula 3-45 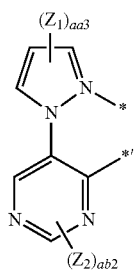
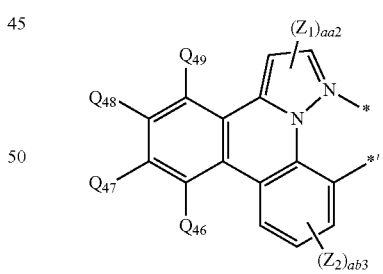 Formula 3-50
Formula 3-46 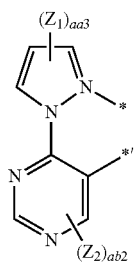
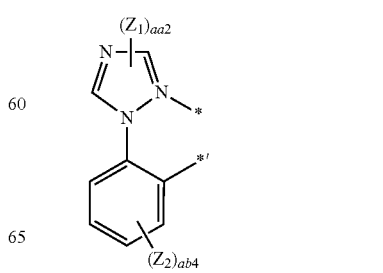 Formula 3-51

Formula 3-52 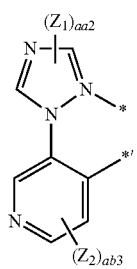
Formula 3-57 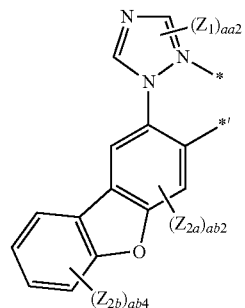
Formula 3-53 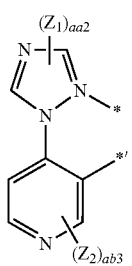
Formula 3-58 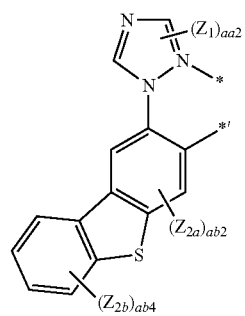
Formula 3-54 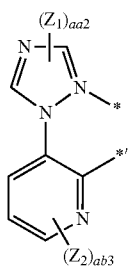
Formula 3-59 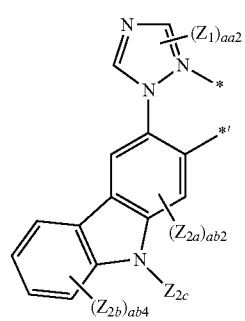
Formula 3-55 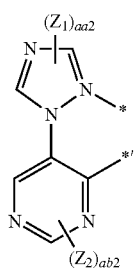
Formula 3-60 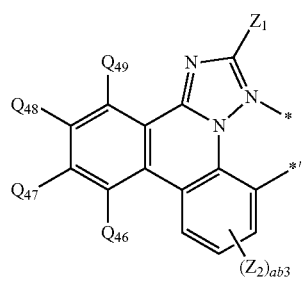
Formula 3-56 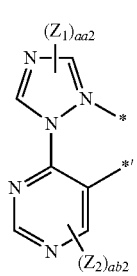
Formula 3-61 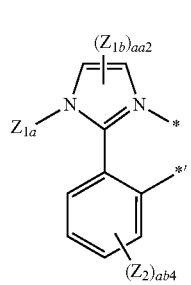

49
-continued
Formula 3-62
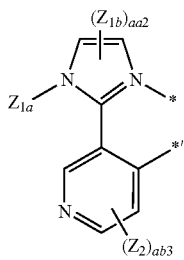
Formula 3-63
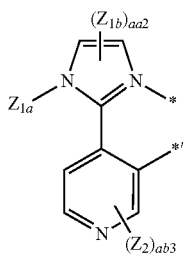
Formula 3-64
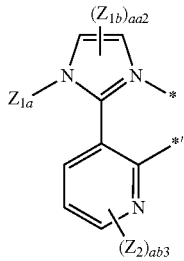
Formula 3-65
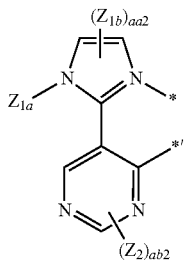
Formula 3-66
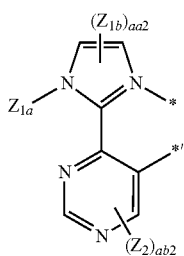
Formula 3-67
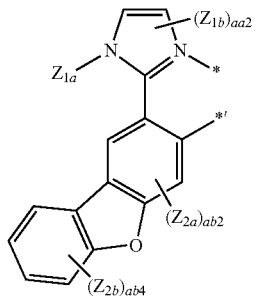
50
-continued
Formula 3-68
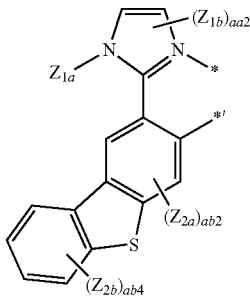
Formula 3-69
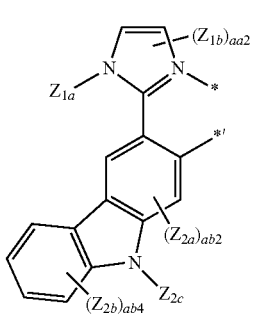
Formula 3-70
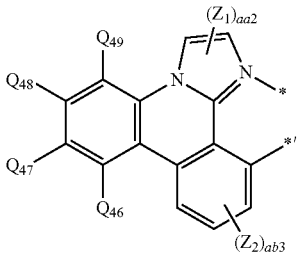
Formula 3-71
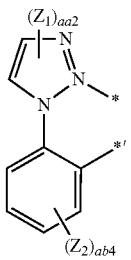
Formula 3-72
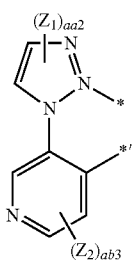

Formula 3-73 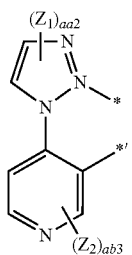
Formula 3-74 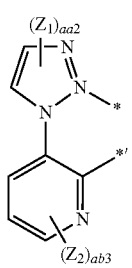
Formula 3-75 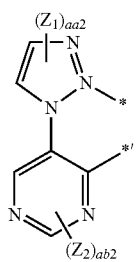
Formula 3-76 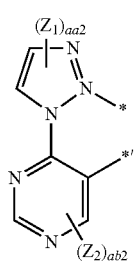
Formula 3-77 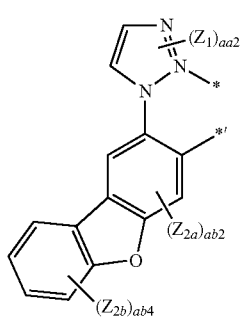
Formula 3-78 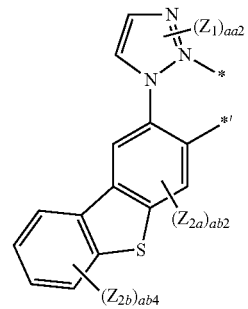
Formula 3-79 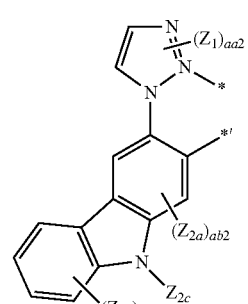
Formula 3-80 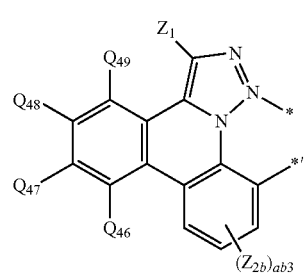
Formula 3-81 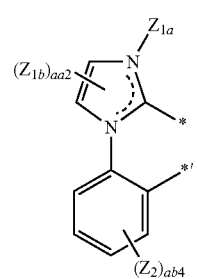
Formula 3-82 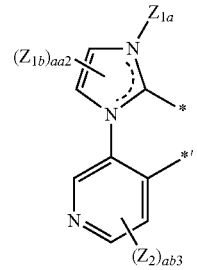

Formula 3-83
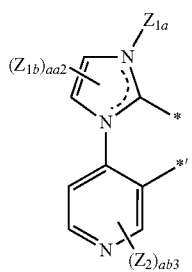
Formula 3-84
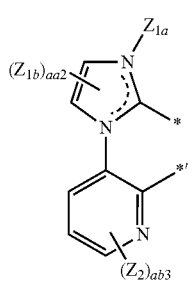
Formula 3-85
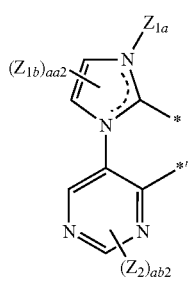
Formula 3-86
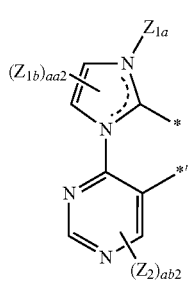
Formula 3-87
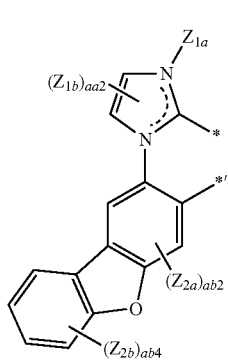
Formula 3-88
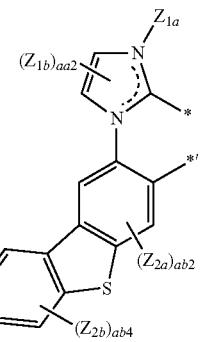
Formula 3-89
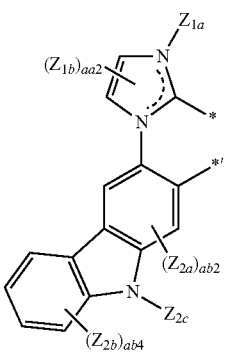
Formula 3-90
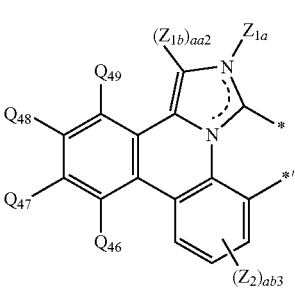
Formula 3-91
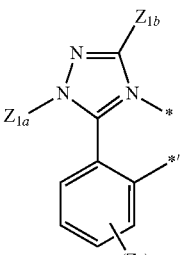
Formula 3-92
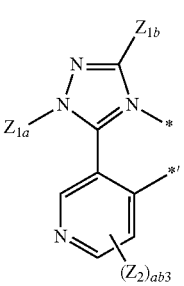

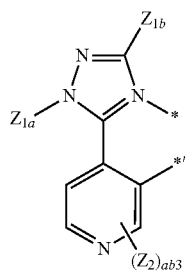
Formula 3-93
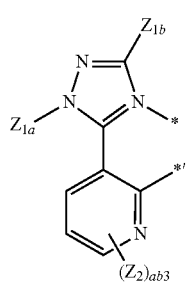
Formula 3-94
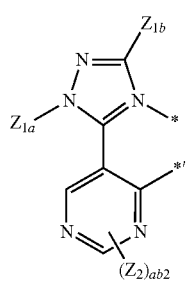
Formula 3-95
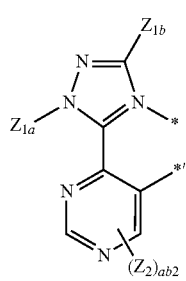
Formula 3-96
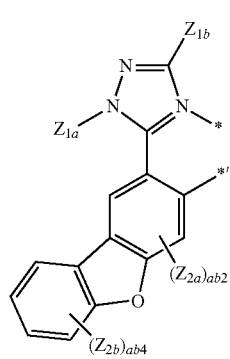
Formula 3-97
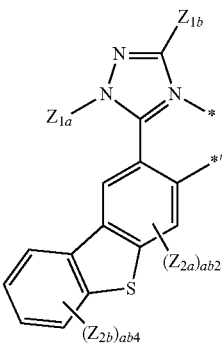
Formula 3-98
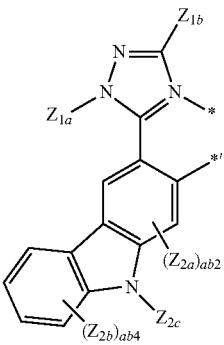
Formula 3-99
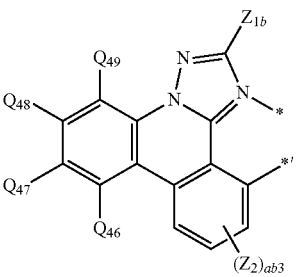
Formula 3-100
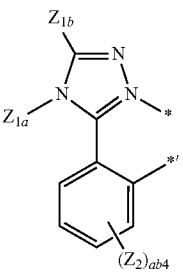
Formula 3-101
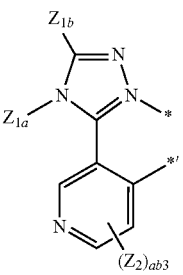
Formula 3-102

Formula 3-103 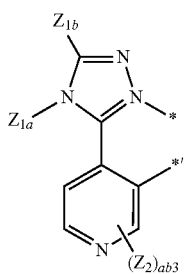
Formula 3-104
Formula 3-105
Formula 3-106
Formula 3-107
Formula 3-108 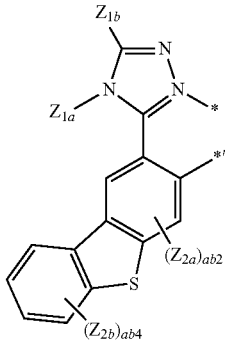
Formula 3-109 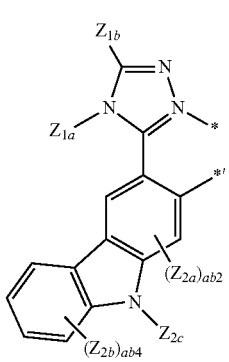
Formula 3-110 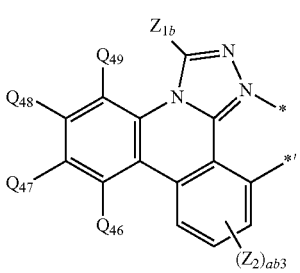
Formula 3-111 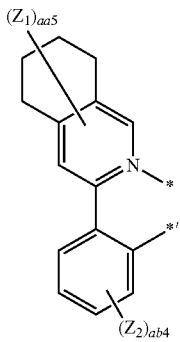
Formula 3-112 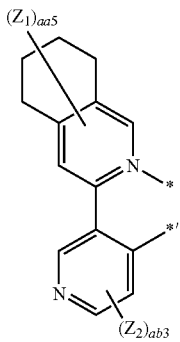

-continued

Formula 3-113

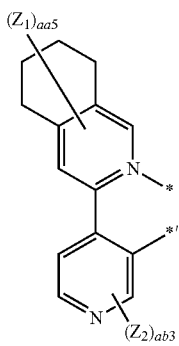

Formula 3-114

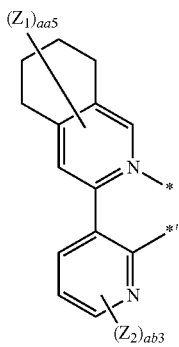

Formula 3-115

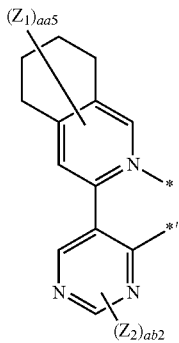

Formula 3-116

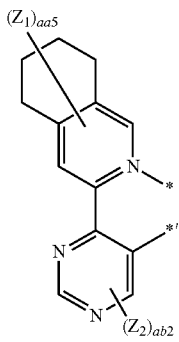

Formula 3-117

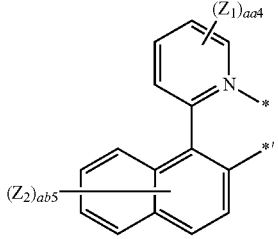

Formula 3-118

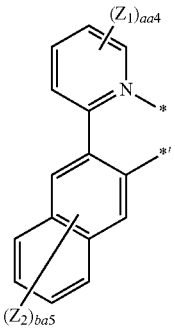

In Formulae 3-1 to 3-118, $Z_1$, $Z_2$, $Z_{1a}$, $Z_{1b}$, $Z_{2a}$, $Z_{2b}$, and $Z_{2c}$ may be each independently selected from:

a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, a C$_1$-C$_{20}$ alkyl group, and a C$_1$-C$_{20}$ alkoxy group;

a C$_1$-C$_{20}$ alkyl group and a C$_1$-C$_{20}$ alkoxy group, each substituted with at least one of a deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{10}$ alkyl group, a cyclopentyl group, a cyclohexyl group, a cycloheptyl group, a cyclooctyl group, an adamantanyl group, a norbornanyl group, a cyclopentenyl group, a cyclohexenyl group, a cycloheptenyl group, a phenyl group, a naphthyl group, a pyridinyl group, and a pyrimidinyl group;

a cyclopentyl group, a cyclohexyl group, a cycloheptyl group, a cyclooctyl group, an adamantanyl group, a norbornanyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a cyclopentyl group, a cyclohexyl group, a cycloheptyl group, a cyclooctyl group, an adamantanyl group, a norbornanyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one of a deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and —N($Q_1$)($Q_2$), —Si($Q_3$)($Q_4$)($Q_5$), —B($Q_6$)($Q_7$), and —P(=O)($Q_8$)($Q_9$), wherein $Q_1$ to $Q_9$ may be each independently selected from —CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;

an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group; and an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group, each substituted with at least one of a deuterium and a $C_1$-$C_{10}$ alkyl group;

aa2 and ab2 may be each independently 1 or 2;

aa3 and ab3 may be each independently an integer selected from 1 to 3;

aa4 and ab4 may be each independently an integer selected from 1 to 4;

aa5 may be an integer selected from 1 to 10;

ab5 may be an integer selected from 1 to 6; and

\* and \*' each indicates a binding site to M of Formula 1.

For example, in Formulae 3-1 to 3-118, $Z_1$, $Z_2$, $Z_{1a}$, $Z_{1b}$, $Z_{2a}$, $Z_{2b}$, and $Z_{2c}$ may be each independently selected from:

a hydrogen, a deuterium, —F, a cyano group, a nitro group, —SF$_5$, a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornanyl group, a cyclopentenyl group, a cyclohexenyl group, a cycloheptenyl group, a phenyl group, a naphthyl group, a pyridinyl group, and a pyrimidinyl group;

a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornanyl group, a cyclopentenyl group, a cyclohexenyl group, a cycloheptenyl group, a phenyl group, a naphthyl group, a pyridinyl group, and a pyrimidinyl group, each substituted with at least one of a deuterium, —F, —CD$_3$, —CD$_2$H, —CDH$_2$, —CF$_3$, —CF$_2$H, —CFH$_2$, a cyano group, a nitro group, a $C_1$-$C_{10}$ alkyl group, a $C_1$-$C_{10}$ alkoxy group, a cyclopentyl group, a cyclohexyl group, a cycloheptyl group, a cyclooctyl group, an adamantanyl group, a norbornanyl group, a cyclopentenyl group, a cyclohexenyl group, a cycloheptenyl group, a phenyl group, a naphthyl group, a pyridinyl group, and a pyrimidinyl group; and —N($Q_1$)($Q_2$), —Si($Q_3$)($Q_4$)($Q_5$), —B($Q_6$)($Q_7$), and —P(=O)($Q_8$)($Q_9$), wherein $Q_1$ to $Q_9$ may be each independently selected from:

—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;

an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group; and an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group, each substituted with at least one of a deuterium and a C$_1$-C$_{10}$ alkyl group, but they are not limited thereto.
In an exemplary embodiment, L$_2$ in Formula 1 may be selected from ligands represented by Formulae 3-1(1) to 3-1(70) below:
Formula 3-1(1)
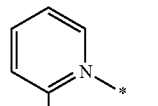
Formula 3-1(2)
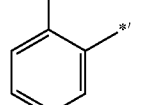
Formula 3-1(3)
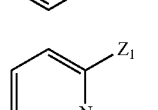
Formula 3-1(4)
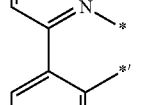
Formula 3-1(5)
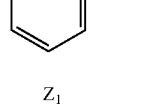
Formula 3-1(6)
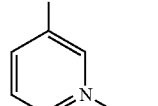
-continued
Formula 3-1(7)
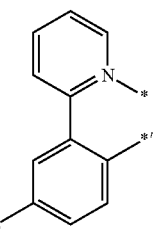
Formula 3-1(8)
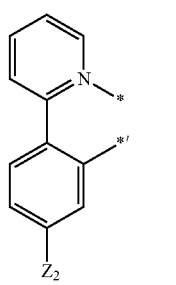
Formula 3-1(9)
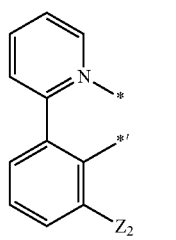
Formula 3-1(10)
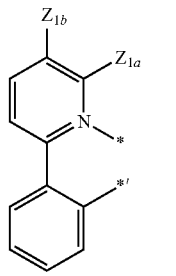
Formula 3-1(11)
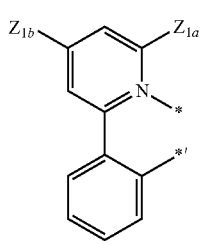
Formula 3-1(12)
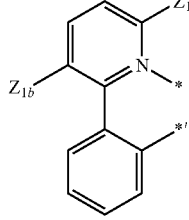

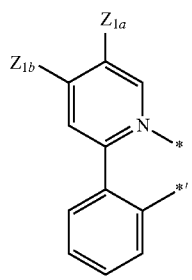
Formula 3-1(13)
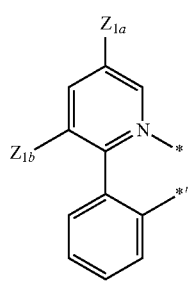
Formula 3-1(14)
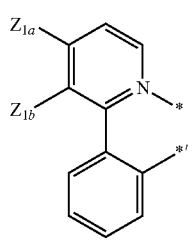
Formula 3-1(15)
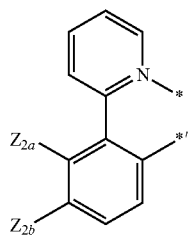
Formula 3-1(16)
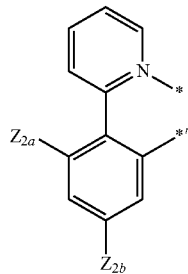
Formula 3-1(17)
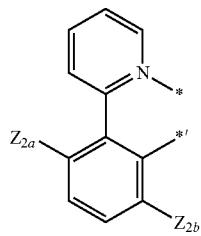
Formula 3-1(18)
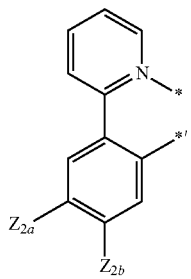
Formula 3-1(19)
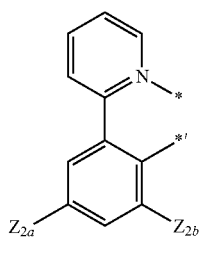
Formula 3-1(20)
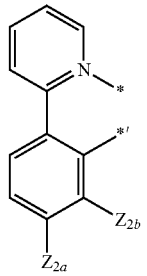
Formula 3-1(21)
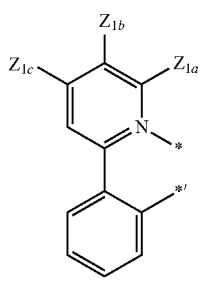
Formula 3-1(22)
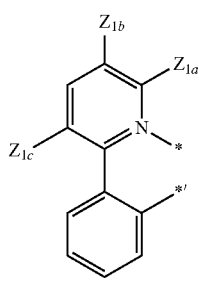
Formula 3-1(23)
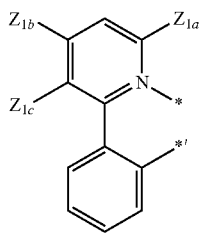
Formula 3-1(24)

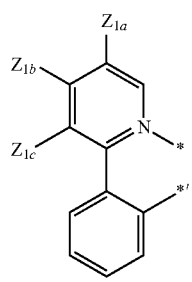
Formula 3-1(25)
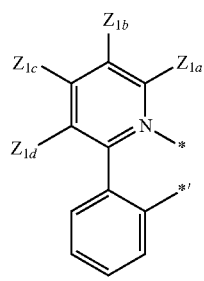
Formula 3-1(30)
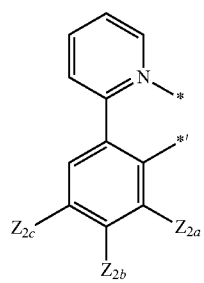
Formula 3-1(26)
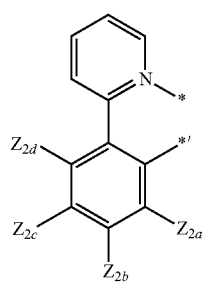
Formula 3-1(31)
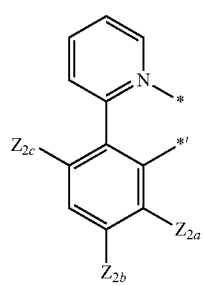
Formula 3-1(27)
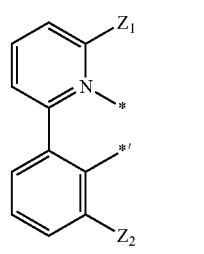
Formula 3-1(32)
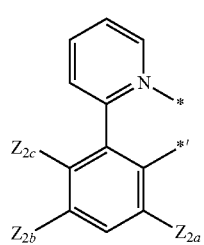
Formula 3-1(28)
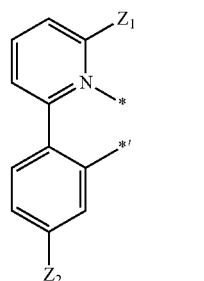
Formula 3-1(33)
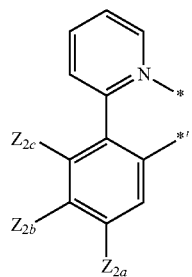
Formula 3-1(29)
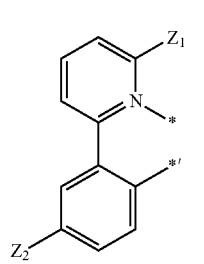
Formula 3-1(34)
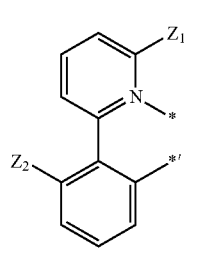
Formula 3-1(35)

Formula 3-1(36)
Formula 3-1(37)
Formula 3-1(38)
Formula 3-1(39)
Formula 3-1(40)
Formula 3-1(41)
Formula 3-1(42)
Formula 3-1(43)
Formula 3-1(44)
Formula 3-1(45)

-continued
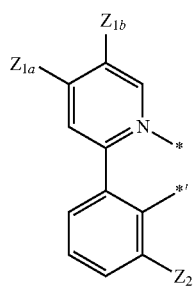
Formula 3-1(46)
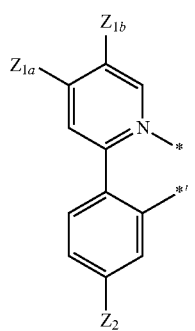
Formula 3-1(47)
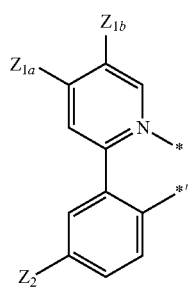
Formula 3-1(48)
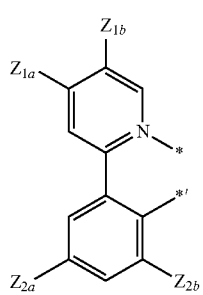
Formula 3-1(49)
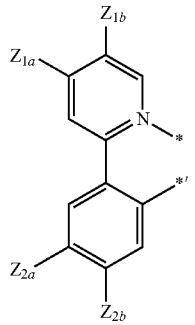
Formula 3-1(50)
-continued
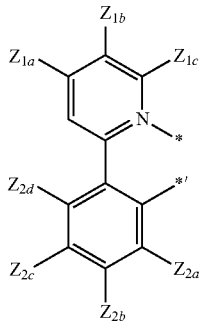
Formula 3-1(51)
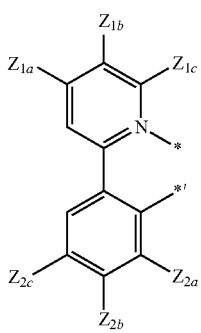
Formula 3-1(52)
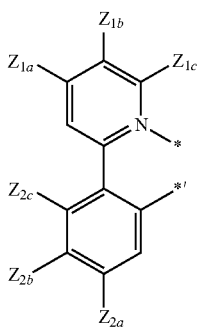
Formula 3-1(53)
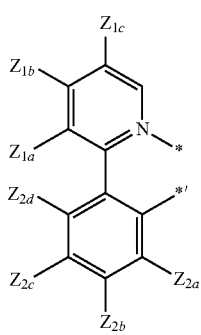
Formula 3-1(54)
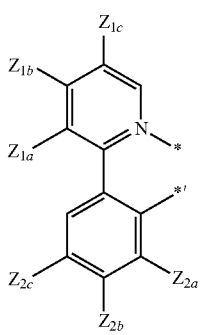
Formula 3-1(55)

Formula 3-1(56)
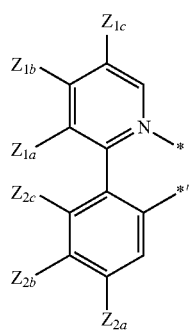
Formula 3-1(57)
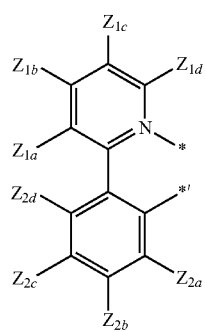
Formula 3-1(58)
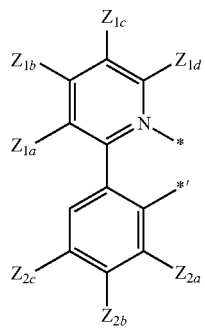
Formula 3-1(59)
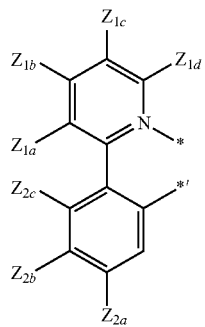
Formula 3-1(60)
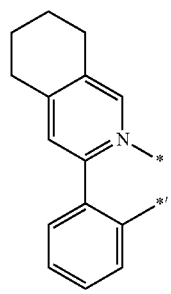
Formula 3-1(61)
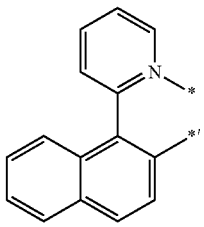
Formula 3-1(62)
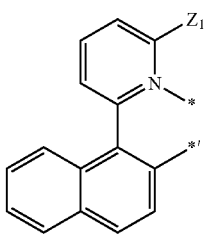
Formula 3-1(63)
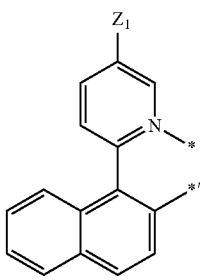
Formula 3-1(64)
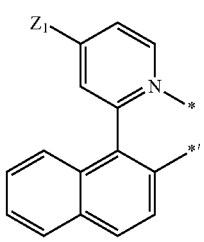
Formula 3-1(65)
Formula 3-1(66)
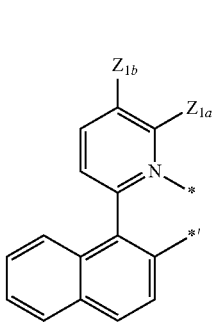

-continued

Formula 3-1(67)

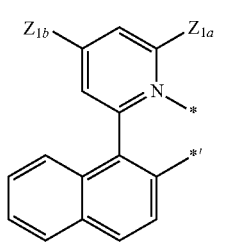

Formula 3-1(68)

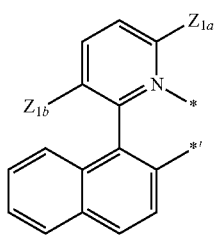

Formula 3-1(69)

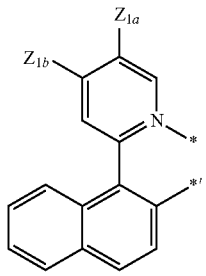

Formula 3-1(70)

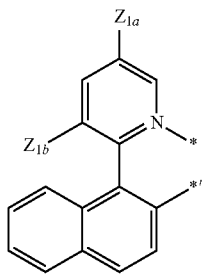

In Formulae 3-1(1) to 3-1(70), $Z_1$, $Z_2$, $Z_{1a}$, $Z_{1b}$, $Z_{1c}$, $Z_{1d}$, $Z_{2a}$, $Z_{2b}$, $Z_{2c}$, and $Z_{2d}$ may be each independently selected from a deuterium, —F, a cyano group, a nitro group, —SF$_5$, —CH$_3$, —CD$_3$, —CD$_2$H, —CDH$_2$, —CF$_3$, —CF$_2$H, —CFH$_2$, —Si(Q$_3$)(Q$_4$)(Q$_5$), the groups of Formulae 9-1 to 9-17 above, and the groups of Formulae 10-1 to 10-30 above, wherein $Q_3$ to $Q_5$ may be each independently selected from
—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;

an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group; and an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group, each substituted with at least one of a deuterium and a C$_1$-C$_{10}$ alkyl group.

In some exemplary embodiments, L$_2$ in Formula 1 may be selected from ligands represented by Formulae 3-1(a) and 3-117(a) below:

Formula 3-1(a)

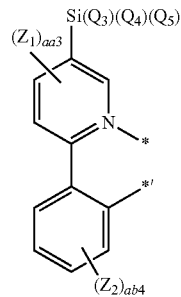

Formula 3-117(a)

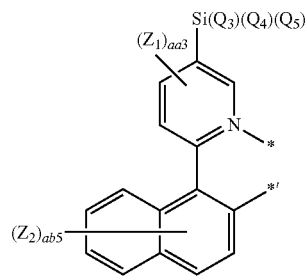

In Formulae e3-1(a) and 3-117(a), $Z_1$, $Z_2$, aa3, ab4, ab5, and $Q_3$ to $Q_5$ are defined the same as above.

For example, in Formulae 3-1(a) and 3-117(a), $Z_1$ and $Z_2$ may be each independently selected from:

a hydrogen, a deuterium, —F, a cyano group, a nitro group, —SF$_5$, —CH$_3$, —CD$_3$, —CD$_2$H, —CDH$_2$, —CF$_3$, —CF$_2$H, —CFH$_2$, —Si(Q$_3$)(Q$_4$)(Q$_5$), the groups of Formulae 9-1 to 9-17 above, and the groups of Formulae 10-1 to 10-30 above, wherein $Q_3$ to $Q_5$ may be each independently selected from
—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;

an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group; and an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group, each substituted with at least one of a deuterium and a C$_1$-C$_{10}$ alkyl group.

In an exemplary embodiment, in Formula 1, M may be Ir and a sum of n1 and n2 (n1+n2) may be 3; or M may be Pt and a sum of n1 and n2 (n1+n2) may be 2. Here the organometallic compound of Formula 1 may be neutral (i.e., may not include an ionic group), and L$_1$ in Formula 1 may be selected from the ligands of Formulae 2A-1 to 2A-45 above, but is not limited thereto.

In some exemplary embodiments, in Formula 1, M may be Ir and a sum of n1 and n2 (n1+n2) may be 3; or M may be Pt and a sum of n1 and n2 (n1+n2) may be 2. Here the organometallic compound of Formula 1 may be neutral (i.e., may not include an ionic group), $L_1$ in Formula 1 may be selected from the ligands of Formulae 2A-1 to 2A-45 above, and $L_2$ in Formula 1 may be selected from the ligands of Formulae 3-1 to 3-118 above (e.g., the ligands of Formulae 3-1(1) to 3-1(70) above), but they are not limited thereto.

In some other exemplary embodiments, M in Formula 1 may be Ir and a sum of n1 and n2 (n1+n2) may be 3; or M may be Pt and a sum of n1 and n2 (n1+n2) may be 2. Here the organometallic compound of Formula 1 may be neutral (i.e., may not include an ionic group), $L_1$ in Formula 1 may be selected from the ligands of Formulae 2A-1 to 2A-45 above, and $L_2$ in Formula 1 may be selected from the ligands of Formulae 3-1(a) and 3-117(a), but they are not limited thereto.

For example, the organometallic compound of Formula 1 may be one of Compounds 1 to 73 below, but is not limited thereto:

1

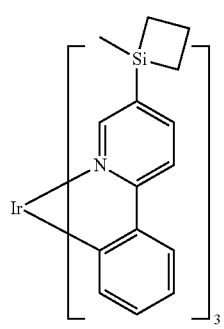

2

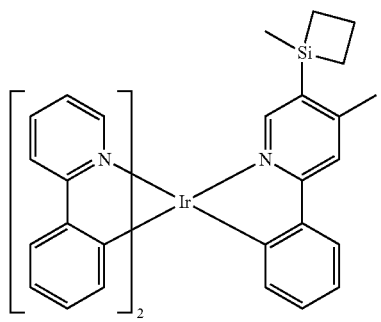

3

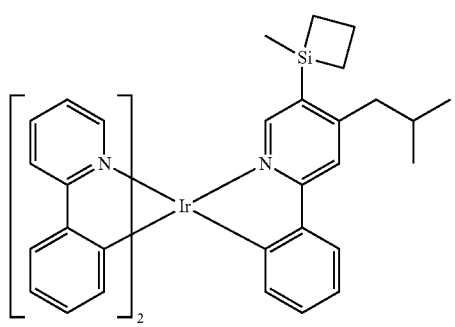

-continued

4

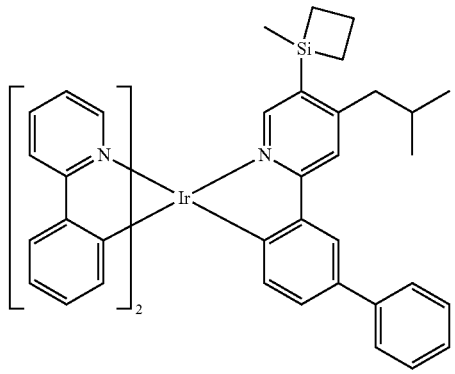

5

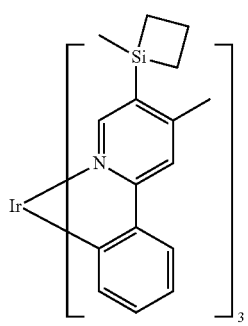

6

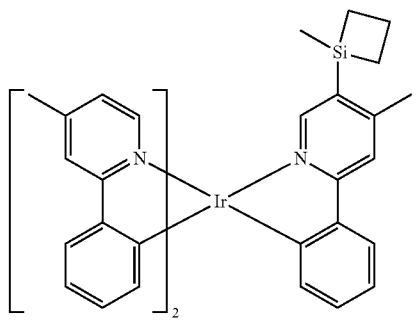

7

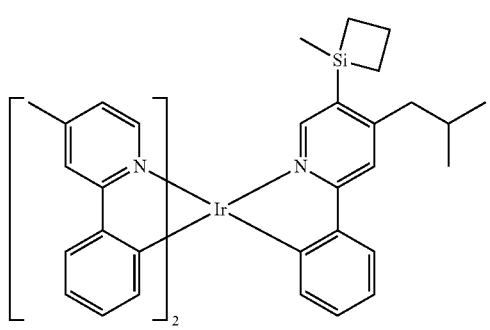

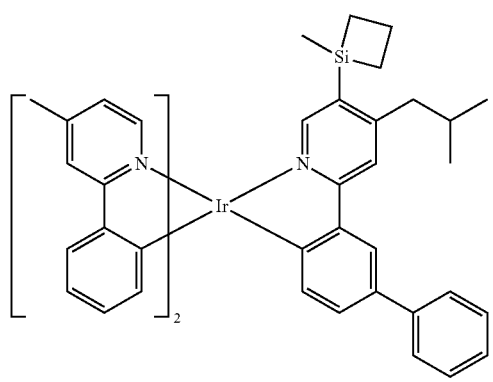
8
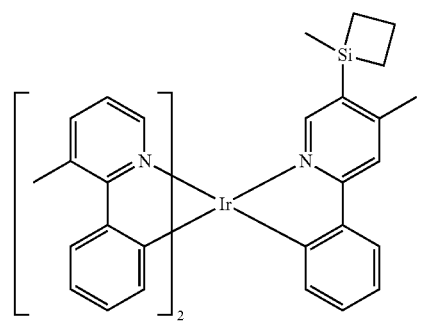
12
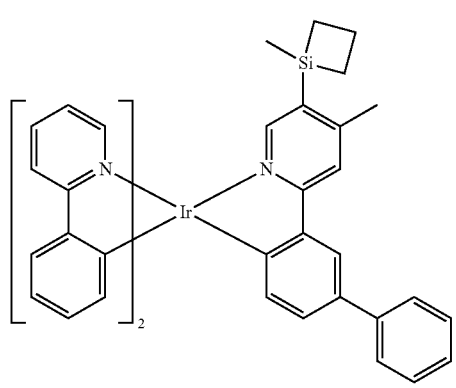
9
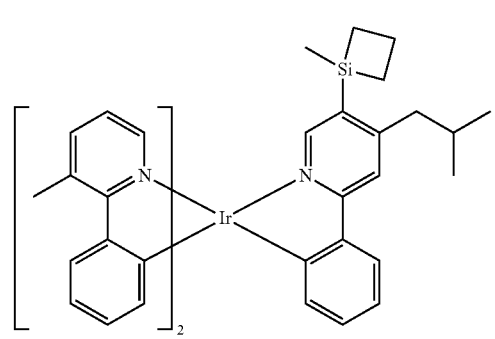
13
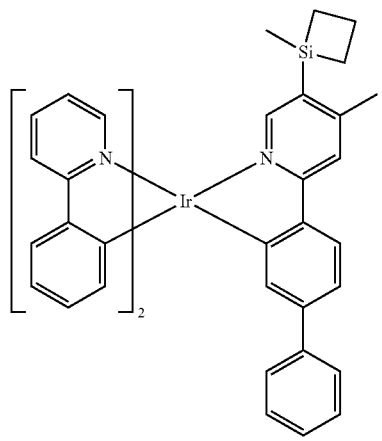
10
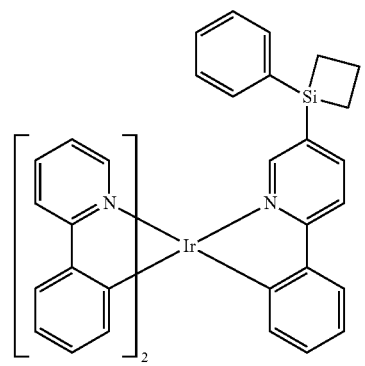
14
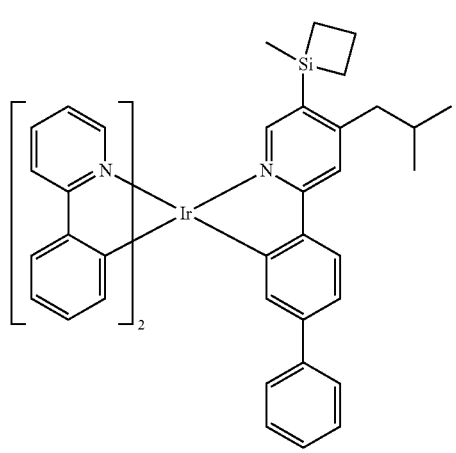
11
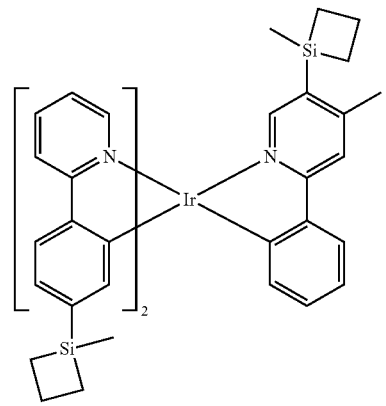
15

16
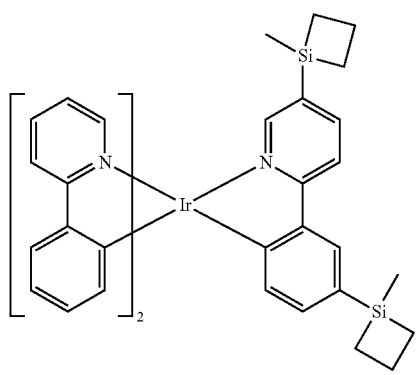
17
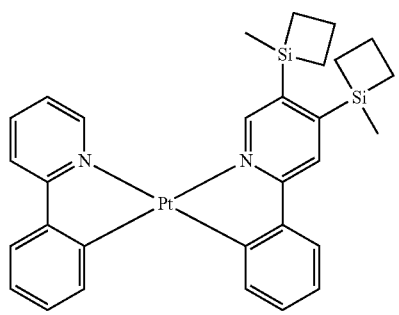
18
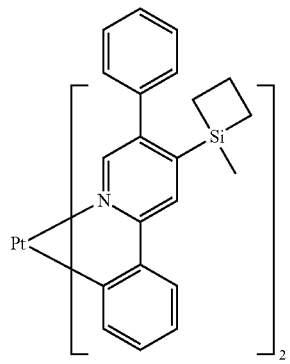
19
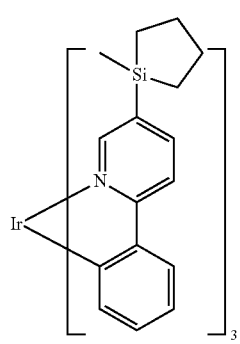
20
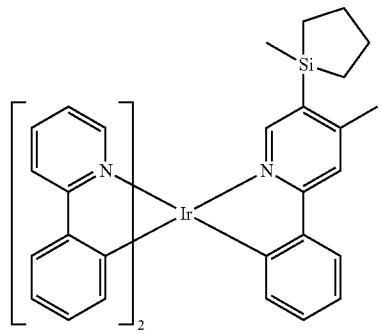
21
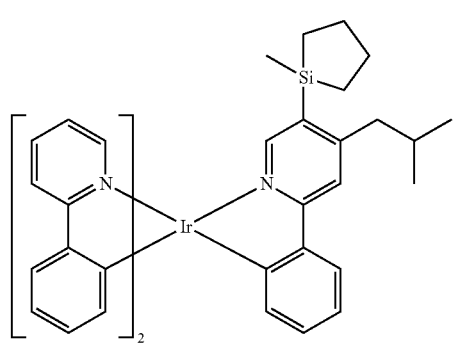
22
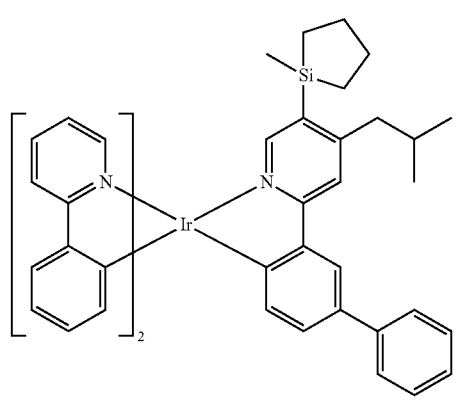
23

24
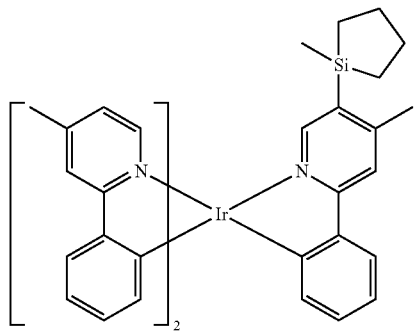
25
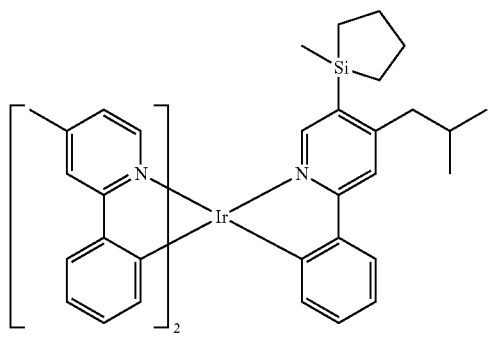
26
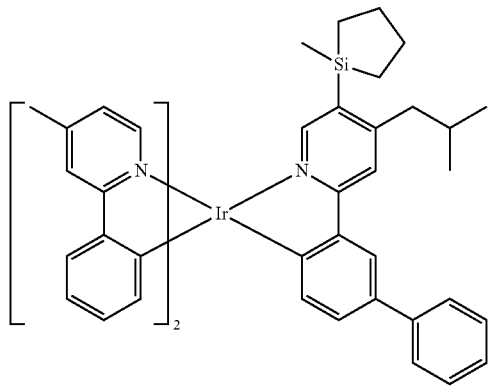
27
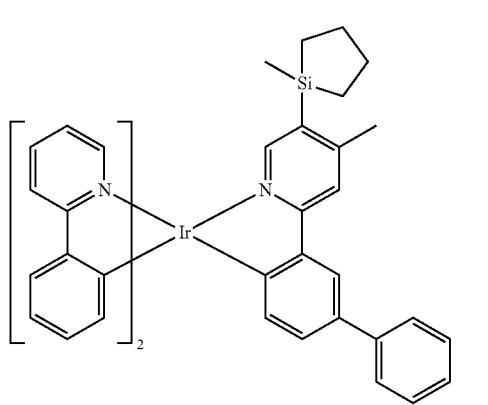
28
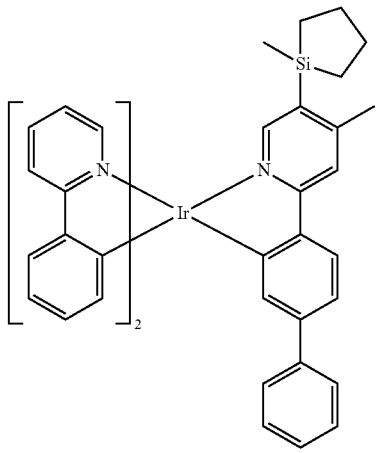
29
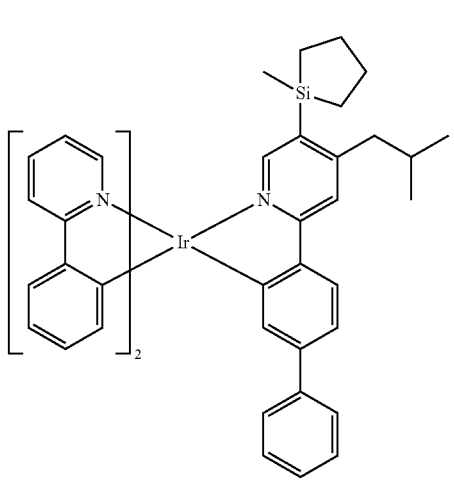
30
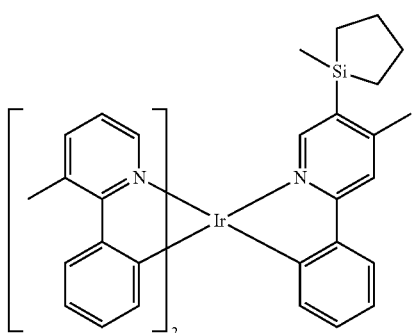
31
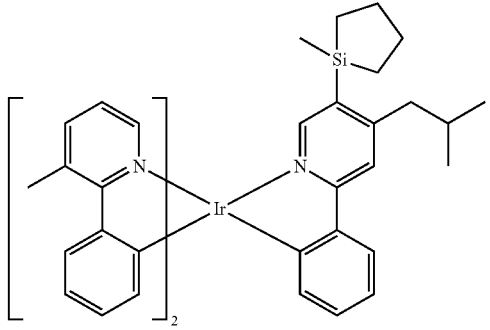

| 32 | 36 |
|---|---|
| 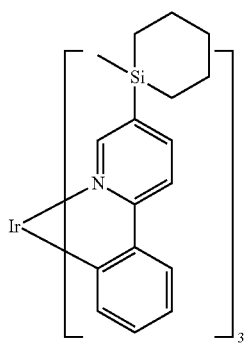 | 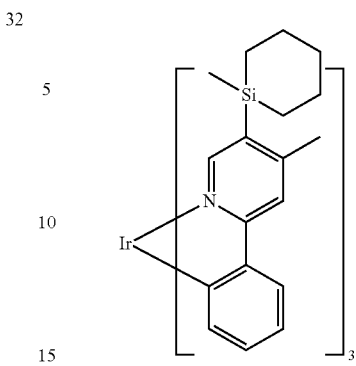 |
| 33 | 37 |
| 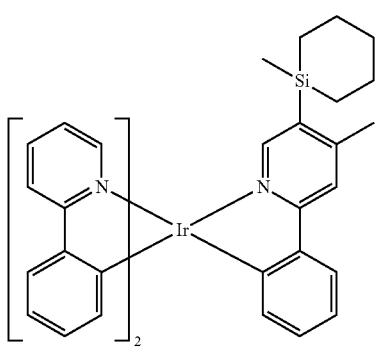 | 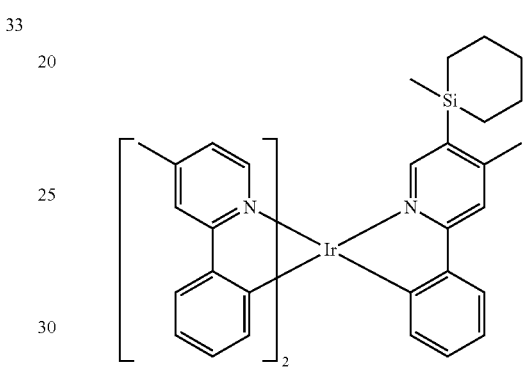 |
| 34 | 38 |
| 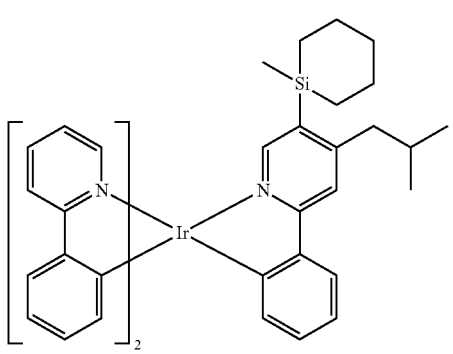 | 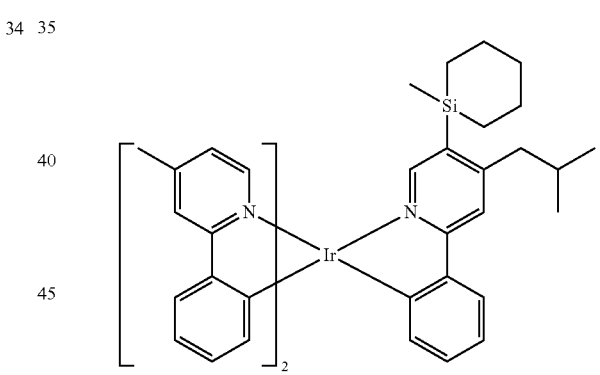 |
| 35 | 39 |
| 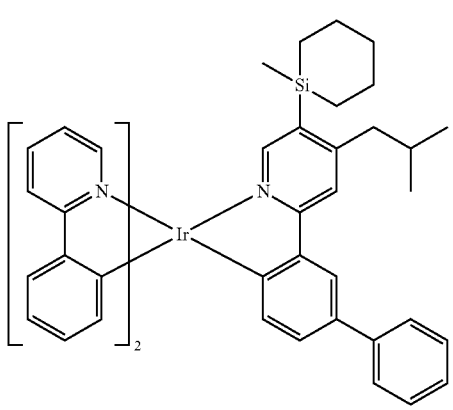 | 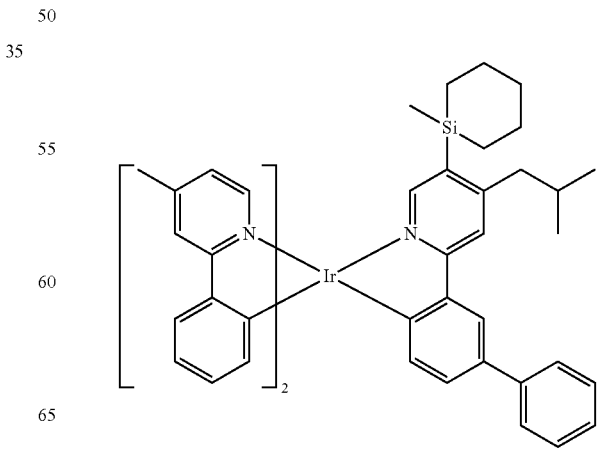 |

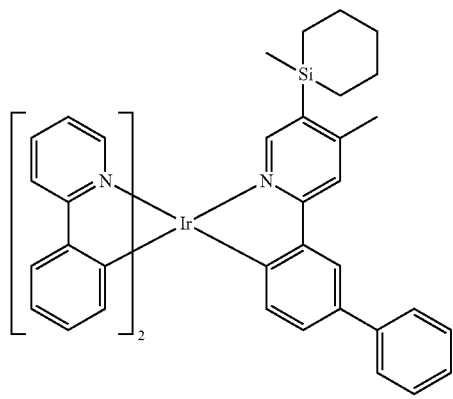
40
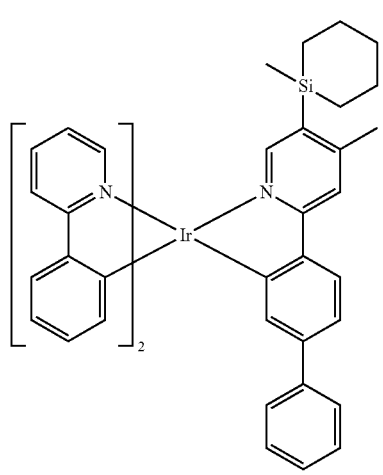
41
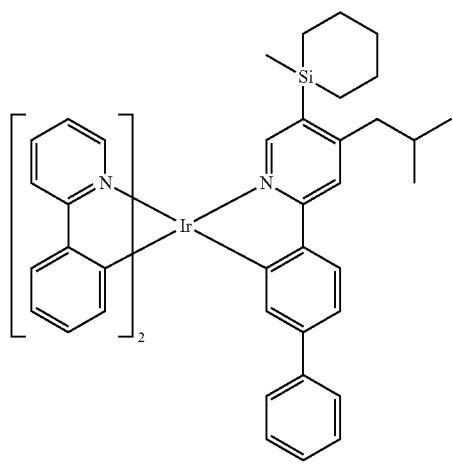
42
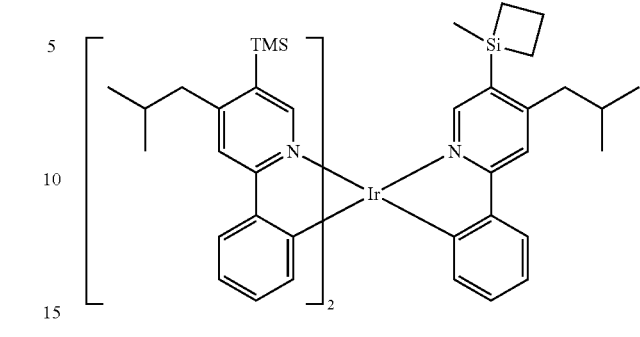
43
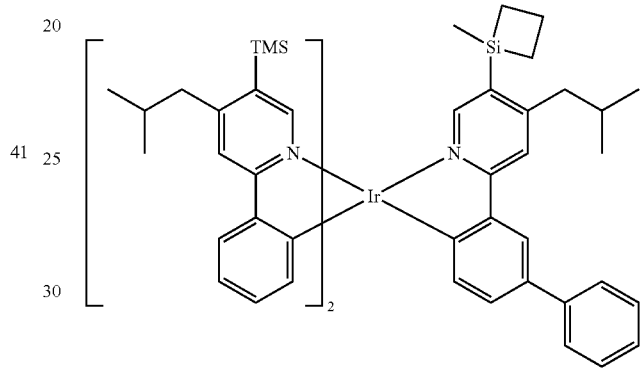
44
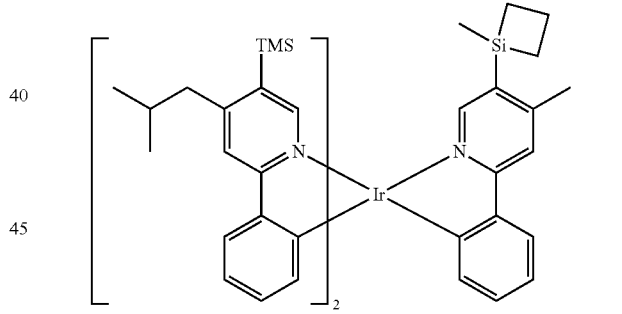
45
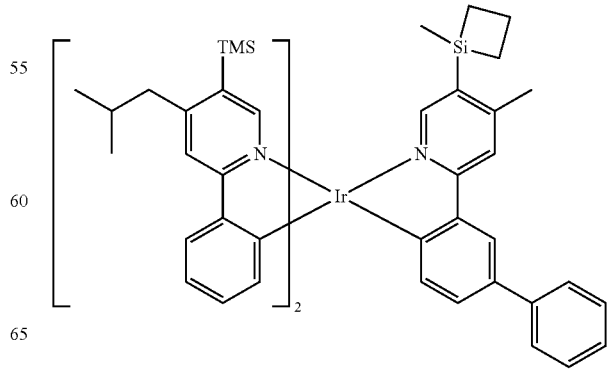
46

47
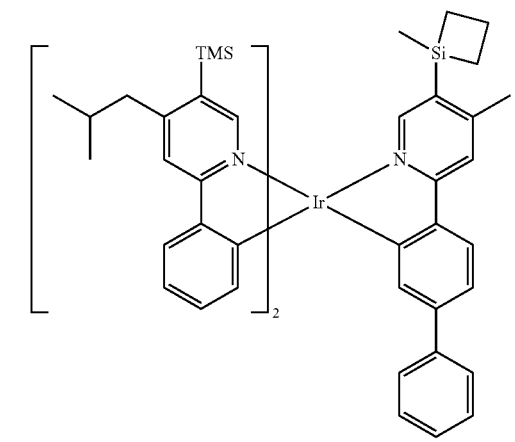
48
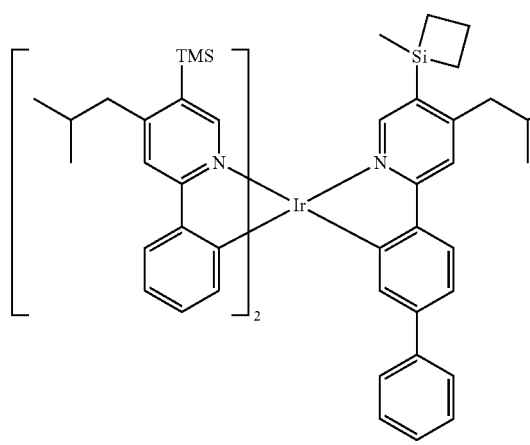
49
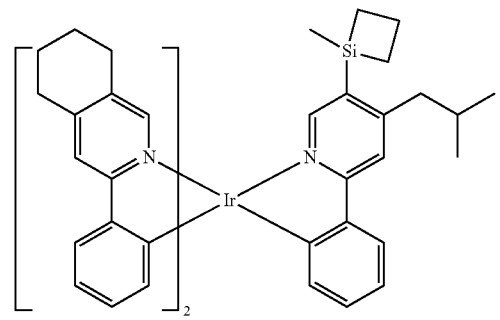
50
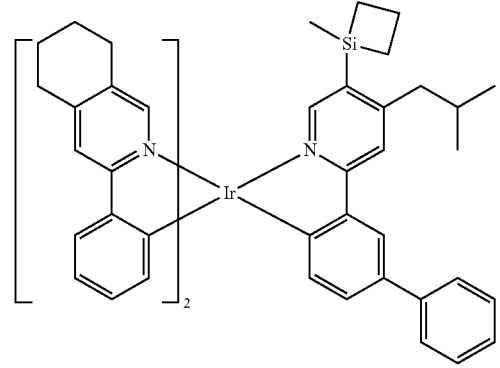
51
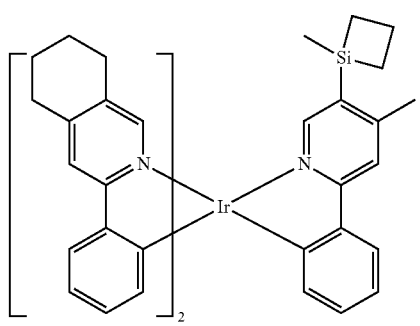
52
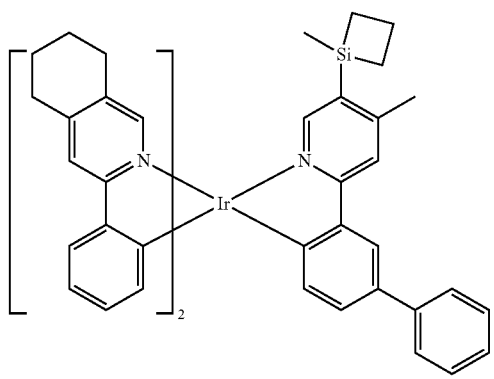
53
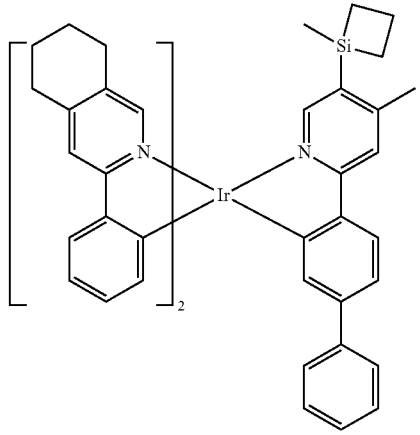
54
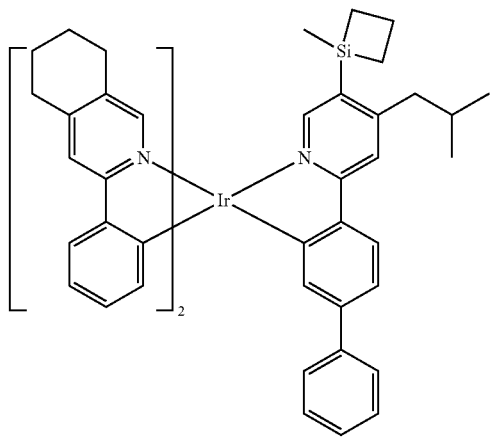

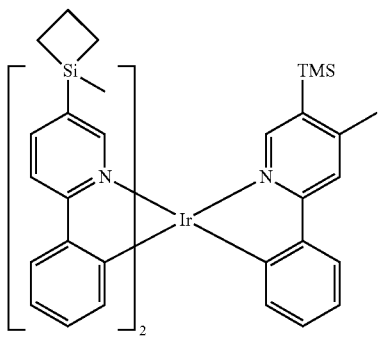
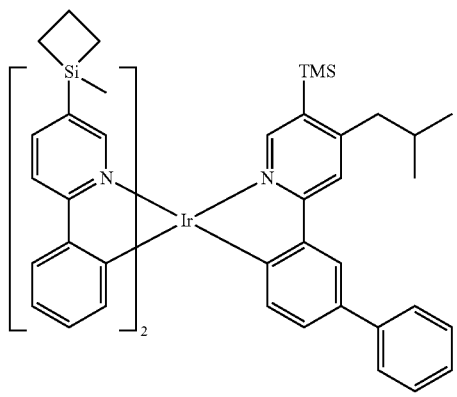
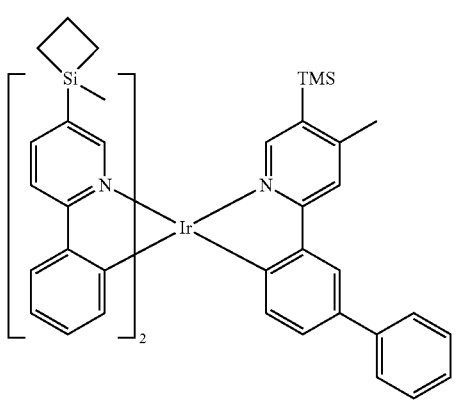
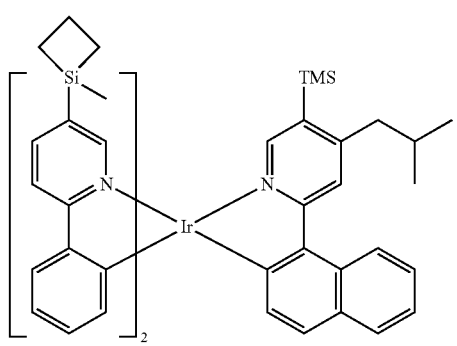
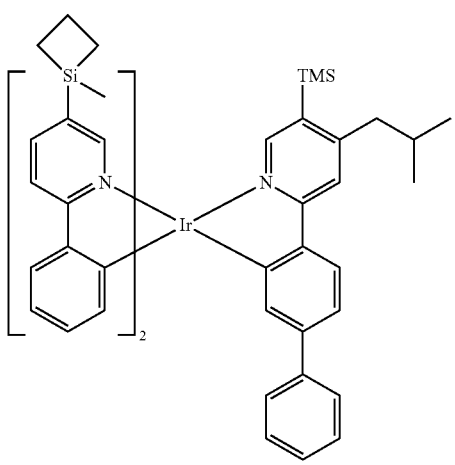
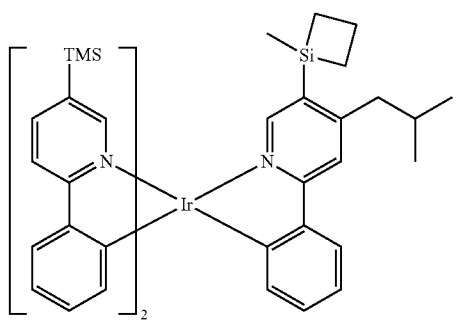
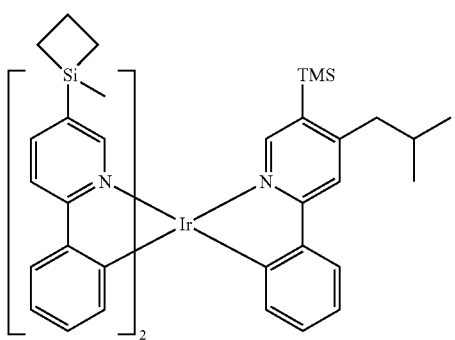
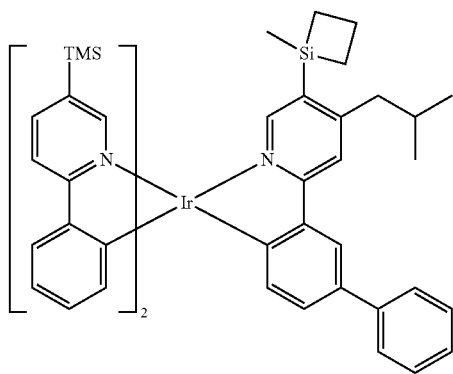

93
-continued
63
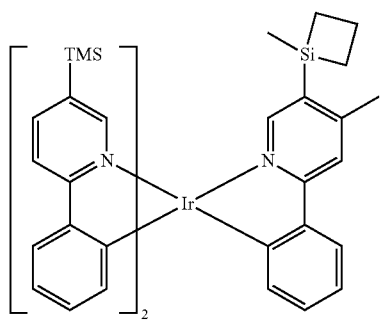
64
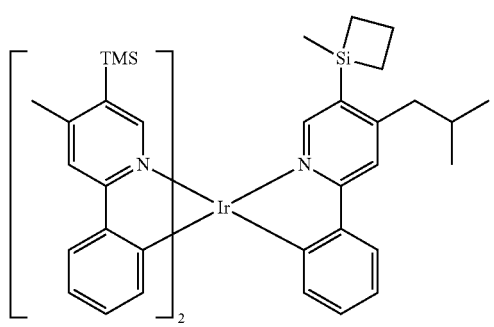
65
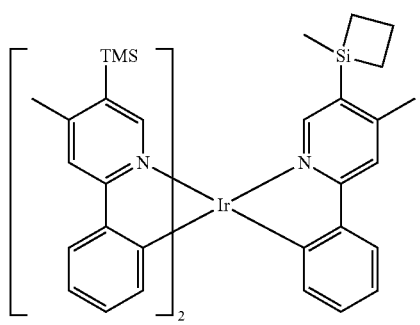
66
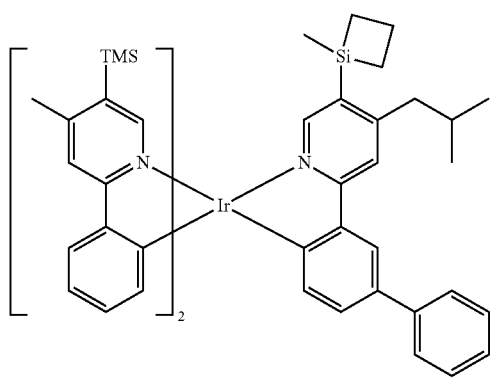
94
-continued
67
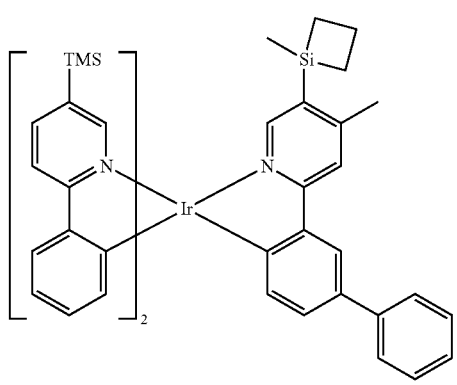
68
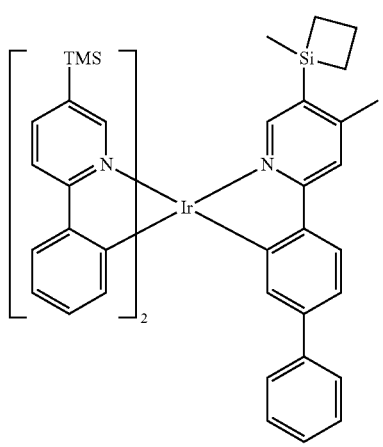
69
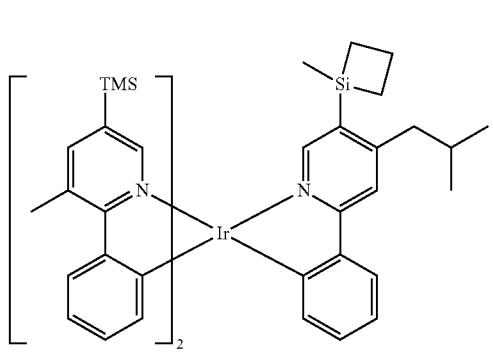
70
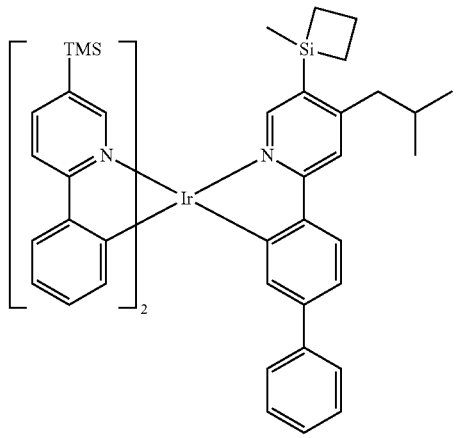

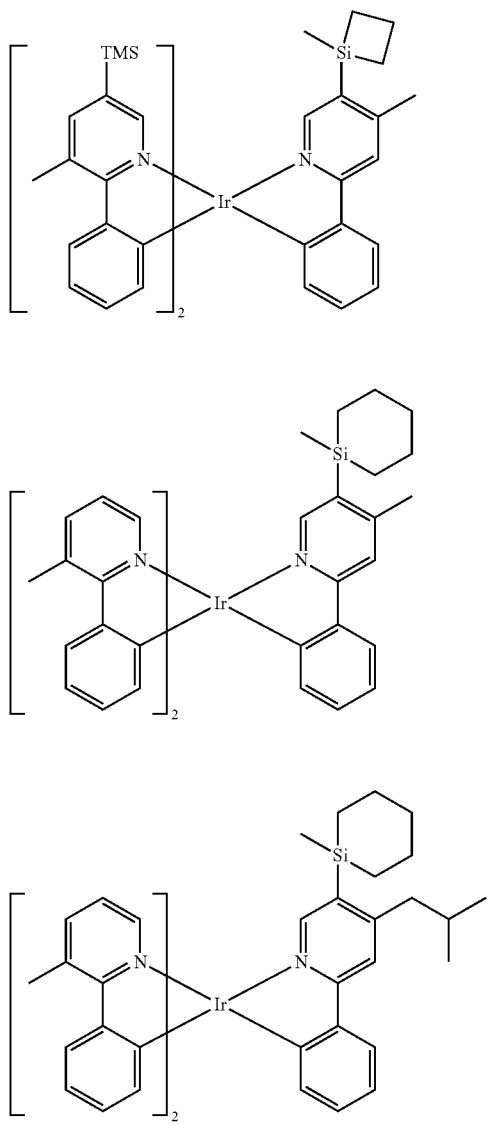

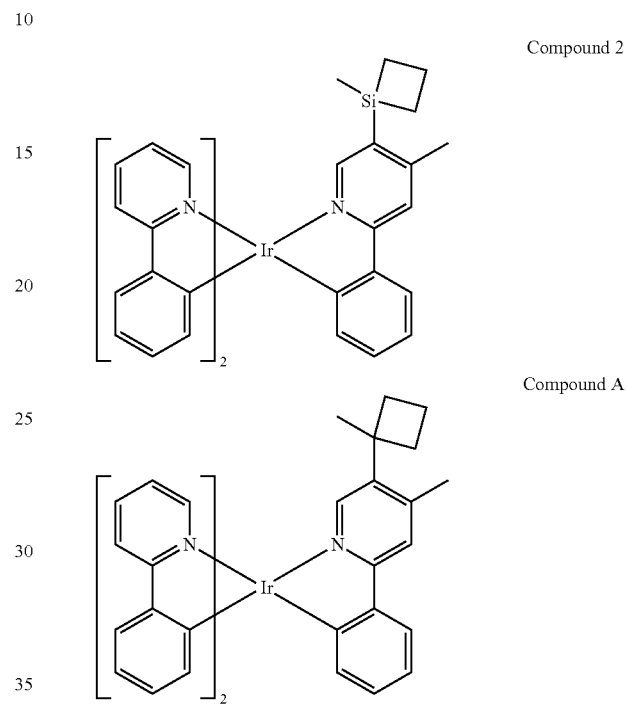

TABLE 1

| Compound No. | HOMO energy level (eV) | LUMO energy level (eV) | $T_1$ energy level (eV) |
|---|---|---|---|
| Compound 2 | −4.827 | −1.254 | 2.576 |
| Compound A | −4.777 | −1.141 | 2.621 |

In the organometallic compound of Formula 1, $L_1$ may be the ligand of Formula 2A, $R_{13}$ and $R_{14}$ in Formula 2A may be each independently the group of Formula 2B, and a sum of b3 and b4 (b3+b4) may be 1 or more. Thus, the ligand of Formula 2A essentially includes, as a substituent, at least group of Formula 2B. Accordingly, the organometallic compound of Formula 1 may have relatively low highest occupied molecular orbital (HOMO) and the lowest unoccupied molecular orbital (LUMO) energy levels (i.e., HOMO and LUMO energy levels having relatively high absolute values). Thus, an organic light-emitting device including the organometallic compound of Formula 1 may have long lifespan characteristics.

For example, HOMO, LUMO, and triplet (Ti) energy levels in regard to Compound 2 and Compound A are evaluated according to the density functional theory (EFT) using Gaussian software (geometry optimized with B3LYP, 6-31G(d,p)), and the results are shown in Table 1 below.

Referring to Table 1, it is confirmed that the organometallic compound of Formula 1 has HOMO and LUMO energy levels that are lower than those of Compound A.

The method of synthesizing the organometallic compound of Formula 1 may be understood by one of ordinary skill in the art by referring to Synthesis Examples described below.

Thus, the organometallic compound of Formula 1 may be suitable as a dopant in the organic layer, e.g., the emission layer of the organic layer, of the organic light-emitting device. In an exemplary embodiment, there is provided an organic light-emitting device including:

a first electrode;
a second electrode; and
an organic layer disposed between the first electrode and the second electrode,
wherein the organic layer includes an emission layer and at least one of the organometallic compounds of Formula 1.

When an organic light-emitting device includes an organic layer including the organometallic compound of Formula 1, the organic light-emitting device may have low driving voltage, high efficiency, high electricity, high quantum efficiency, long lifespan, and excellent color purity.

The organometallic compound of Formula 1 may be used between a pair of electrodes of the organic light-emitting device. For example, the organometallic compound of Formula 1 may be included in the emission layer. Here, the organometallic compound may serve as a dopant, and the emission layer may further include a host (i.e., an amount of the organometallic compound of Formula 1 may be smaller than an amount of the host).

The expression "(an organic layer) includes at least one of the organometallic compounds" as used herein may be applicable when "(an organic layer) includes one organometallic compound of Formula 1 or two or more different organometallic compound of Formula 1".

For example, the organic layer may include, as the organometallic compound, only Compound 2. In this regard, Compound 2 may be included in the emission layer of the organic light-emitting device. Alternatively, the organic layer may include, as the organometallic compound, Compound 2 and Compound 3. In this regard, Compound 2 and Compound 3 may be included in an identical layer (e.g., both Compound 2 and Compound 3 all may be included in the emission layer).

The first electrode may be an anode, which is a hole injection electrode, and the second electrode may be a cathode, which is an electron injection electrode. Alternatively, the first electrode may be a cathode, which is an electron injection electrode, and the second electrode may be an anode, which is a hole injection electrode.

For example, the first electrode may be an anode, the second electrode may be a cathode, and the organic layer may include:

i) a hole transport region that is formed between the first electrode and the emission layer, wherein the hole transport electron includes at least one of a hole injection layer, a hole transport layer, and an electron blocking layer; and ii) an electron transport region that is formed between the emission layer and the second electrode, wherein the electron transport region includes at least one of a hole blocking layer, an electron transport layer, and an electron injection layer.

The term "organic layer" as used herein refers to a single layer and/or a plurality of layers disposed between the first electrode and the second electrode of the organic light-emitting device. The "organic layer" may include not only an organic compound, but also an organic metal complex including metal.

The FIGURE illustrates a schematic cross-sectional view of an organic light-emitting device 10 according to an exemplary embodiment. Hereinafter, a structure of an organic light-emitting device according to an exemplary embodiment and a method of manufacturing an organic light-emitting device according to an exemplary embodiment will be described in connection with the FIGURE. The organic light-emitting device 10 has a structure of a first electrode 11, an organic layer 15, and a second electrode 19 that are sequentially stacked in the stated order.

A substrate may be additionally disposed under the first electrode 11 or above the second electrode 19. For use as the substrate, any substrate that is used in general organic light-emitting devices may be used, and the substrate may be a glass substrate or a transparent plastic substrate, each with excellent mechanical strength, thermal stability, transparency, surface smoothness, ease of handling, and water repellency.

The first electrode 11 may be formed by, for example, depositing or sputtering a material for forming the first electrode 11 on the substrate. When the first electrode 11 is an anode, the material for forming the first electrode 11 may be selected from materials with a high work function to facilitate hole injection. The first electrode 11 may be a reflective electrode, a semi-transmissive electrode, or a transmissive electrode. The material for forming the first electrode 11 may be an indium tin oxide (ITO), indium zinc oxide (IZO), tin oxide (SnO2), or zinc oxide (ZnO), each with transparency and excellent conductivity. Alternatively, the material for forming the first electrode 11 may be a metal, such as magnesium (Mg), aluminum (Al), aluminum-lithium (Al—Li), calcium (Ca), magnesium-indium (Mg—In), and magnesium-silver (Mg—Ag).

The first electrode 11 may have a single-layer structure or a multi-layer structure including a plurality of layers. For example, the first electrode 11 may have a triple-layered structure of ITO/Ag/ITO, but the structure of the first electrode 11 is not limited thereto.

An organic layer 15 may be disposed on top of the first electrode 11.

The organic layer 15 may include the hole transport region; the emission layer; and the electron transport region.

The hole transport region may be disposed between the first electrode 11 and the emission layer.

The hole transport region may include at least one of a hole injection layer, a hole transport layer, an electron blocking layer, and a buffer layer.

The hole transport region may include only a hole injection layer or only a hole transport layer. Alternatively, the hole transport region may include a structure of hole injection layer/hole transport layer or a structure of hole injection layer/hole transport layer/electron blocking layer, each of which layers are sequentially stacked in the stated order from the first electrode 11.

When the hole transport region includes a hole injection layer (HIL), the hole injection layer may be formed on the first electrode 11 by using various methods, such as vacuum deposition, spin coating, casting, and Langmuir-Blodgett (LB) deposition method.

When the HIL is formed by vacuum deposition, deposition conditions may vary according to a compound used to form the HIL, a structure of the HIL, and thermal characteristics. For example, the deposition conditions may include a deposition temperature in a range of about 100° C. to about 500° C., a vacuum pressure in a range of about $10^{-8}$ torr to about $10^{-3}$ torr, and a deposition rate in a range of about 0.01 Angstroms per second (Å/sec) about 100 Å/sec, but they are not limited thereto.

When the HIL is formed by spin coating, coating conditions may vary according to a compound used to form the HIL, a structure of the HIL, and thermal characteristics. For example, the coating conditions include a coating speed in a range of about 2,000 revolutions per minute (rpm) to about 5,000 rpm, and a temperature solvent at which a heat treatment is performed to remove a solvent may be in a range of about 80° C. to about 200° C., but they are not limited thereto.

Conditions for forming the hole transport layer and the electron blocking layer may be referred to those for forming the HIL.

The hole transport region may include at least one selected from, e.g., m-MTDATA, TDATA, 2-TNATA, NPB, β-NPB, TPD, Spiro-TPD, Spiro-NPB, methylated-NPB, TAPC, HMTPD, 4,4',4"-tris(N-carbazolyl)triphenylamine (TCTA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), polyaniline/poly(4-styrenesulfonate) (PANI/PSS), a compound represented by Formula 201 below, and a compound represented by Formula 202 below:

-continued
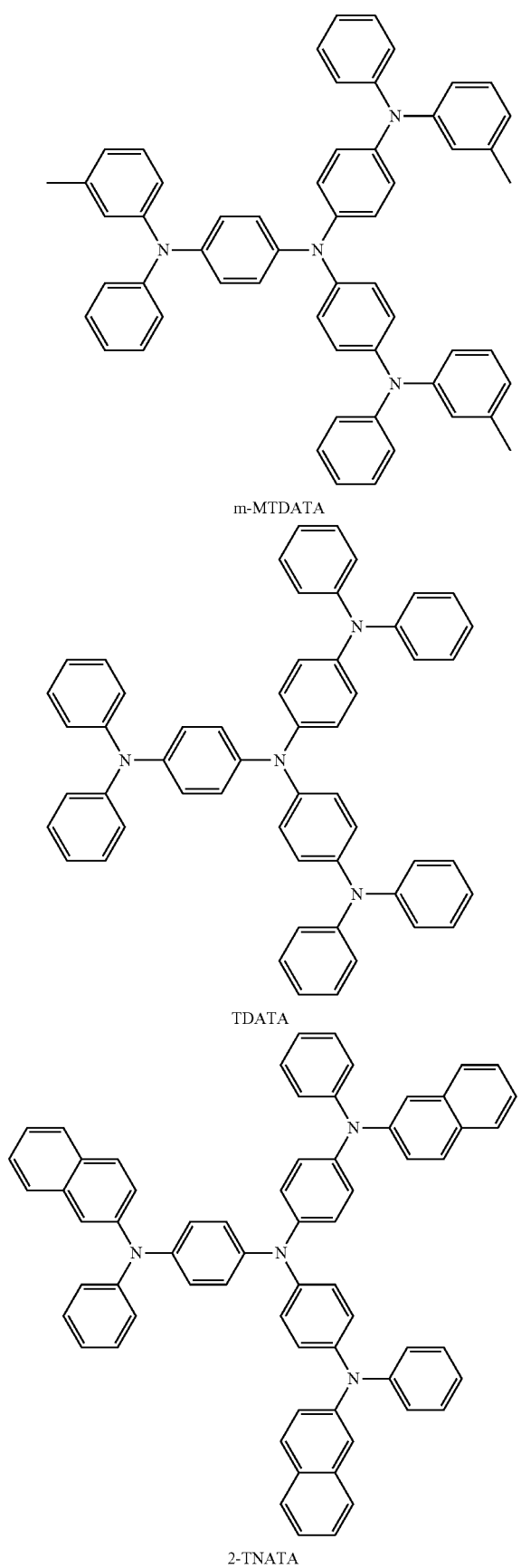
m-MTDATA
TDATA
2-TNATA
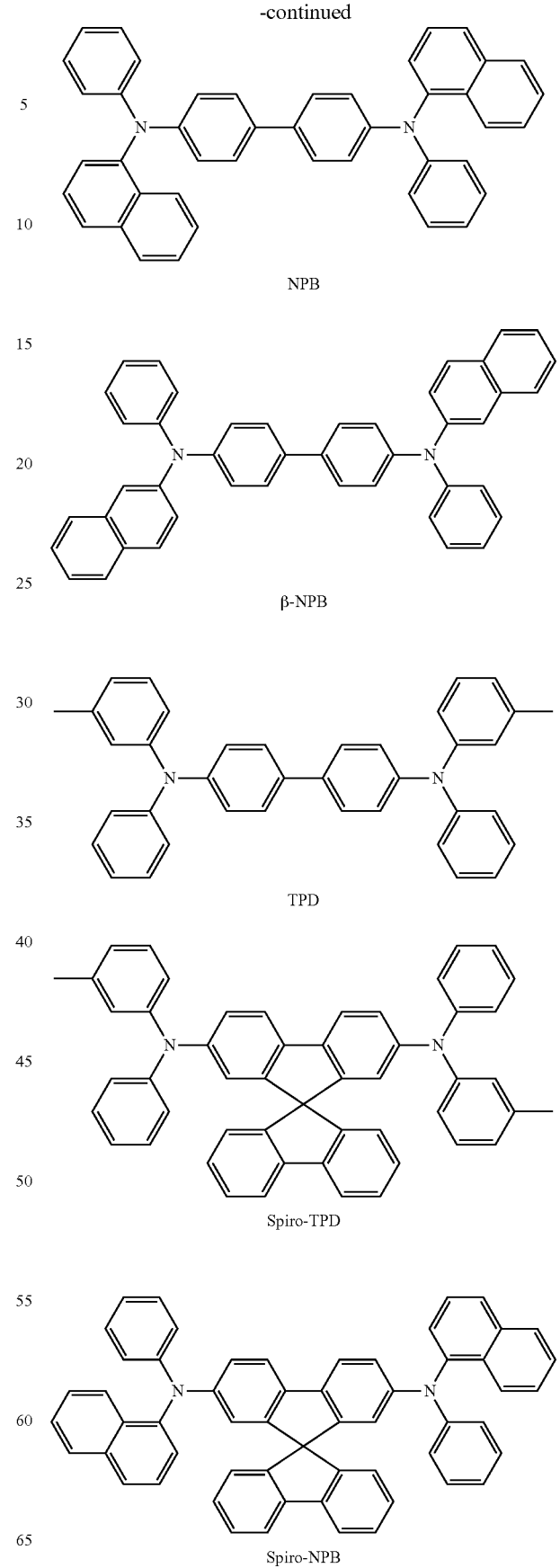
NPB
β-NPB
TPD
Spiro-TPD
Spiro-NPB

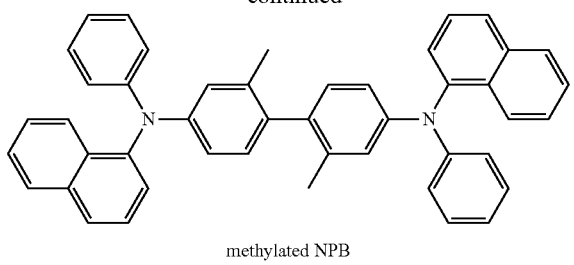

methylated NPB

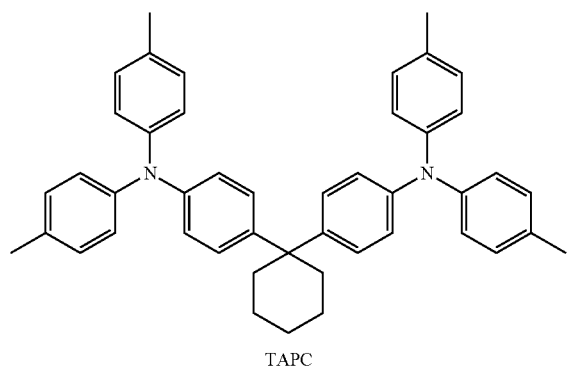

TAPC

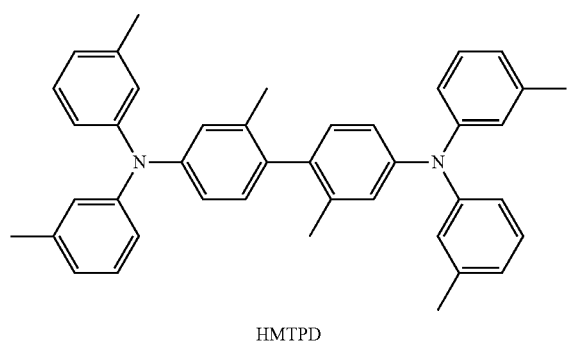

HMTPD

Formula 201

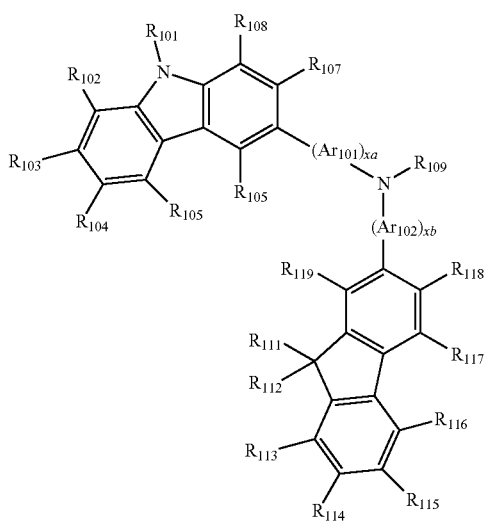

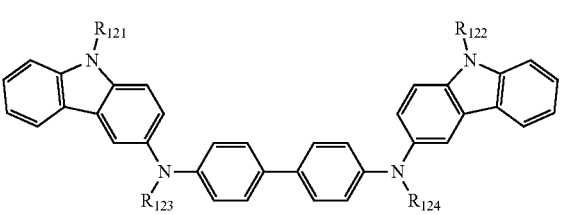

Formula 202

In Formula 201, $Ar_{101}$ and $Ar_{102}$ may be each independently selected from:

a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_1$-$C_{10}$ heterocycloalkyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

In Formula 201, xa and xb may be each independently an integer selected from 0 to 5, or may be 0, 1, or 2. For example, in Formula 201, xa may be 1 and xb may be 0, but they are not limited thereto.

In Formulae 201 and 202, $R_{101}$ to $R_{108}$, $R_{111}$ to $R_{119}$, and $R_{121}$ to $R_{124}$ may be each independently selected from:

a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (e.g., a methyl group, an ethyl group, a propyl group, a butyl group, a pentyl group, and a hexyl group), and a $C_1$-$C_{10}$ alkoxy group (e.g., a methoxy group, an ethoxy group, a propoxy group, a butoxy group, and a pentoxy group);

a $C_1$-$C_{10}$ alkyl group and a $C_1$-$C_{10}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, an anthracenyl group, a fluorenyl group, and a pyrenyl group; and a phenyl group, a naphthyl group, an anthracenyl group, a fluorenyl group, and a pyrenyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group.

In Formula 201, $R_{109}$ may be selected from: a phenyl group, a naphthyl group, an anthracenyl group, and a pyridinyl group; and a phenyl group, a naphthyl group, an anthracenyl group, and a pyridinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, and a pyridinyl group.

In an exemplary embodiment, the compound of Formula 201 may be represented by Formula 201A below, but is not limited thereto:

Formula 201A

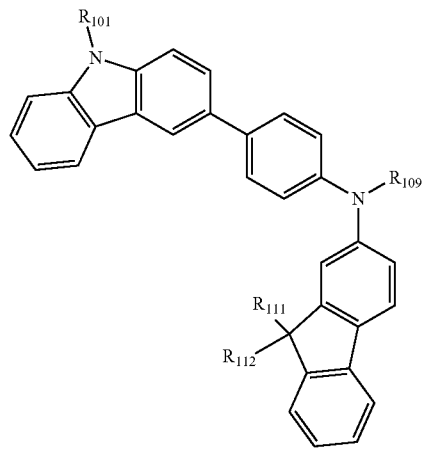

In Formula 201A, $R_{101}$, $R_{111}$, $R_{112}$, and $R_{109}$ may be understood by referring to the descriptions provided herein.

For example, the compound of Formula 201 and the compound of Formula 202 may include Compounds HT1 to HT20 below, but they are not limited thereto:

HT1

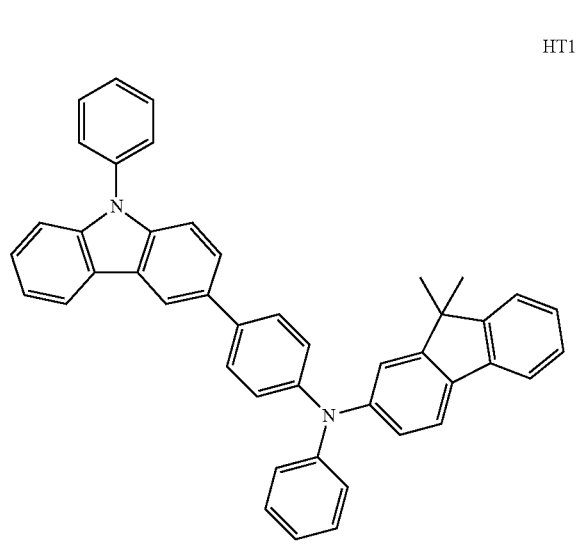

HT2

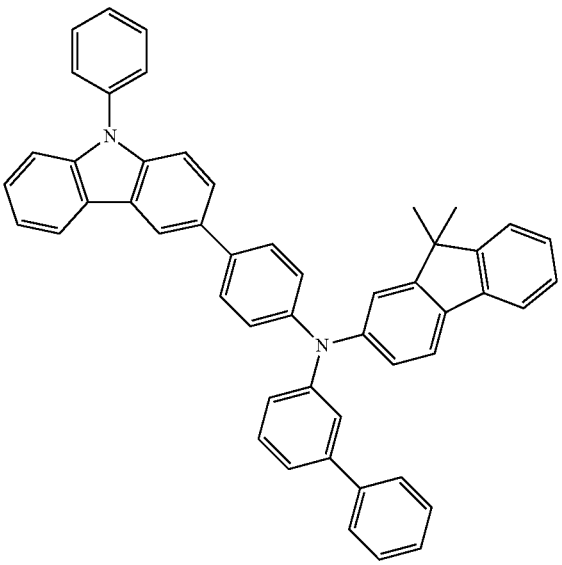

HT3

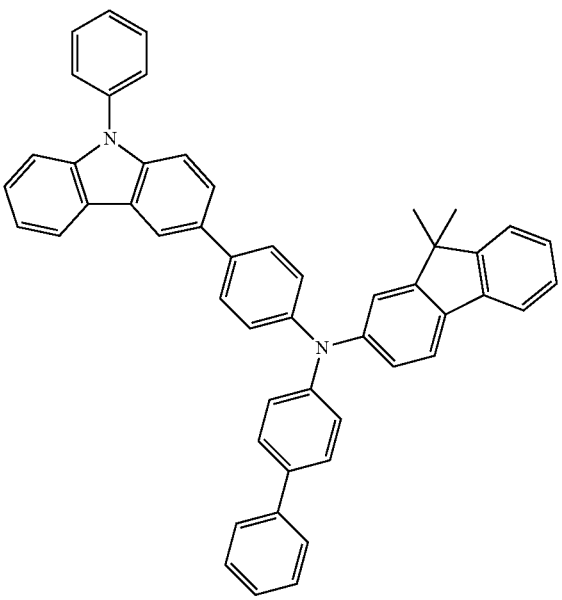

HT4
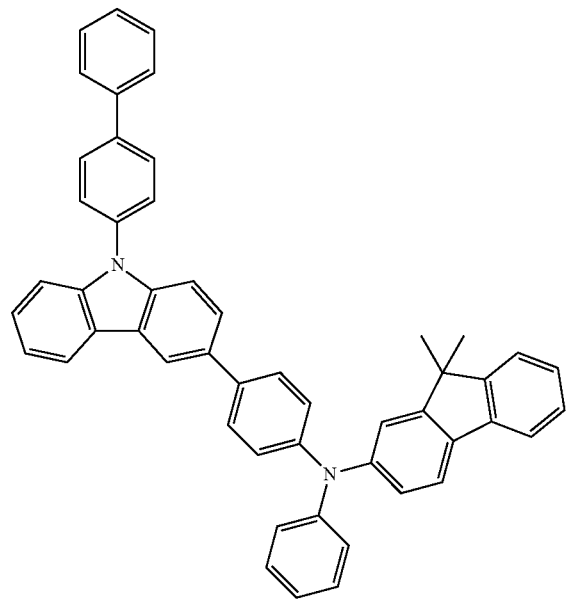
HT6
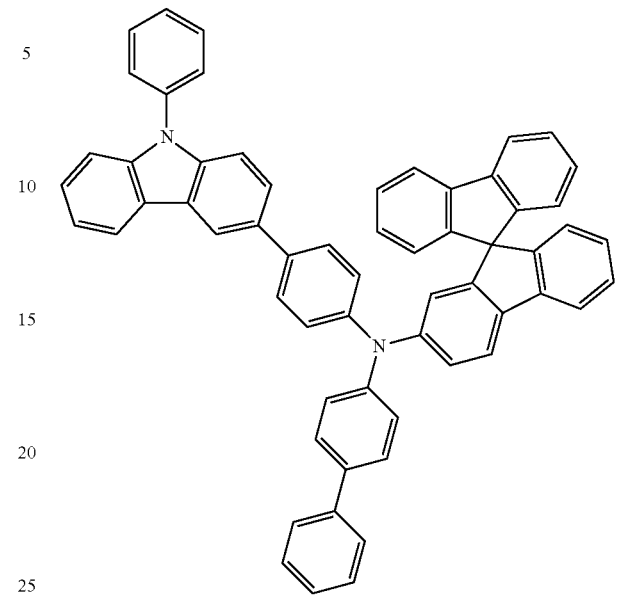
HT5
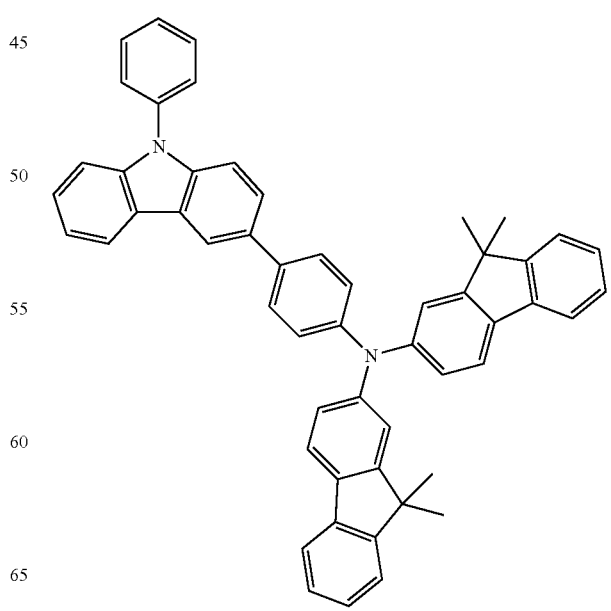
HT7

HT8
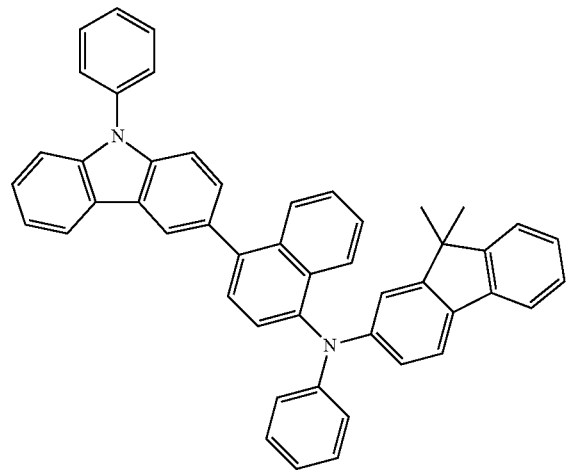
HT9
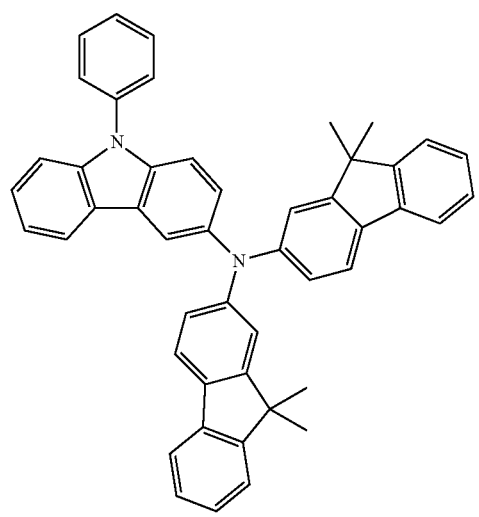
HT10
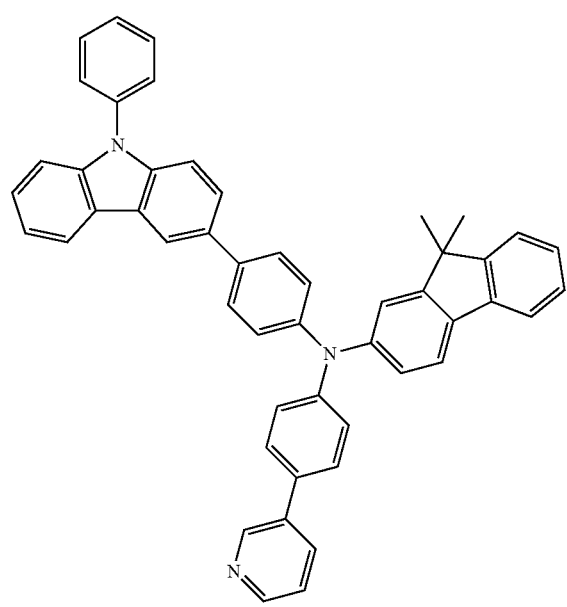
HT11
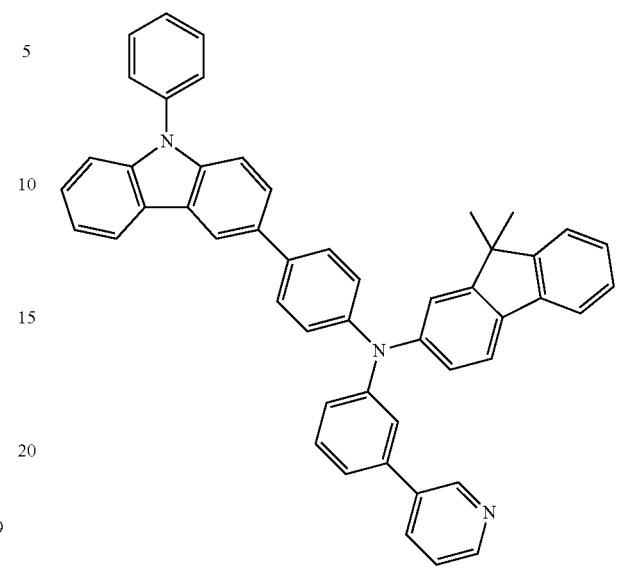
HT12
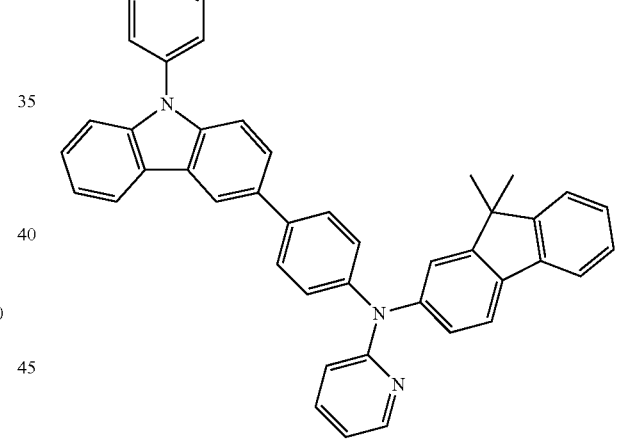
HT13
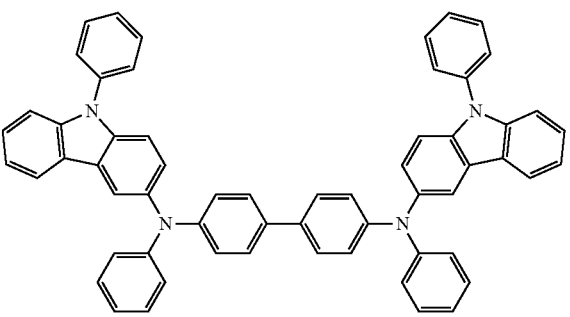

HT14
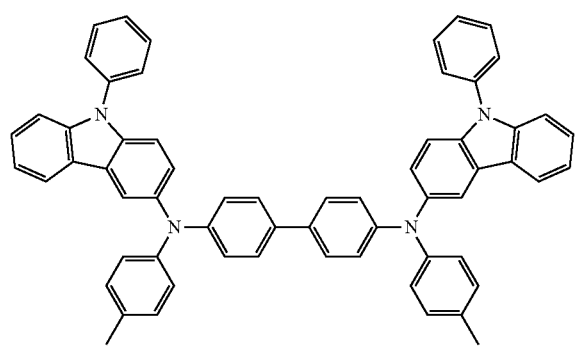

HT15
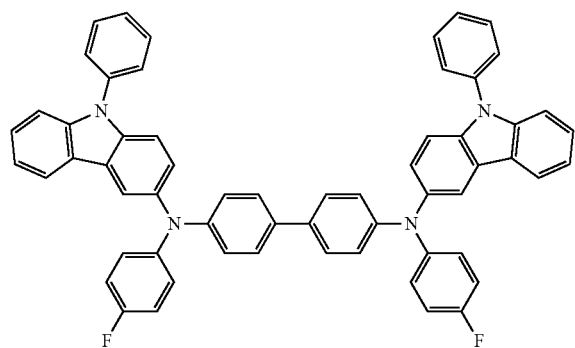

HT16
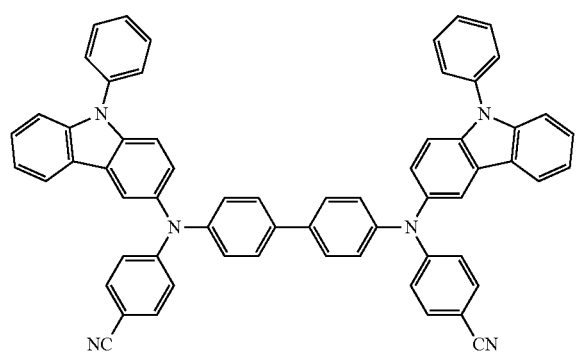

HT17
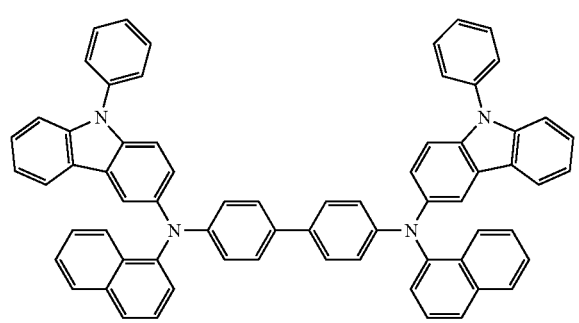

HT18
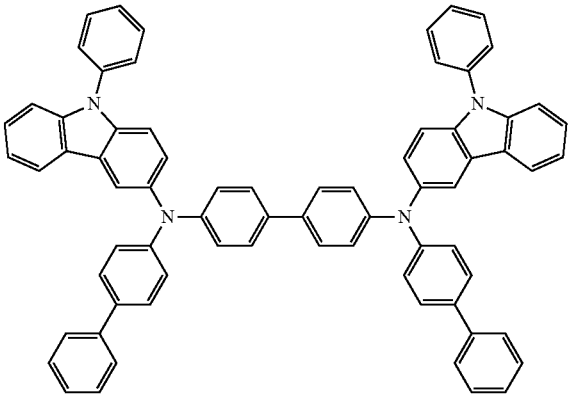

HT19
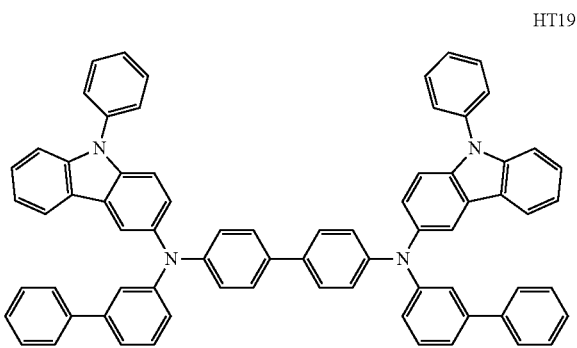

HT20
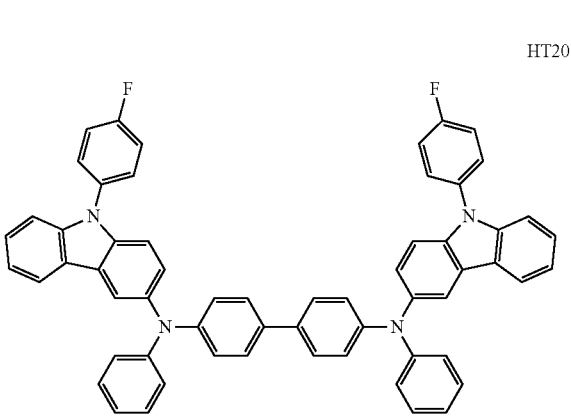 [SMILES: Fc1ccc(-n2c3ccccc3c3cc(N(c4ccccc4)c4ccc(-c5ccc(N(c6ccccc6)c6ccc7c(c6)c6ccccc6n7-c6ccc(F)cc6)cc5)cc4)ccc32)cc1]

A thickness of the hole transport region may be in a range of about 100 Å to about 10,000 Å, e.g., about 100 Å to about 1,000 Å. When the hole transport region includes both an HIL and an HTL, a thickness of the HIL may be in a range of about 100 Å to about 10,000 Å, e.g., about 100 Å to about 1,000 Å, and a thickness of the HTL may be in a range of about 50 Å to about 2,000 Å, e.g., about 100 Å to about 1,500 Å. When the thicknesses of the hole transport region, the HIL, and the HTL are within these ranges, satisfactory hole transporting characteristics may be obtained without a substantial increase in driving voltage.

In addition to the materials described above, the hole transport region may further include a charge-generation material for the improvement of conductive characteristics.

The charge-generation material may be homogeneously or non-homogeneously dispersed in the hole transport region.

The charge-generation material may be, e.g., a p-dopant. The p-dopant may be one of a quinone derivative, a metal oxide, and a cyano group-containing compound, but is not limited thereto. Non-limiting examples of the p-dopant are a quinone derivative such as tetracyanoquinonedimethane (TCNQ) or 2,3,5,6-tetrafluoro-tetracyano-1,4-benzoquinonedimethane (F4-TCNQ); a metal oxide such as a tungsten oxide or a molybdenum oxide; and a cyano group-containing compound such as Compound HT-D1 below, but are not limited thereto.

Compound HT-D1

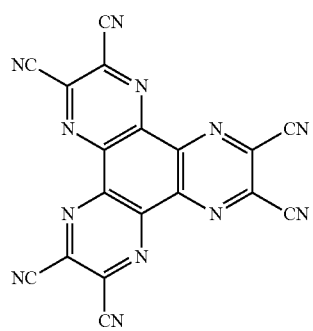

F4-TCNQ

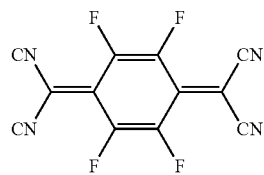

The hole transport region may further include a buffer layer.

The buffer layer may compensate for an optical resonance distance according to a wavelength of light emitted from the emission layer. Thus, a light-emission efficiency of a formed organic light-emitting device may be improved.

An emission layer (EML) may be disposed on top of the hole transport region by using various methods, such as vacuum deposition, spin coating, casting, and LB deposition method. When the EML is formed by vacuum deposition and spin coating, deposition and coating conditions for forming the EML may be determined by referring to the deposition and coating conditions for forming the HIL.

When the hole transport region includes an electron blocking layer (EBL), a material for forming the EBL may be selected from the materials for forming the hole transport region and host materials shown below, but is not limited thereto. For example, when the hole transport region includes the EBL, mCP described below may be used as a material for forming the EBL.

The EML may include a host and a dopant, and the dopant may include the organometallic compound of Formula 1.

The host may include at least one selected from TPBi, TBADN, AND (also referred to as "DNA"), CBP, CDBP, TCP, mCP, and Compounds H50 and H51 below:

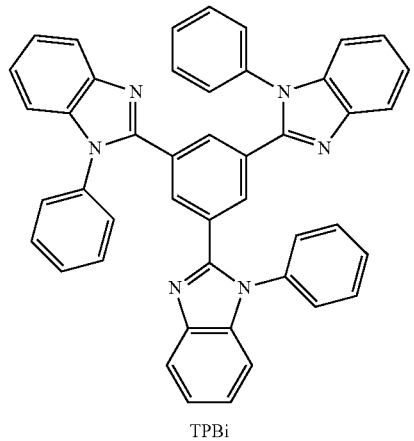

TPBi

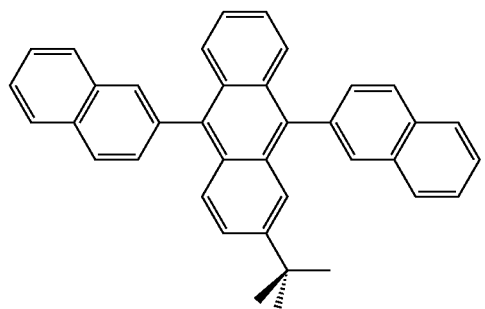

TBADN

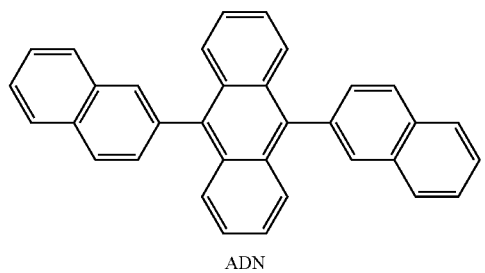

ADN

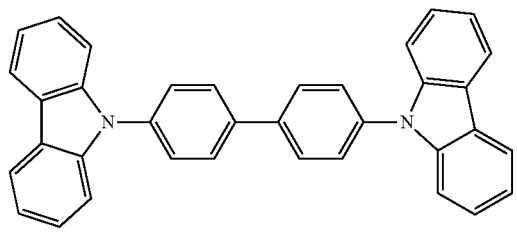

CBP

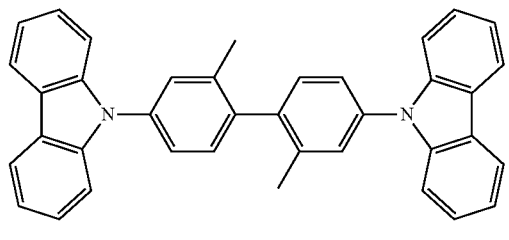

CDBP

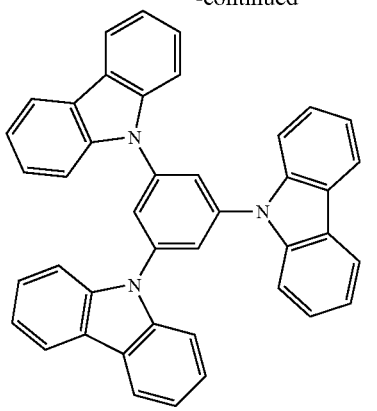

TCP

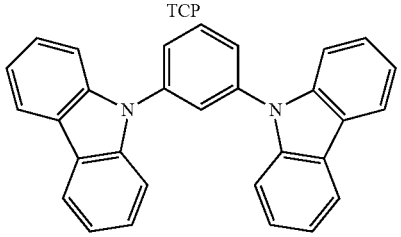

mCP

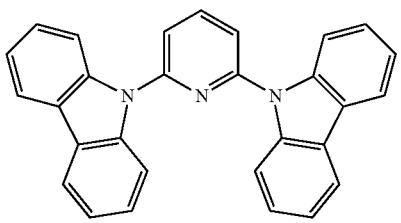

Compound H50

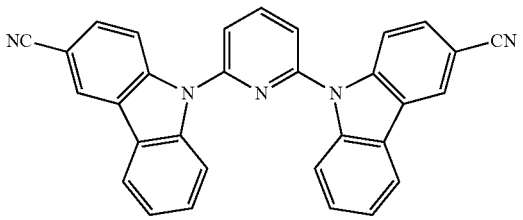

Compound H51

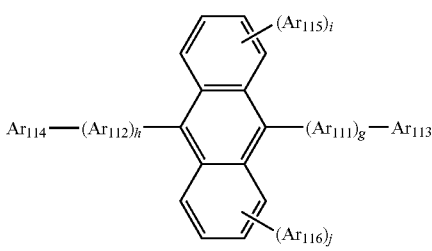

Alternatively, the host may further include a compound represented by Formula 301 below:

Formula 301

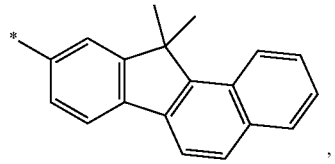 [SMILES: *c1ccc2c(c1)C(C)(C)c1c-2ccc2ccccc12]

In Formula 301, $Ar_{111}$ and $Ar_{112}$ may be each independently selected from:

a phenylene group, a naphthylene group, a phenanthrenylene group, and a pyrenylene group; and a phenylene group, a naphthylene group, a phenanthrenylene group, and a pyrenylene group, each substituted with at least one of a phenyl group, a naphthyl group, and an anthracenyl group.

In Formula 301, $Ar_{113}$ to $Ar_{116}$ may be each independently selected from:

a $C_1$-$C_{10}$ alkyl group, a phenyl group, a naphthyl group, a phenanthrenyl group, and a pyrenyl group; and a phenyl group, a naphthyl group, a phenanthrenyl group, and a pyrenyl group, each substituted with at least one of a phenyl group, a naphthyl group, and an anthracenyl group.

In Formula 301, g, h, i, and j may be each independently an integer selected from 0 to 4, and for example, may be each independently 0, 1, or 2.

In Formula 301, $Ar_{113}$ to $Ar_{116}$ may be each independently selected from:

a $C_1$-$C_{10}$ alkyl group substituted with at least one of a phenyl group, a naphthyl group, and an anthracenyl group;

a phenyl group, a naphthyl group, an anthracenyl group, a pyrenyl group, a phenanthrenyl group, and a fluorenyl group;

a phenyl group, a naphthyl group, an anthracenyl group, a pyrenyl group, a phenanthrenyl group, and a fluorenyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthracenyl group, a pyrenyl group, a phenanthrenyl group, and a fluorenyl group; and

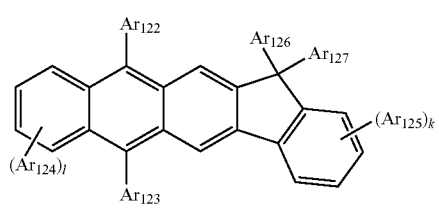

but they are not limited thereto.

Alternatively, the host may include a compound represented by Formula 302 below:

Formula 302

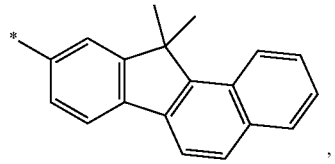 [SMILES: *c1ccc2c(c1)C(C)(C)c1c-2ccc2ccccc12]

In Formula 302, $Ar_{122}$ to $Ar_{125}$ may be understood by referring to the description provided in connection with $Ar_{113}$ of Formula 301.

In Formula 302, $Ar_{126}$ and $Ar_{127}$ may be each independently a $C_1$-$C_{10}$ alkyl group (e.g., a methyl group, an ethyl group, or a propyl group).

In Formula 302, k and l may be each independently an integer selected from 0 to 4. For example, k and l in Formula 302 may be 0, 1, or 2.

The compound of Formula 301 and the compound of Formula 302 may include Compounds H1 to H42 below, but they are not limited thereto:
H1
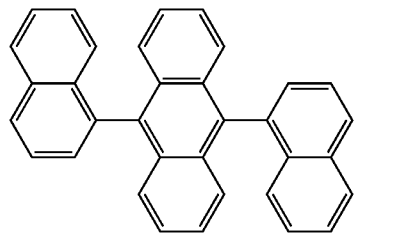
H2
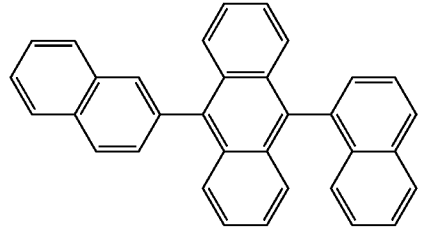
H3
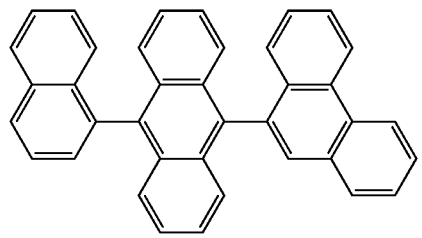
H4
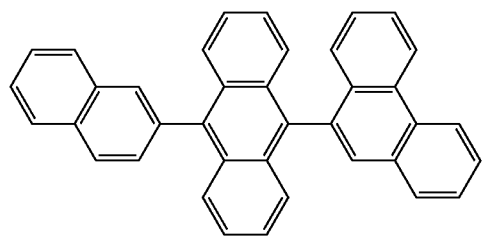
H5
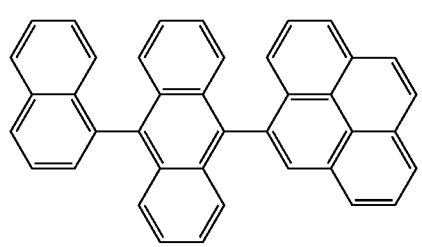
H6
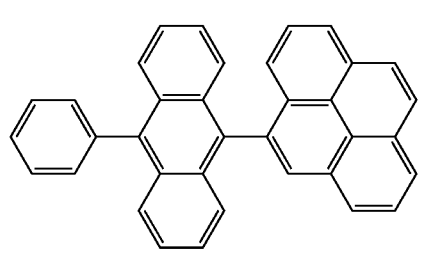
H7
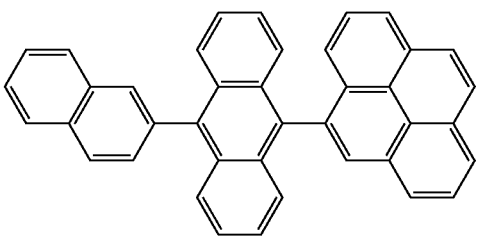
H8
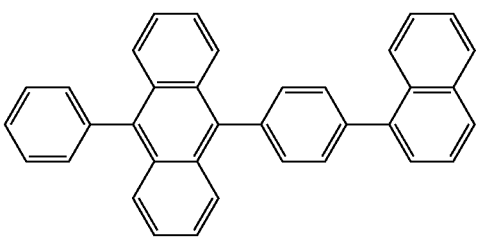
H9
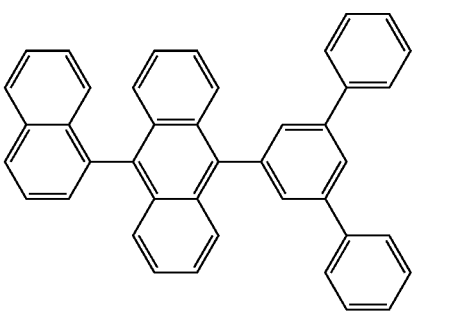
H10
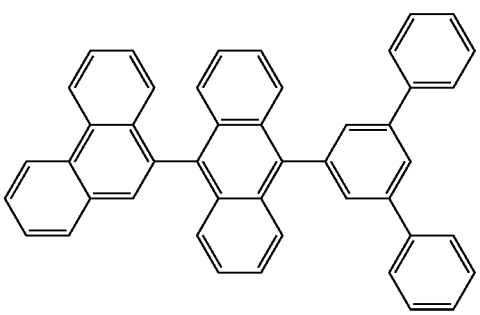
H11
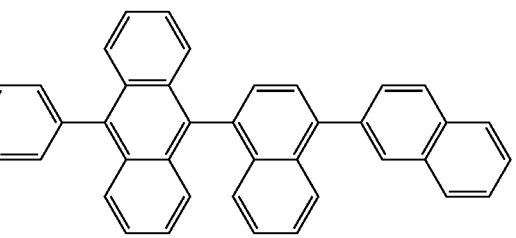
H12
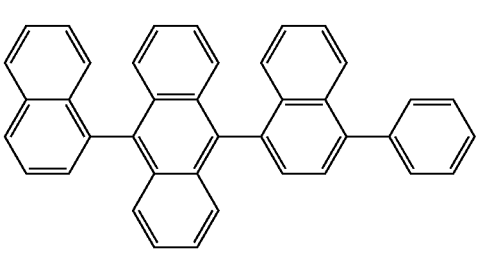

H13
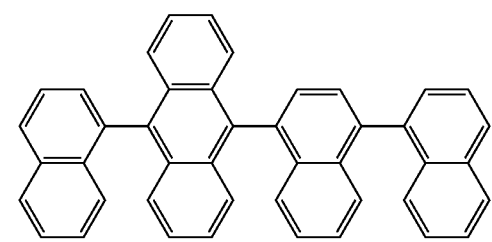
H14
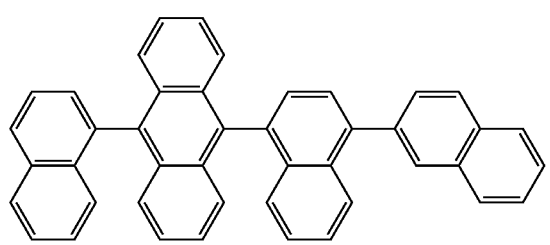
H15
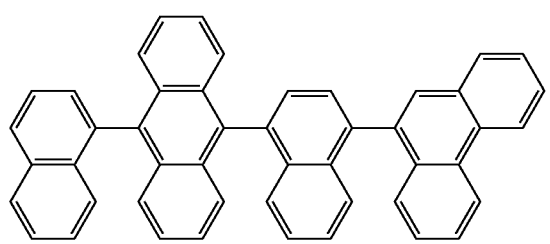
H16
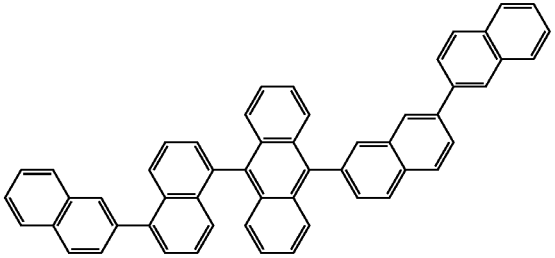
H17
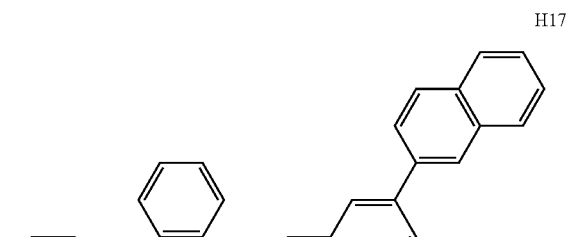
H18
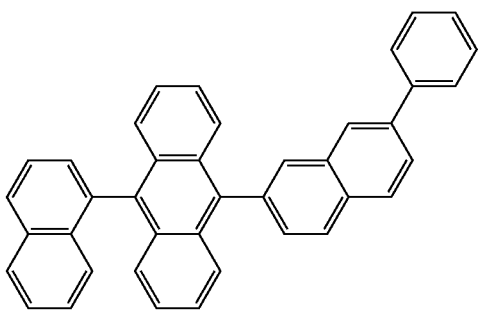
H18
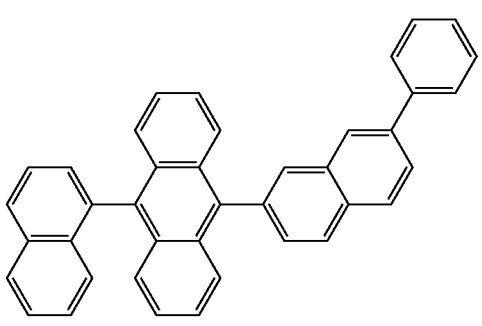
H19
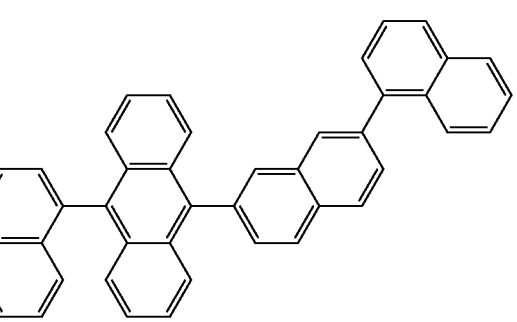
H20
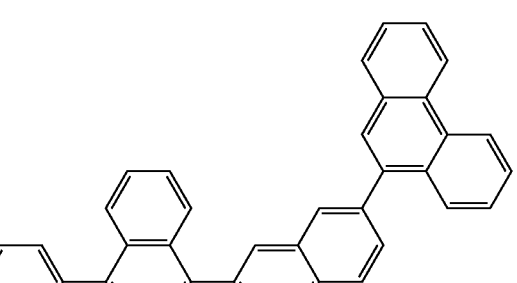
H21
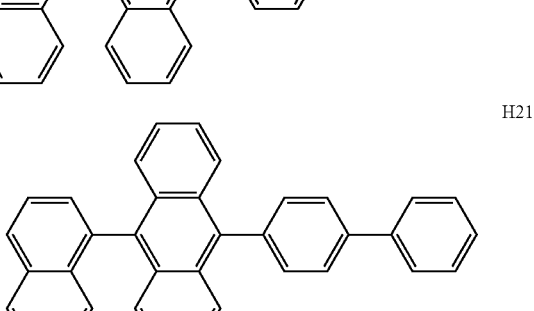

H22
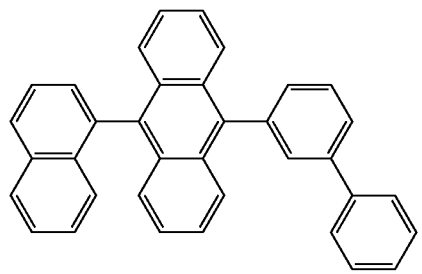
H23
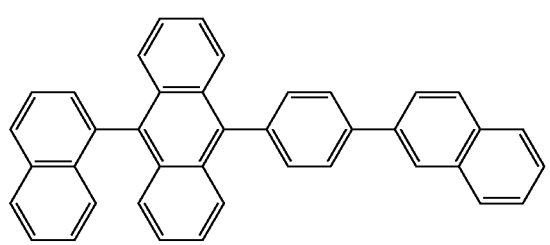
H24
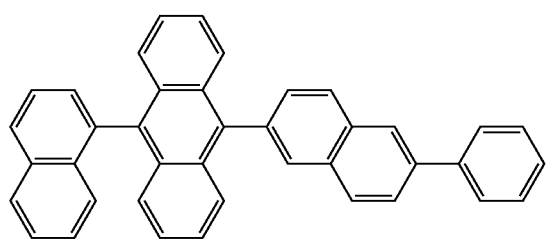
H25
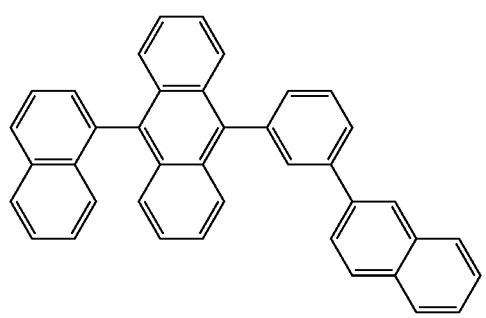
H26
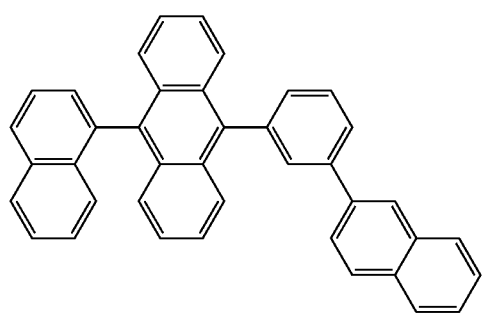
H27
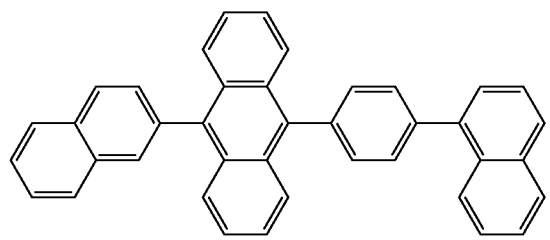
H28
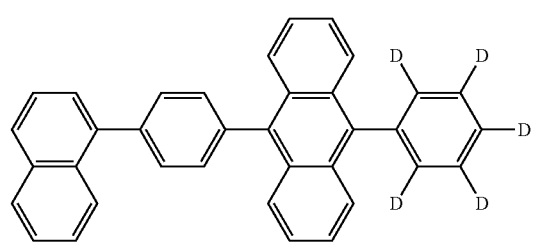
H29
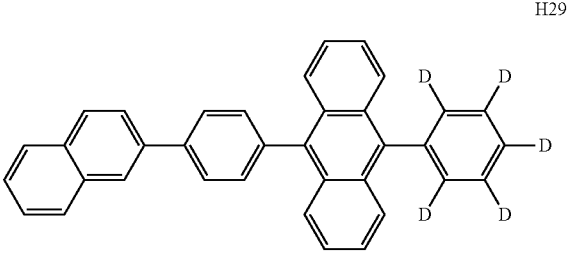
H30
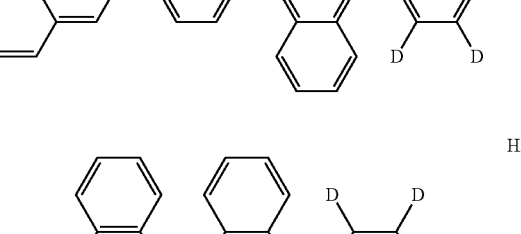
H31
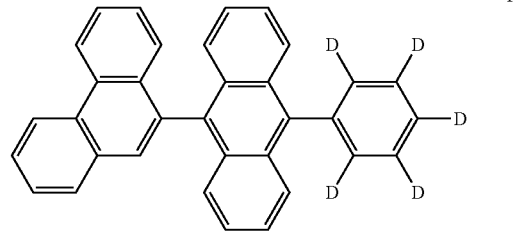
H32
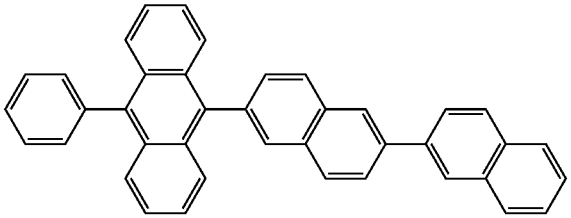

H33
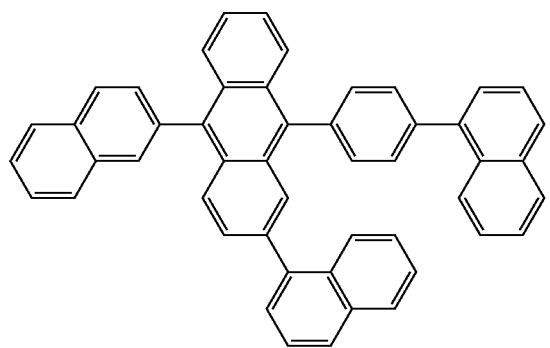
H34
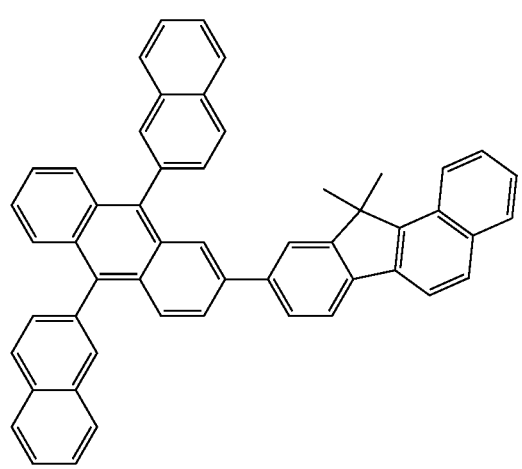
H35
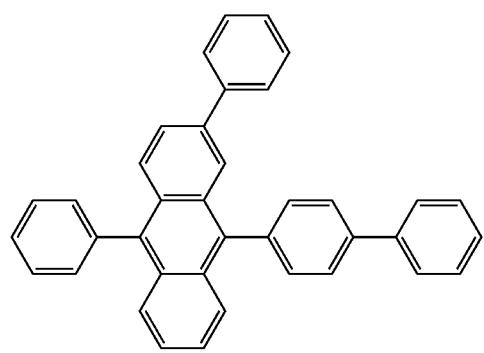
H36
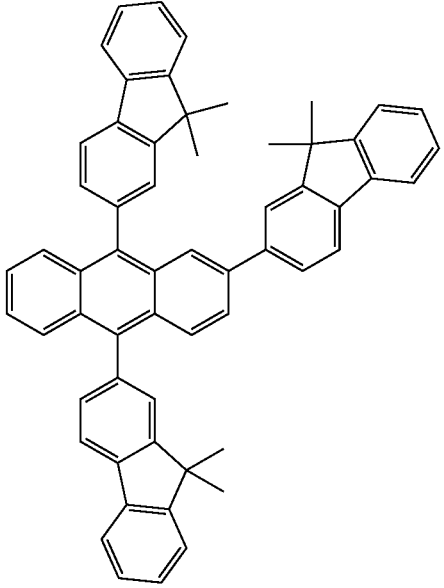
H37
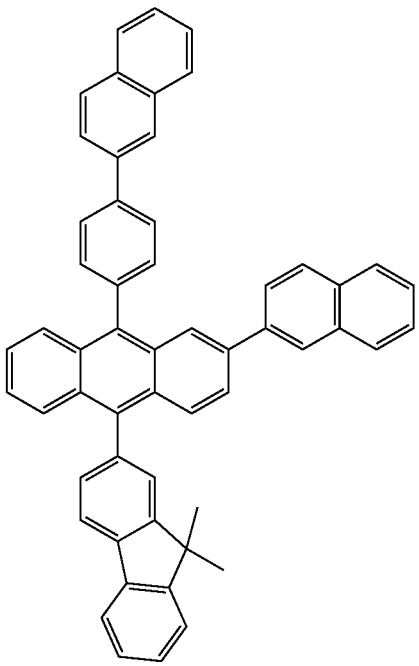
H38

H39

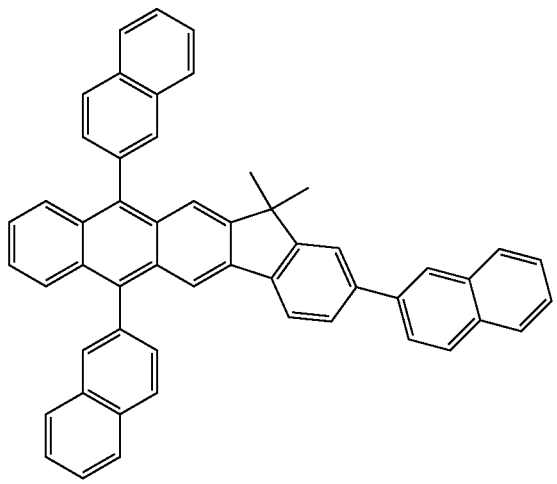

H40

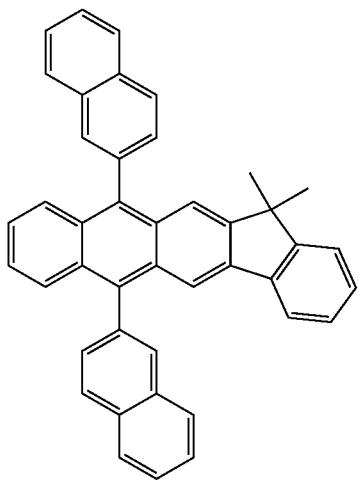

H41

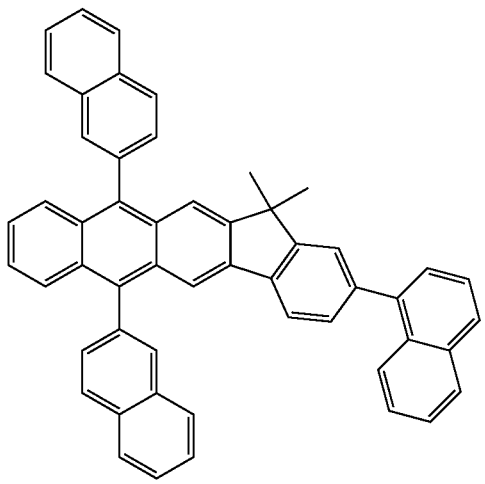

H42

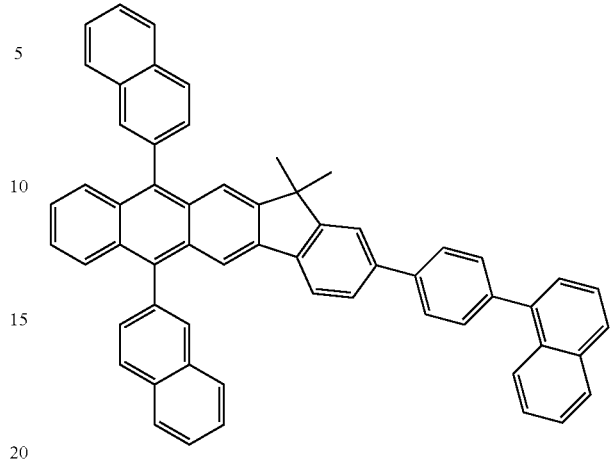

When the organic light-emitting device is a full-color organic light-emitting device, the EML may be patterned into a red EML, a green EML, and a blue EML. Alternatively, the EML may have various modifications in the structure, and for example, may have a structure of a red EML, a green EML, and/or a blue EML, each of which layers are sequentially stacked in the stated order, and accordingly the EML may emit white light.

When the EML includes a host and a dopant, an amount of the dopant may be in a range of about 0.01 to about 15 parts by weight, based on 100 parts by weight of the host, but is not limited thereto.

A thickness of the EML may be in a range of about 100 Å to about 1,000 Å, e.g., about 200 Å to about 600 Å. When the thickness of the EML is within these ranges, excellent emission characteristics may be obtained without a substantial increase in driving voltage.

Next, the electron transport region may be disposed on the EML.

The electron transport region may include at least one of a hole blocking layer (HBL), an electron transport layer (ETL), and an electron injection layer (EIL).

For example, the electron transport region may have a structure of HBL/ETL/EIL or a structure of ETL/EIL, but the structure of the electron transport region is not limited thereto. The electron transport layer may have a single-layer structure or a multi-layer structure including 2 or more layers.

Conditions for forming an HBL, an ETL, and an EIL of the electron transport region may be referred to those for forming the HIL.

When the electron transport region includes an HBL, the HBL may include at least one of, e.g., BCP, Bphen, and Balq below, but is not limited thereto:

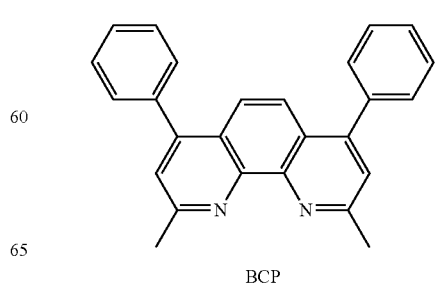

BCP

-continued

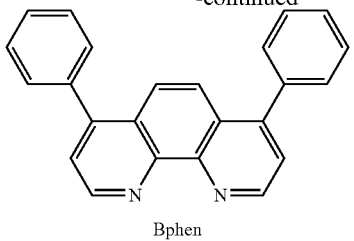
Bphen

A thickness of the HBL may be in a range of about 20 Å about 1,000 Å, e.g., about 30 Å to about 300 Å. When the thickness of the HBL is within these ranges, excellent hole blocking characteristics may be obtained without a substantial increase in driving voltage.

The ETL may further include at least one of BCP and Bphen above, Alq$_3$, Balq, TAZ, and NTAZ below:

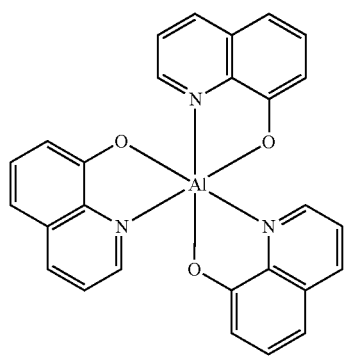
Alq$_3$

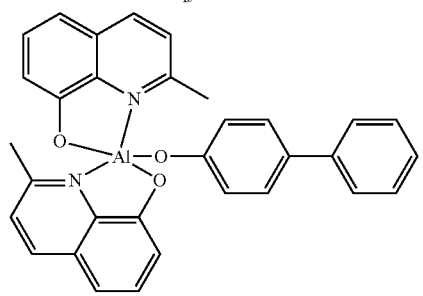
BAlq

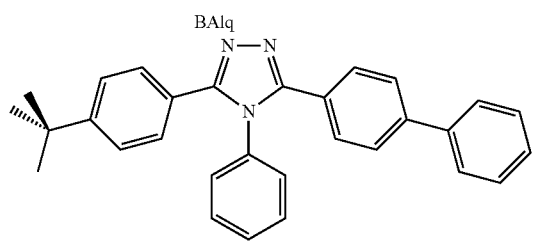
TAZ

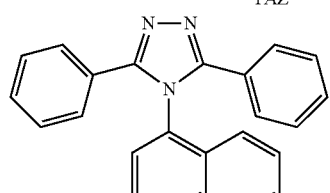
NTAZ

Alternatively, the ETL may include at least one of Compounds ET1 and ET2 below, but is not limited thereto:

ET1
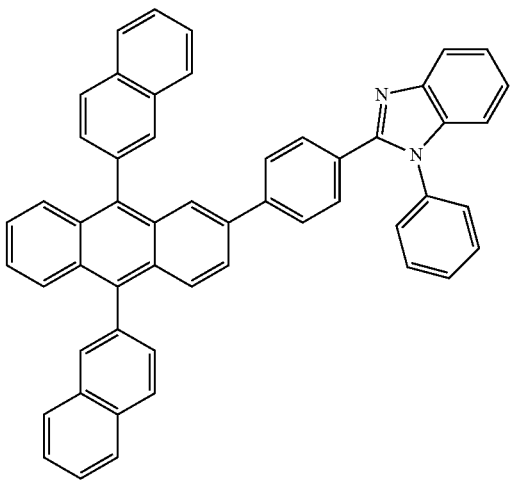

ET2
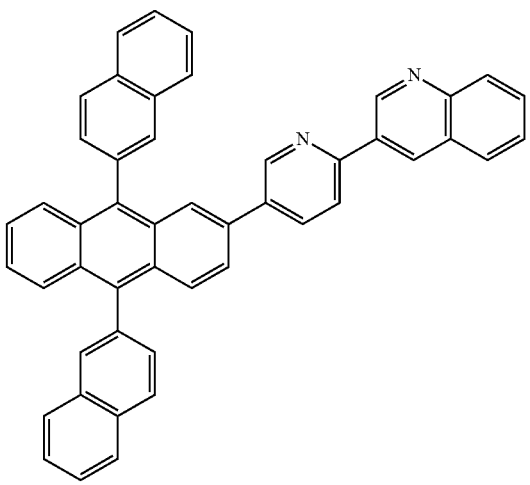

A thickness of the ETL may be in a range of about 100 Å to about 1,000 Å, e.g., about 150 Å to about 500 Å. When the thickness of the ETL is within these ranges, satisfactory electron transporting characteristics may be obtained without a substantial increase in driving voltage.

In addition to the materials described above, the ETL may further include a metal-containing material.

The metal-containing material may include a Li complex. The Li complex may include, e.g., Compound ET-D1 (e.g., lithium quinolate, LiQ) or Compound ET-D2 below:

ET-D1
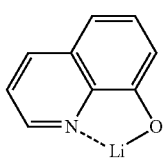

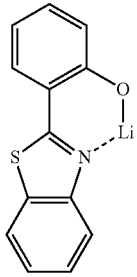

ET-D2

The electron transport region may include an EIL that facilitates electron injection from the second electrode 19.

The EIL may include at least one selected from LiF, NaCl, CsF, $Li_2O$, and BaO.

A thickness of the EIL may be in a range of about 1 Å to about 100 Å, e.g., about 3 Å to about 90 Å. When the thickness of the EIL is within these ranges, satisfactory electron injecting characteristics may be obtained without a substantial increase in driving voltage.

The second electrode 19 may be disposed on top of the organic layer 15, and may be a cathode. A material for forming the second electrode 19 may have a low work function, such as a metal, an alloy, an electrically conductive compound, or a mixture thereof. Detailed examples of the material for forming the second electrode 19 may include Li, Mg, Al, Al—Li, Ca, Mg—In, and Mg—Ag. Alternatively, to obtain a top emission device, the second electrode 19 may have various modifications in the material for forming the second electrode 19, and for example, may be ITO or IZO to form a transmissive electrode.

Hereinbefore, the organic light-emitting device has been described with reference to the FIGURE, but is not limited thereto.

A $C_1$-$C_{60}$ alkyl group as used herein refers to a linear or branched aliphatic hydrocarbon monovalent group having 1 to 60 carbon atoms. Detailed examples thereof are a methyl group, an ethyl group, a propyl group, an isobutyl group, a sec-butyl group, a tert-butyl group, a pentyl group, an iso-amyl group, and a hexyl group. A $C_1$-$C_{60}$ alkylene group as used herein refers to a divalent group having the same structure as the $C_1$-$C_{60}$ alkyl group.

A $C_1$-$C_{60}$ alkoxy group as used herein refers to a monovalent group represented by —$OA_{101}$ (wherein $A_{101}$ is the $C_1$-$C_{60}$ alkyl group). Detailed examples thereof are a methoxy group, an ethoxy group, and an isopropyloxy group.

A $C_2$-$C_{60}$ alkenyl group as used herein refers to a hydrocarbon group formed by substituting at least one carbon double bond in the middle or at the terminal of the $C_2$-$C_{60}$ alkyl group. Detailed examples thereof are an ethenyl group, a propenyl group, and a butenyl group. A $C_2$-$C_{60}$ alkenylene group as used herein refers to a divalent group having the same structure as the $C_2$-$C_{60}$ alkenyl group.

A $C_2$-$C_{60}$ alkynyl group as used herein refers to a hydrocarbon group formed by substituting at least one carbon triple bond in the middle or at the terminal of the $C_2$-$C_{60}$ alkyl group. Detailed examples thereof are an ethynyl group and a propynyl group. A $C_2$-$C_{60}$ alkynylene group as used herein refers to a divalent group having the same structure as the $C_2$-$C_{60}$ alkynyl group.

A $C_3$-$C_{10}$ cycloalkyl group as used herein refers to a monovalent hydrocarbon monocyclic group having 3 to 10 carbon atoms. Detailed examples thereof are a cyclopropyl group, a cyclobutyl group, a cyclopentyl group, a cyclohexyl group, and a cycloheptyl group. A $C_3$-$C_{10}$ cycloalkylene group as used herein refers to a divalent group having the same structure as the $C_3$-$C_{10}$ cycloalkyl group.

A $C_1$-$C_{10}$ heterocycloalkyl group as used herein refers to a monovalent monocyclic group having at least one heteroatom selected from N, O, P, and S as a ring-forming atom and 1 to 10 carbon atoms. Detailed examples thereof are a tetrahydrofuranyl group and a tetrahydrothiophenyl group. A $C_1$-$C_{10}$ heterocycloalkylene group as used herein refers to a divalent group having the same structure as the $C_1$-$C_{10}$ heterocycloalkyl group.

A $C_3$-$C_{10}$ cycloalkenyl group as used herein refers to a monovalent monocyclic group that has 3 to 10 carbon atoms and at least one double bond in the ring thereof, and which is not aromatic. Detailed examples thereof are a cyclopentenyl group, a cyclohexenyl group, and a cycloheptenyl group. A $C_3$-$C_{10}$ cycloalkenylene group as used herein refers to a divalent group having the same structure as the $C_3$-$C_{10}$ cycloalkenyl group.

A $C_1$-$C_{10}$ heterocycloalkenyl group as used herein refers to a monovalent monocyclic group that has at least one heteroatom selected from N, O, P, and S as a ring-forming atom, 1 to 10 carbon atoms, and at least one double bond in its ring. Detailed examples of the $C_1$-$C_{10}$ heterocycloalkenyl group are a 2,3-dihydrofuranyl group and a 2,3-dihydrothiophenyl group. A $C_1$-$C_{10}$ heterocycloalkenylene group as used herein refers to a divalent group having the same structure as the $C_1$-$C_{10}$ heterocycloalkenyl group.

A $C_6$-$C_{60}$ aryl group as used herein refers to a monovalent group having a carbocyclic aromatic system having 6 to 60 carbon atoms, and a $C_6$-$C_{60}$ arylene group as used herein refers to a divalent group having a carbocyclic aromatic system having 6 to 60 carbon atoms. Detailed examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

A $C_1$-$C_{60}$ heteroaryl group as used herein refers to a monovalent group having a carbocyclic aromatic system that has at least one heteroatom selected from N, O, P, and S as a ring-forming atom, and 1 to 60 carbon atoms. A $C_1$-$C_{60}$ heteroarylene group as used herein refers to a divalent group having a carbocyclic aromatic system that has at least one heteroatom selected from N, O, P, and S as a ring-forming atom, and 1 to 60 carbon atoms. Detailed examples of the $C_1$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be fused to each other.

A $C_6$-$C_{60}$ aryloxy group as used herein indicates —$OA_{102}$ (wherein $A_{102}$ is the $C_6$-$C_{60}$ aryl group), and a $C_6$-$C_{60}$ arylthio group as used herein indicates —$SA_{103}$ (wherein $A_{103}$ is the $C_6$-$C_{60}$ aryl group).

A monovalent non-aromatic condensed polycyclic group (e.g., a group having 8 to 60 carbon atoms) as used herein refers to a monovalent group that has two or more rings condensed to each other, has carbon atoms only as a ring-forming atom, and which is non-aromatic in the entire molecular structure. A detailed example of the monovalent non-aromatic condensed polycyclic group is a fluorenyl group. A divalent non-aromatic condensed polycyclic group as used herein refers to a divalent group having the same structure as the monovalent non-aromatic condensed polycyclic group.

A monovalent condensed heteropolycyclic group (e.g., a group having 1 to 60 carbon atoms) as used herein refers to a monovalent group that has two or more rings condensed to each other, has heteroatoms as a ring-forming atom selected from N, O, Si, P, and S in addition to C, and which is non-aromatic in the entire molecular structure. A detailed example of the monovalent non-aromatic condensed heteropolycyclic group is a carbazolyl group. A divalent non-aromatic condensed heteropolycyclic group as used herein refers to a divalent group having the same structure as the monovalent non-aromatic condensed heteropolycyclic group.

At least one of substituents of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

a deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), —B($Q_{16}$)($Q_{17}$), and —P(=O)($Q_{18}$)($Q_{19}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one of a deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), —B($Q_{26}$)($Q_{27}$), and —P(=O)($Q_{28}$)($Q_{29}$); and —N($Q_{31}$)($Q_{32}$), —Si($Q_{33}$)($Q_{34}$)($Q_{35}$), —B($Q_{36}$)($Q_{37}$), and —P(=O)($Q_{38}$)($Q_{39}$), wherein $Q_1$ to $Q_9$, $Q_{11}$ to $Q_{19}$, $Q_{21}$ to $Q_{29}$, and $Q_{31}$ to $Q_{39}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

Hereinafter, the organic light-emitting device according to embodiments is described in detail with reference to Synthesis Example and Examples. The wording "B was used instead of A" used in describing Synthesis Examples means that a molar equivalent of A was identical to a molar equivalent of B.

Example

Synthesis Example 1: Synthesis of Compound 2

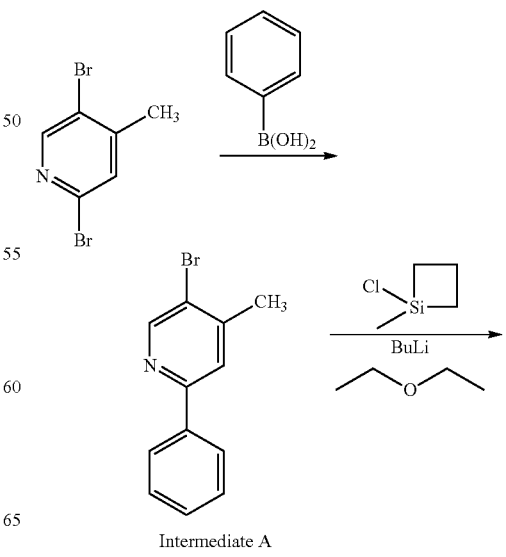

Intermediate A

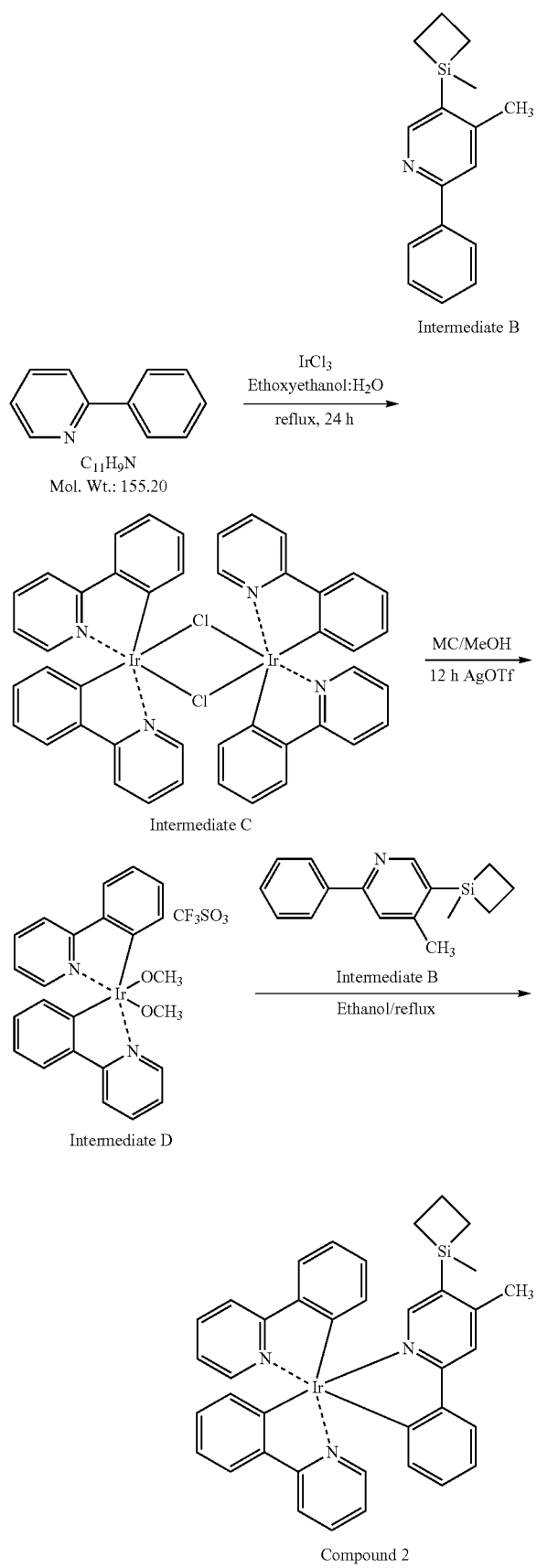

Synthesis of Intermediate A (5-bromo-4-methyl-2-phenylpyridine)

10.8 grams (g) (0.043 moles (mol)) of 2,5-dibromo-4-methylpyridine and 5.773 g (0.047 mol) of phenylboronic acid were put in a flask, and 0.483 g (0.002 mol) of Pd(OAc)$_2$, 1.129 g (0.004 mol) of PPh$_3$, and 17.845 g (0.129 mol) of K$_2$CO$_3$ were added thereto. A mixture of acetonitrile (ACN)/methanol (MeOH) (at a volume ratio of 2:1, 120 mL) was added to the flask, and the reaction was stirred at a temperature of 50° C. overnight. After the product obtained therefrom (which had ivory color) was cooled to room temperature and filtered, the precipitate was washed with EA/H$_2$O and purified by using column chromatography to obtain 6.9 g (yield: 65%) of Intermediate A.

Synthesis of Intermediate B (4-methyl-5-(1-methyl-siletan-1-yl)-2-phenylpyridine)

6.9 g (0.028 mol) of Intermediate A was dissolved in diethyl ether, and stirred at a temperature of −78° C. for 30 minutes. 12.8 mL (1.6 molar (M) solution) of n-BuLi was slowly added thereto through a syringe, and the mixture was stirred again for 1 hour. The product obtained therefrom was mixed with 2.74 mL (1.2 equivalents (equiv.)) of 1-chloro-1-methylsilane that was slowly added thereto through a syringe. After the mixed solution was heated to room temperature, the resultant mixed solution was stirred for 12 hours, so as to obtain 4.3 g (yield: 62%) of Intermediate B.

Synthesis of Intermediate C 7.9 g (0.044 mol) of iridium chloride and 7.8 g (0.094 mol) of 2-phenylpyridine were added to 280 milliliters (ml) of a mixture of ethoxyethanol and water in a ratio of 3:1, and the mixed solution was refluxed for 18 hours. After the mixed solution was subjected to filtration of precipitates (yellow solids), the precipitate filtrate was washed with methanol and dried in a vacuum oven to obtain Intermediate C.

Synthesis of Intermediate D

In a flask, a mixture of 10 g (0.009 mol) of Intermediate C and 90 ml of MC was added to a mixture of 4.9 g (0.019 mol) of AgOTf and 30 ml of MeOH. The flask was covered by an aluminum foil to protect the reaction from the action of light, and stirred overnight (12 hours). After the product obtained therefrom was filtered through celites, the filtrate was removed under reduced pressure to obtain Intermediate D.

Synthesis of Compound 2

3 g (4.2 mmol) of Intermediate D and 1.2 g (5.1 mmol) of Intermediate B (4-methyl-5-(1-methylsiletan-1-yl)-2-phenylpyridine) were added to 40 ml of EtOH, and the mixed solution was refluxed for 18 hours to obtain 0.63 g (yield: 20%) of Compound 2.

C$_{38}$H$_{34}$IrN$_3$Si: M+ 753.22

1H NMR (CDCl$_3$, 300 MHz) δ(ppm) 8.72 (s, 1H), 8.56 (d, 2H), 8.16 (d, 3H), 7.82 (d, 3H), 7.52-7.38 (m, 11H), 6.95 (t, 2H), 2.44 (s, 3H), 1.21 (t, 2H), 0.61 (d, 4H), 0.33 (s, 3H)

Synthesis Example 2: Synthesis of Compound 3

Compound 3 (1.8 g, yield: 15%) was synthesized in the same manner as in Synthesis Example 1, except in synthesis of Intermediate A, 2,5-dibromo-4-isobutylpyridine was used instead of 2,5-dibromo-4-methylpyridine.

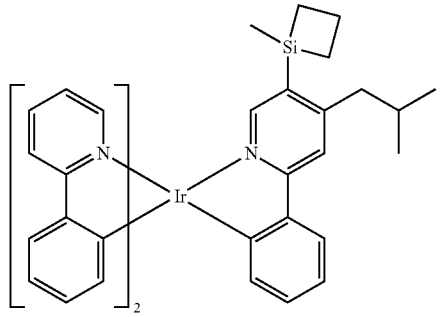

C$_{41}$H$_{40}$IrN$_3$Si: M+ 759.26

1H NMR (CDCl$_3$, 300 MHz) δ(ppm) 8.79 (s, 1H), 8.56 (d, 2H), 8.16 (d, 3H), 7.82 (d, 3H), 7.52-7.38 (m, 11H), 6.95 (t, 2H), 3.29 (d, 2H), 2.44 (s, 3H), 1.8 (m, 1H), 1.21 (t, 2H), 0.86 (s, 6H), 0.61 (d, 4H), 0.33 (s, 3H)

Synthesis Example 3: Synthesis of Compound 4

Compound 4 (1.2 g, yield: 12%) was synthesized in the same manner as in Synthesis Example 1, except in synthesis of Intermediate A, 2,5-dibromo-4-isobutylpyridine and biphenylboronic acid were used instead of 2,5-dibromo-4-methylpyridine and phenylboronic acid, respectively.

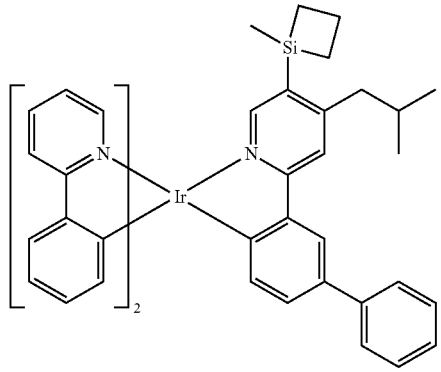

C$_{41}$H$_{40}$IrN$_3$Si: M+ 871.29

1H NMR (CDCl$_3$, 300 MHz) δ(ppm) 8.79 (s, 1H), 8.56 (d, 2H), 8.40 (s, 1H), 8.16 (d, 3H), 7.82-7.71 (m, 7H), 7.52-7.38 (m, 11H), 6.95 (t, 2H), 3.29 (d, 2H), 2.44 (s, 3H), 1.8 (m, 1H), 1.21 (t, 2H), 0.86 (s, 6H), 0.61 (d, 4H), 0.33 (s, 3H)

Example 1

As an anode substrate, a glass substrate on which ITO/Ag/ITO was formed to a thickness of 70 Angstrom (Å)/1,000 Å/70 Å was cut to a size of 50 millimeters (mm)×50 mm×0.5 mm, sonicated by using isopropyl alcohol and pure water each for 5 minutes, and cleaned by the exposure to UV ozone for 30 minutes. Then, the anode was equipped with a vacuum deposition apparatus.

2-TNATA was deposited on the anode to form a hole injection layer having a thickness of 600 Å. 4,4'-bis[N-(1-naphthyl)-N-phenyl amino]biphenyl (hereinafter, referred to as NPB) was deposited on the hole injection layer to form a hole transport layer having a thickness of 1,000 Å.

CBP (host), and Compound 2 (dopant), were co-deposited on the hole transport layer at a weight ratio of 91:9 to form an emission layer having a thickness of 250 Å.

BCP was deposited on the emission layer to form a hole blocking layer having a thickness of 50 Å. Then, Alq$_3$ was deposited on the hole blocking layer to form an electron transport layer having a thickness of 350 Å. LiF was deposited on the electron transport layer to form an electron injection layer having a thickness of 10 Å. Mg and Ag were deposited on the electron injection layer at a weight ratio of 90:10 to form a cathode having a thickness of 120 Å, thereby manufacturing an organic light-emitting device (emitting green light).

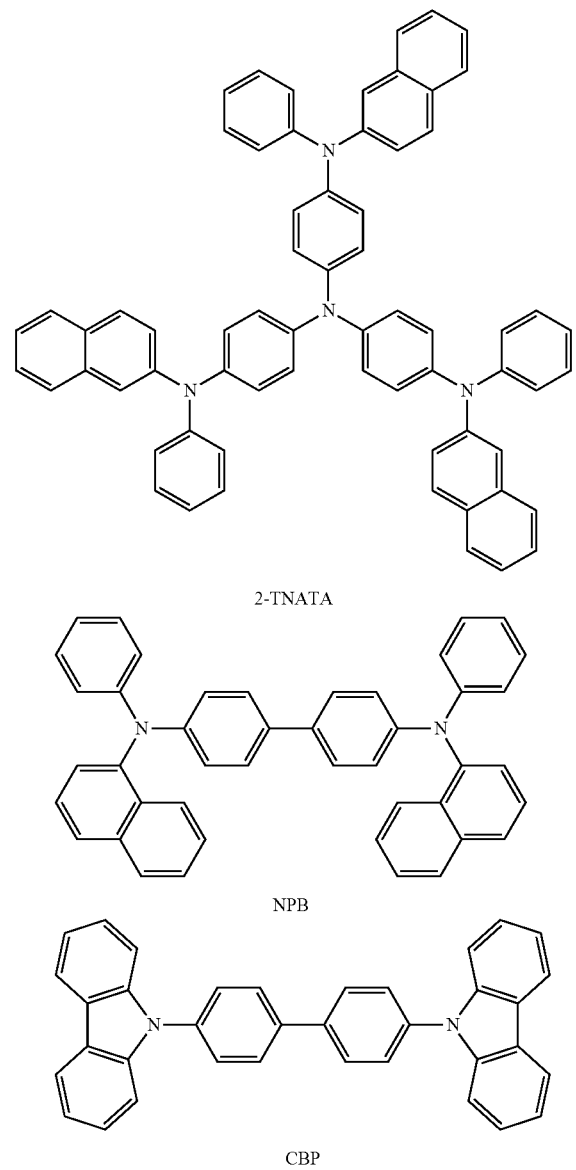

-continued

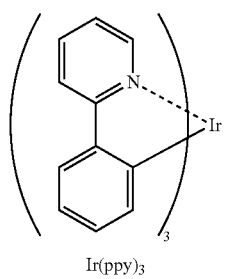

Ir(ppy)₃

Examples 2 and 3 and Comparative Examples 1 and 2

Organic light-emitting device was manufactured in the same manner as in Example 1, except that in forming the emission layer, compounds listed in Table 2 below were each used instead of Compound 2 as a dopant.

Evaluation Example 1

The organic light-emitting devices of Examples 1 to 3 and Comparative Examples 1 and 2 were subjected to evaluation of driving voltage, current density, brightness, efficiency, and color purity, by using PR650 Spectroscan Source Measurement Unit. (available by PhotoResearch Company). Here, $LT_{97}$ refers to lifespan data obtained by measuring times required to reach 97% of brightness when initial brightness is considered as 100% with respect to current density of 10 milliAmperes per square centimeter (mA/cm²). The results are shown in Table 2 below.

TABLE 2

| Dopant | Driving voltage (V) | Current density (Ma/cm²) | Brightness (cd/m²) | Efficiency (cd/A) | Emission color | $LT_{97}$ (HR) |
|---|---|---|---|---|---|---|
| Example 1 | Compound 2 | 5.2 | 10 | 6324 | 65.8 | green | 108 |
| Example 2 | Compound 3 | 5.0 | 10 | 6782 | 70.2 | green | 120 |
| Example 3 | Compound 4 | 5.2 | 10 | 6560 | 67.2 | green | 116 |
| Comparative Example 1 | Ir(ppy)₃ | 7.0 | 10 | 4712 | 40.1 | green | 32 |
| Comparative Example 2 | Compound B | 6.8 | 10 | 4520 | 38.2 | green | 58 |

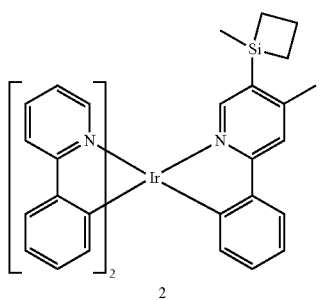

2

TABLE 2-continued

| Dopant | Driving voltage (V) | Current density (Ma/cm²) | Brightness (cd/m²) | Efficiency (cd/A) | Emission color | $LT_{97}$ (HR) |
|---|---|---|---|---|---|---|

3

4

Compound B

Referring to Table 2, it was confirmed that the organic light-emitting devices of Examples 1 to 3 had better driving voltage, brightness, efficiency, and lifespan characteristics than those of the organic light-emitting devices of Comparative Examples 1 and 2.

As described above, according to the one or more of the above exemplary embodiments, an organometallic compound has excellent electric characteristics and thermal stability, and thus an organic light-emitting device including the organometallic compound also has excellent driving voltage, current density, efficiency, color purity, and lifespan characteristics.

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the FIGURES, it will be understood by those of ordinary skill in the art that various changes in form and details may be made therein without departing from the spirit and scope of the present inventive concept as defined by the following claims.

What is claimed is:

1. An organometallic compound represented by Formula 1:

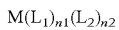

Formula 1 wherein M in Formula 1 is Ir;

$L_1$ in Formula 1 is selected from ligands represented by Formulae 2A-1 to 2A-45, and n1 is 1, 2, or 3, wherein when n1 is 2 or more, 2 or more groups Li are identical to or different from each other;

$L_2$ in Formula 1 is selected from organic ligands represented by Formulae 3-1(1) to 3-1(70), and n2 is 0, 1, or 2, wherein when n2 is or more, 2 or more groups $L_2$ are identical to or different from each other;

n1+n2 is 3;

$L_1$ and $L_2$ in Formula 1 are different from each other;

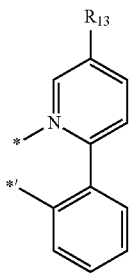

Formula 2A-1

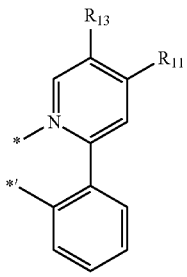

Formula 2A-2

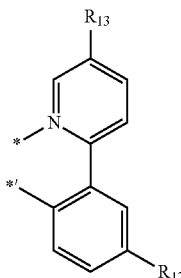

Formula 2A-3

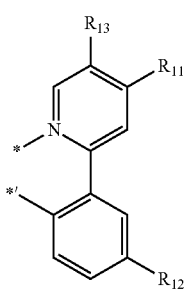

Formula 2A-4

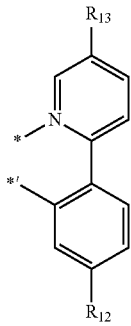

Formula 2A-5

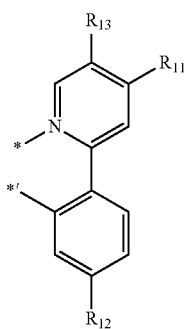

Formula 2A-6

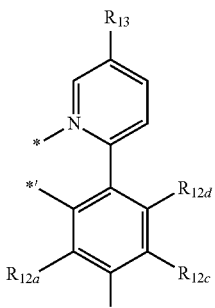

Formula 2A-7

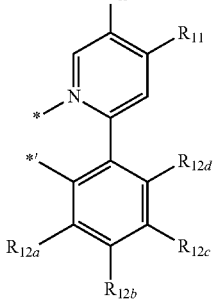

Formula 2A-8

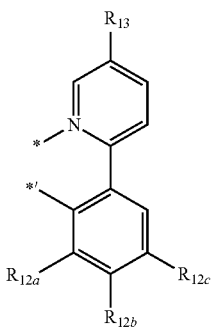

Formula 2A-9

-continued
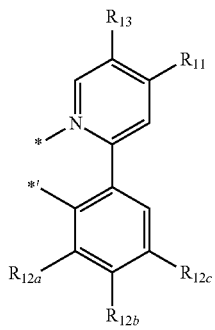
Formula 2A-10
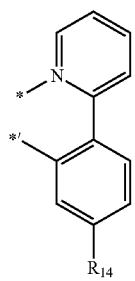
Formula 2A-11
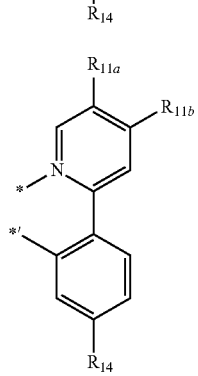
Formula 2A-12
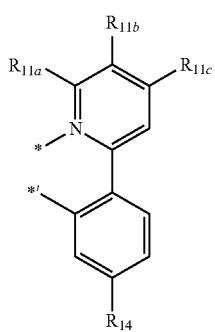
Formula 2A-13
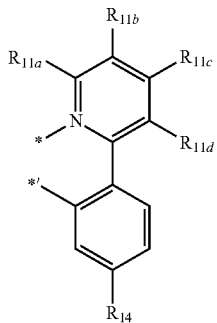
Formula 2A-15
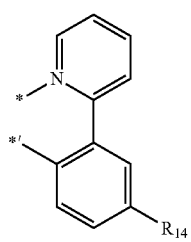
Formula 2A-16
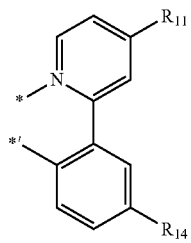
Formula 2A-17
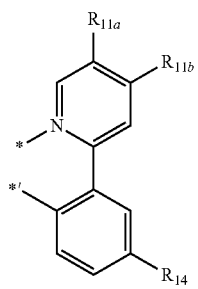
Formula 2A-18
Formula 2A-14
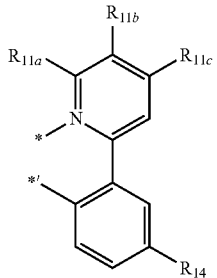
Formula 2A-19

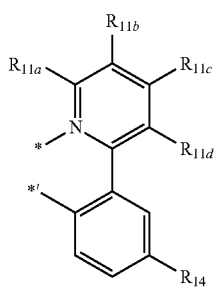
Formula 2A-20
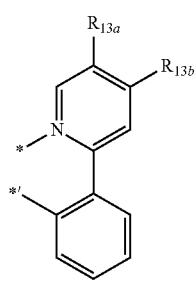
Formula 2A-21
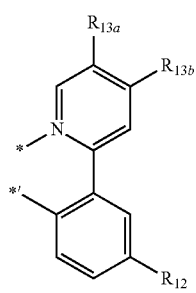
Formula 2A-22
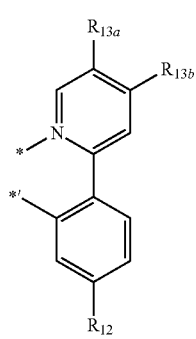
Formula 2A-23
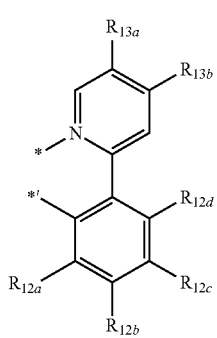
Formula 2A-24
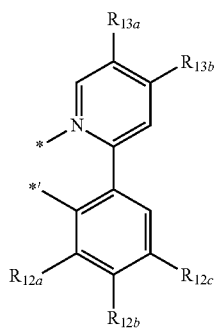
Formula 2A-25
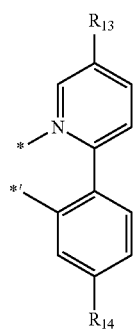
Formula 2A-26
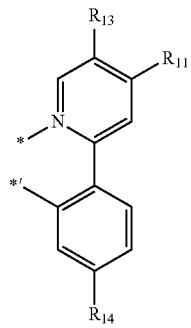
Formula 2A-27
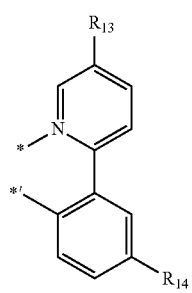
Formula 2A-28
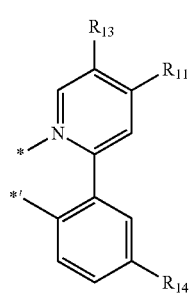
Formula 2A-29

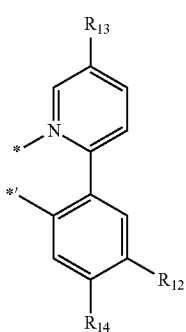
Formula 2A-30
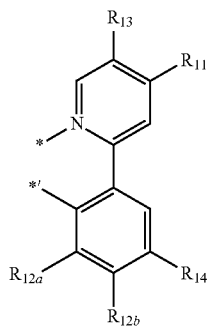
Formula 2A-35
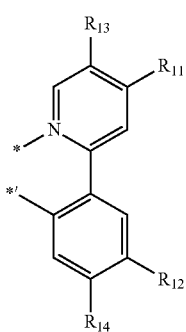
Formula 2A-31
Formula 2A-36
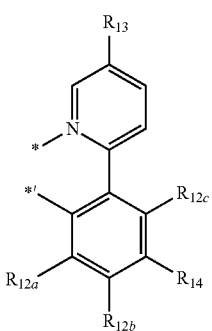
Formula 2A-32
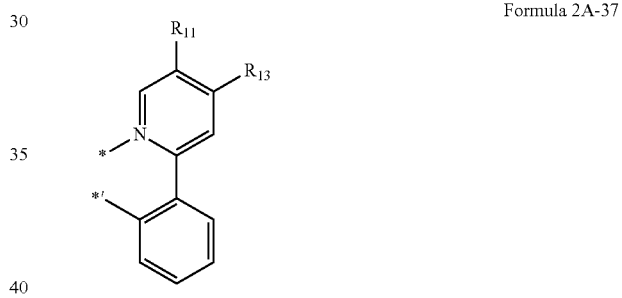
Formula 2A-37
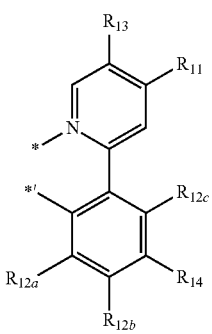
Formula 2A-33
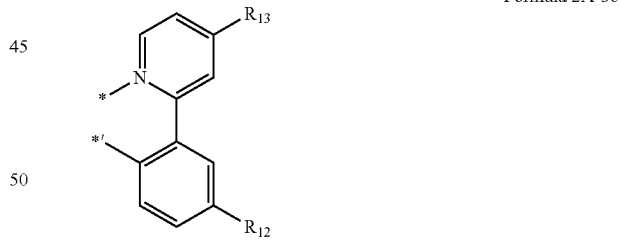
Formula 2A-38
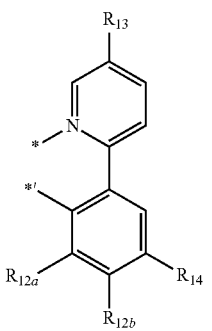
Formula 2A-34
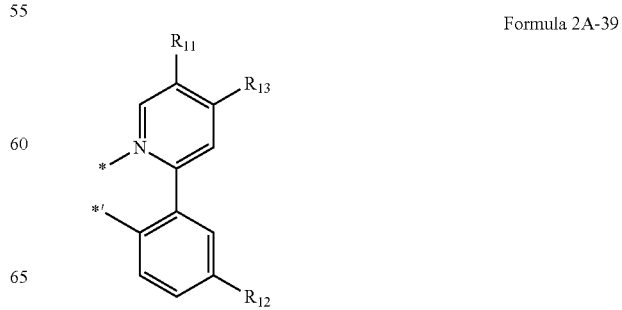
Formula 2A-39

-continued

Formula 2A-40
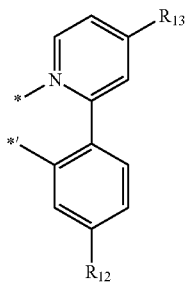

Formula 2A-41
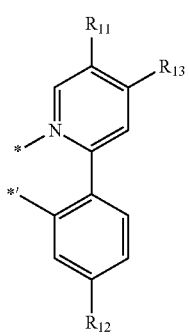

Formula 2A-42
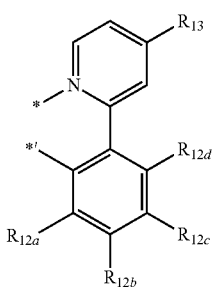

Formula 2A-43
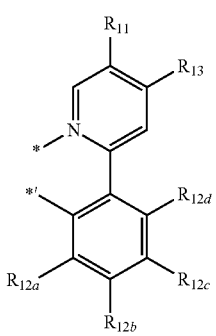

Formula 2A-44
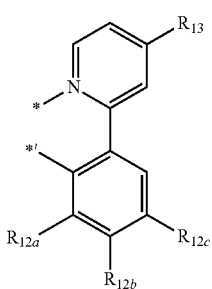

-continued

Formula 2A-45
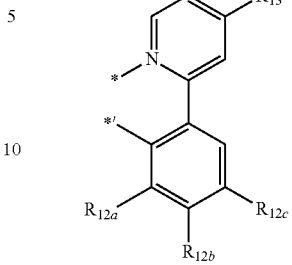

wherein in Formulae 2A-1 to 2A-45,

* and *' each indicates a binding site to M of Formula 1, $R_{11}$, $R_{11a}$ to $R_{11c}$, $R_{12}$ and $R_{12a}$ to $R_{12c}$ are each independently a deuterium, —F, a cyano group, a nitro group, —$SF_5$, —$CH_3$, —$CD_3$, —$CD_2H$, —$CDH_2$, —$CF_3$, —$CF_2H$, —$CFH_2$, groups represented by Formulae 9-1 to 9-17, and groups represented by Formulae 10-7 to 10-30, and $R_{13}$, $R_{13a}$, $R_{13b}$, and $R_{14}$ are each independently selected from groups represented by Formulae 2B(1) to 2B(18):
and Formula 2B(1)
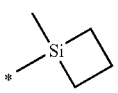

Formula 2B(2)
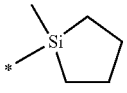

Formula 2B(3)

Formula 2B(4)
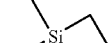

Formula 2B(5)
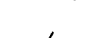

Formula 2B(6)
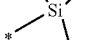

Formula 2B(7)
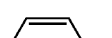

Formula 2B(8)
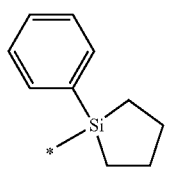
Formula 2B(9)
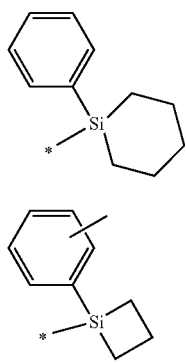
Formula 2B(10)
Formula 2B(11)
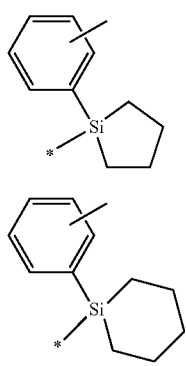
Formula 2B(12)
Formula 2B(13)
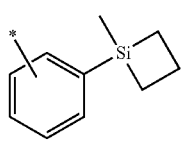
Formula 2B(14)
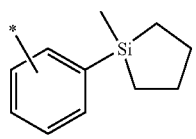
Formula 2B(15)
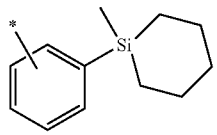
Formula 2B(16)
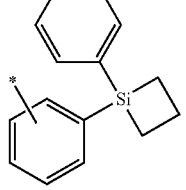
Formula 2B(17)
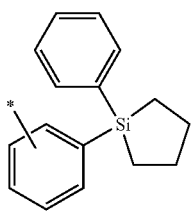
Formula 2B(18)
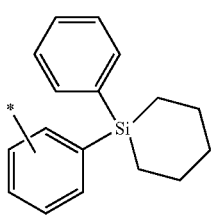
* in Formulae 2B(1) to 2B(18) indicates a binding site to a neighboring atom; and
Formula 3-1(1)
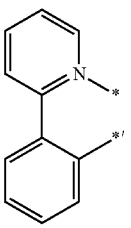
Formula 3-1(2)
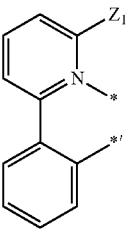
Formula 3-1(3)
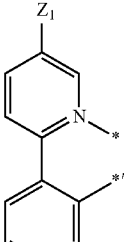
Formula 3-1(4)
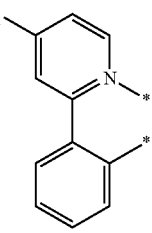

-continued
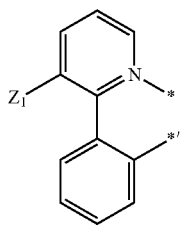
Formula 3-1(5)
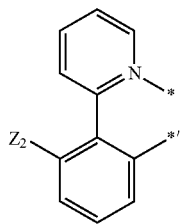
Formula 3-1(6)
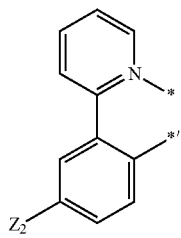
Formula 3-1(7)
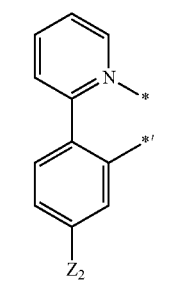
Formula 3-1(8)
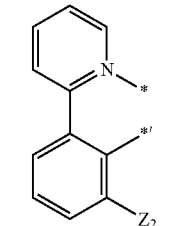
Formula 3-1(9)
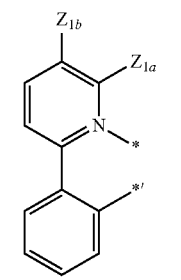
Formula 3-1(10)
-continued
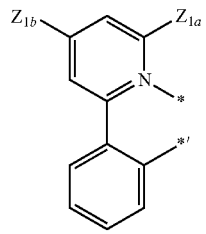
Formula 3-1(11)
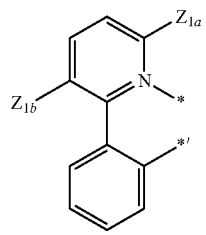
Formula 3-1(12)
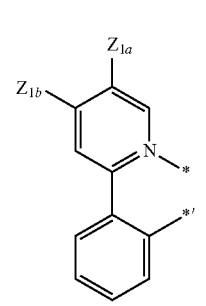
Formula 3-1(13)
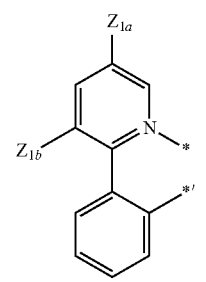
Formula 3-1(14)
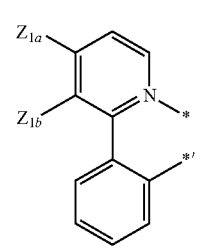
Formula 3-1(15)
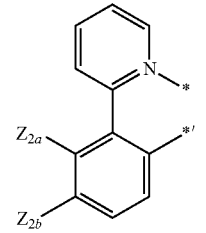
Formula 3-1(16)

Formula 3-1(17)
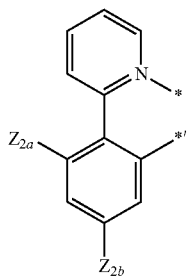
Formula 3-1(18)
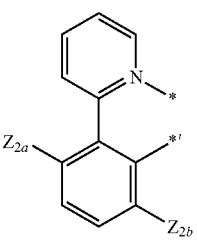
Formula 3-1(19)
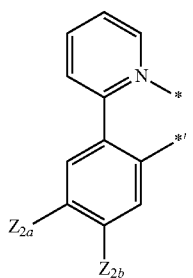
Formula 3-1(20)
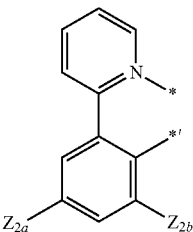
Formula 3-1(21)
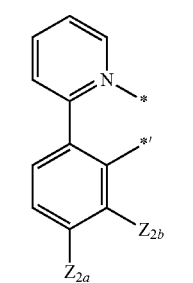
Formula 3-1(22)
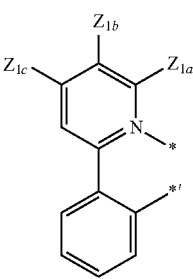
Formula 3-1(23)
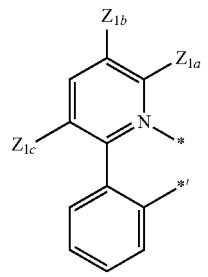
Formula 3-1(24)
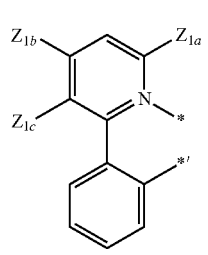
Formula 3-1(25)
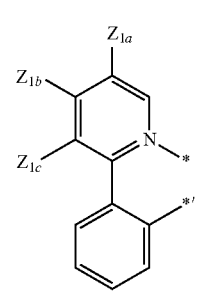
Formula 3-1(26)
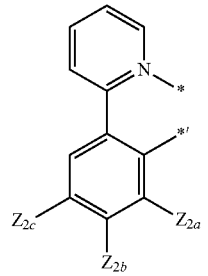
Formula 3-1(27)
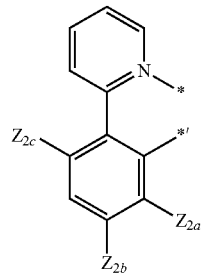
Formula 3-1(28)
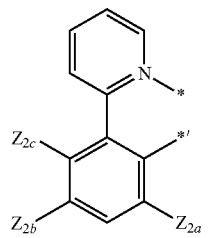

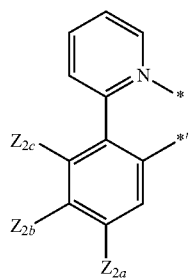
Formula 3-1(29)
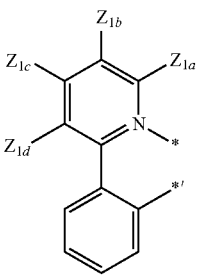
Formula 3-1(30)
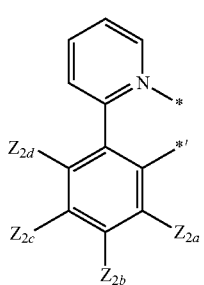
Formula 3-1(31)
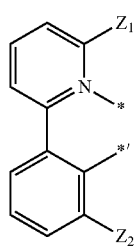
Formula 3-1(32)
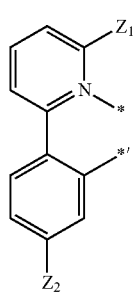
Formula 3-1(33)
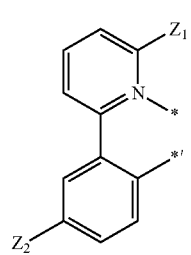
Formula 3-1(34)
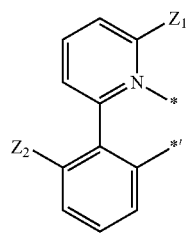
Formula 3-1(35)
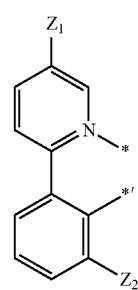
Formula 3-1(36)
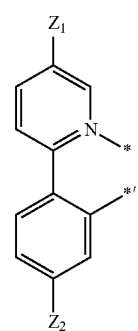
Formula 3-1(37)
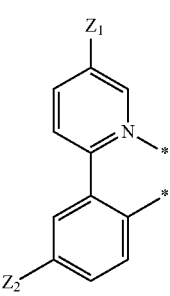
Formula 3-1(38)
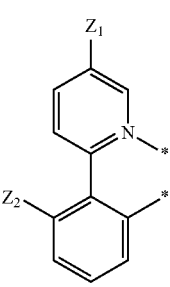
Formula 3-1(39)

-continued
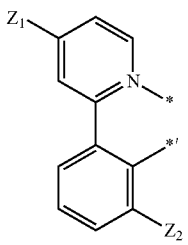
Formula 3-1(40)
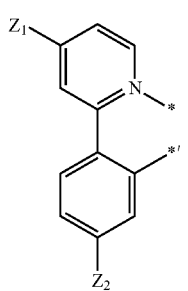
Formula 3-1(41)
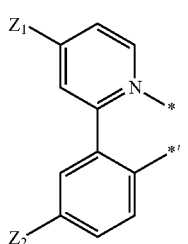
Formula 3-1(42)
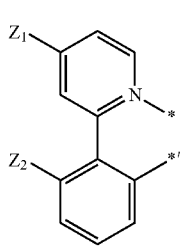
Formula 3-1(43)
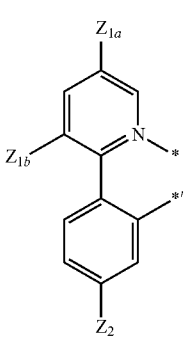
Formula 3-1(44)
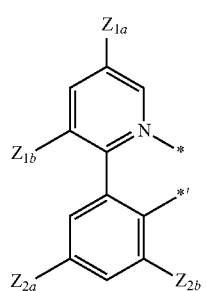
Formula 3-1(45)
-continued
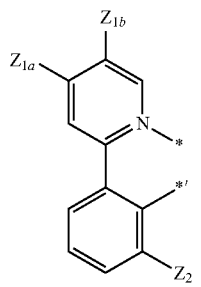
Formula 3-1(46)
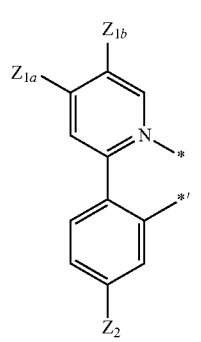
Formula 3-1(47)
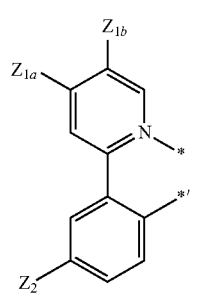
Formula 3-1(48)
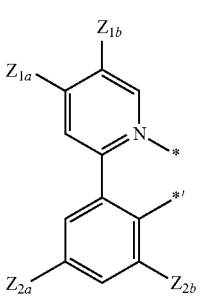
Formula 3-1(49)
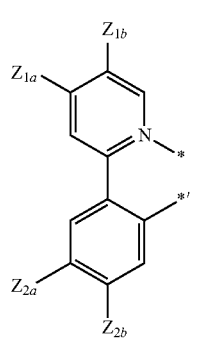
Formula 3-1(50)

Formula 3-1(51)
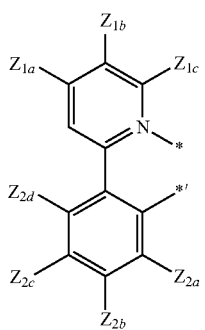
Formula 3-1(52)
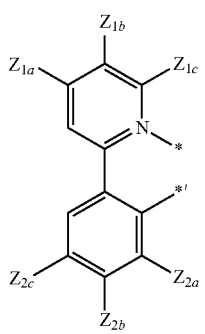
Formula 3-1(53)
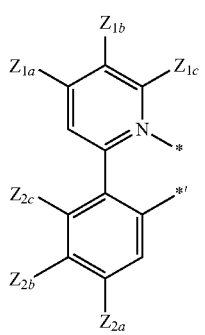
Formula 3-1(54)
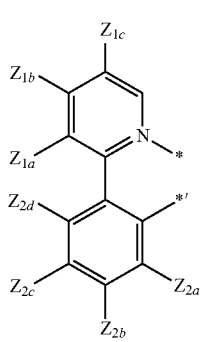
Formula 3-1(55)
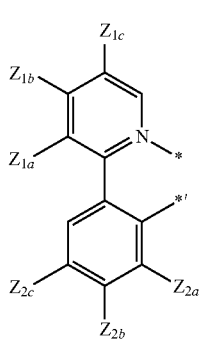
Formula 3-1(56)
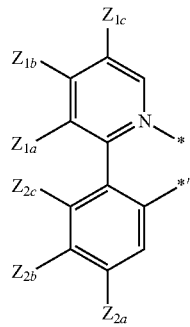
Formula 3-1(57)
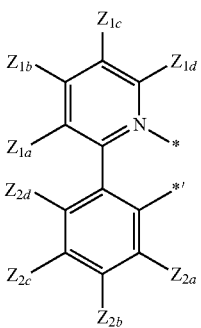
Formula 3-1(58)
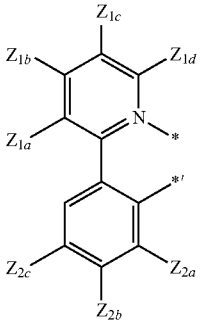
Formula 3-1(59)
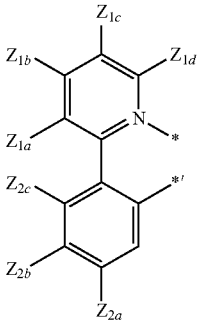
Formula 3-1(60)
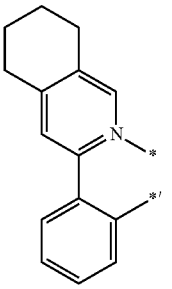

Formula 3-1(61) 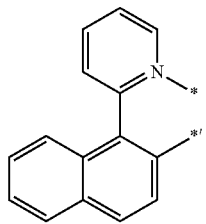

Formula 3-1(62) 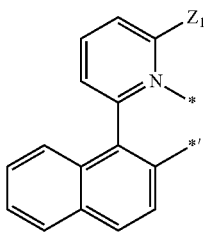

Formula 3-1(63) 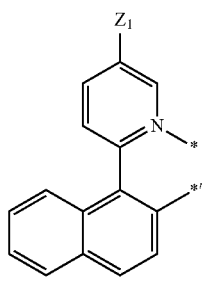

Formula 3-1(64) 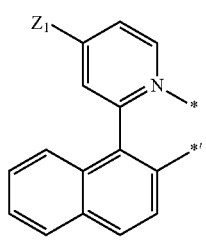

Formula 3-1(65) 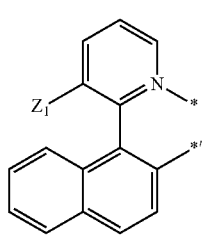

Formula 3-1(66) 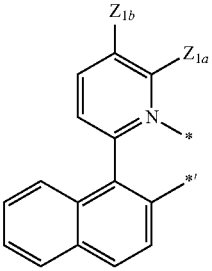

Formula 3-1(67) 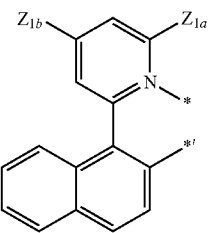

Formula 3-1(68) 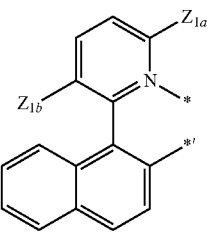

Formula 3-1(69) 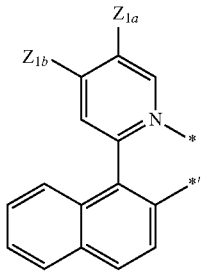

Formula 3-1(70) 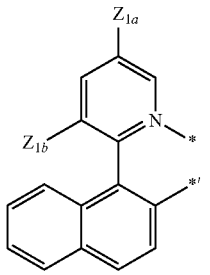

wherein in Formulae 3-1(1) to 3-1(70),

* and *' each indicates a binding site to M of Formula 1, $Z_1$, $Z_2$, $Z_{1a}$, $Z_{1b}$, $Z_{1c}$, $Z_{1d}$, $Z_{2a}$, $Z_{2b}$, $Z_{2c}$, and $Z_{2d}$ are each independently selected from a deuterium, —F, a cyano group, a nitro group, —$SF_5$, —$CH_3$, —$CD_3$, —$CD_2H$, —$CDH_2$, —$CF_3$, —$CF_2H$, —$CFH_2$, —$Si(Q_3)(Q_4)(Q_5)$, groups represented by Formulae 9-1 to 9-17, and groups represented by Formulae 10-7 to 10-30, wherein $Q_3$ to $Q_5$ are each independently selected from —$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, and —$CD_2CDH_2$;

an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group; and an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group, each substituted with at least one of a deuterium and a $C_1$-$C_{10}$ alkyl group:

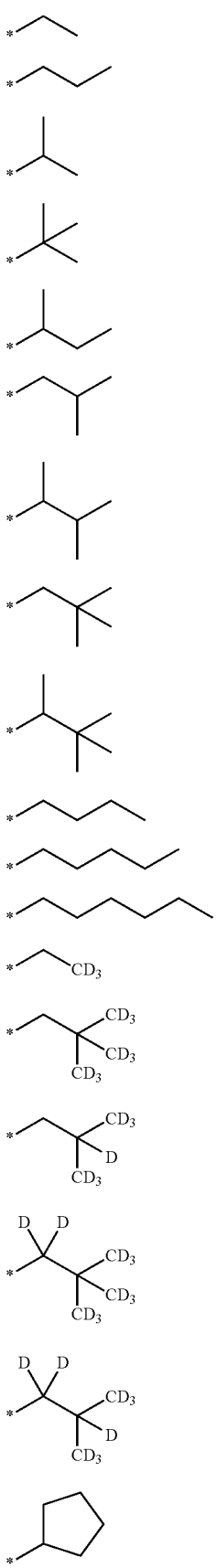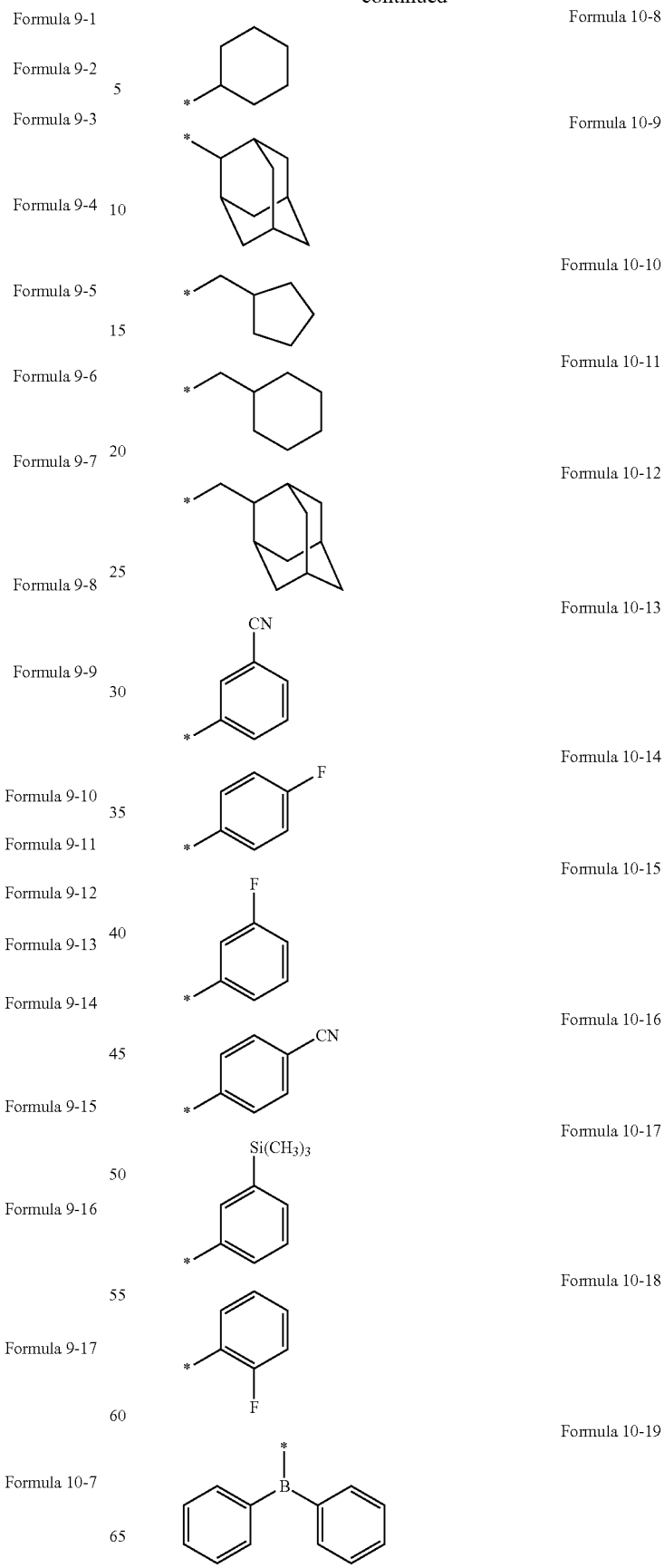

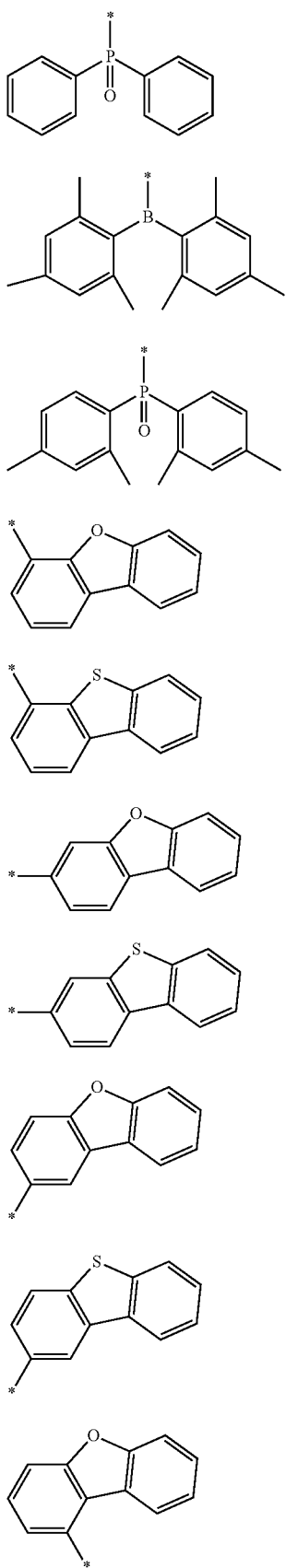
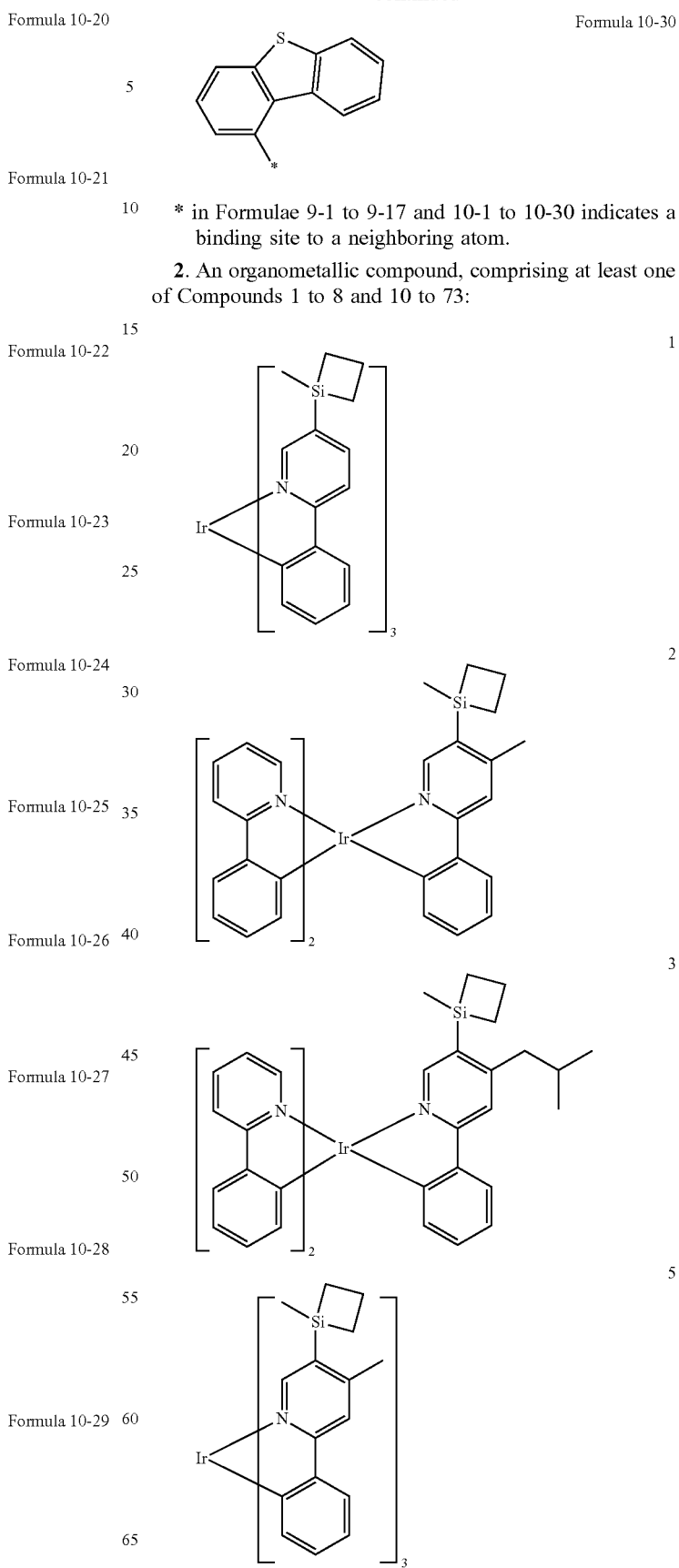
* in Formulae 9-1 to 9-17 and 10-1 to 10-30 indicates a binding site to a neighboring atom.
2. An organometallic compound, comprising at least one of Compounds 1 to 8 and 10 to 73:

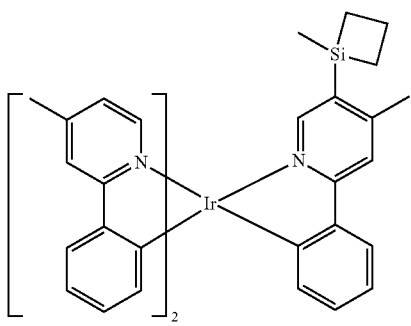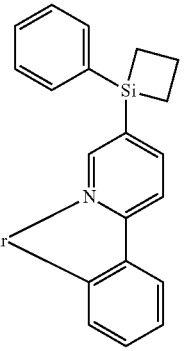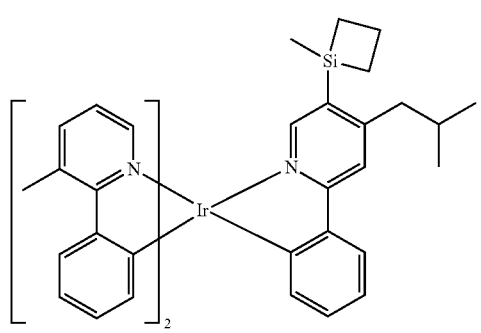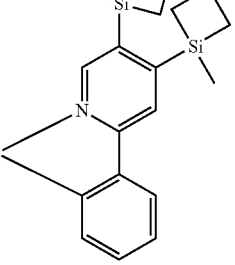

18
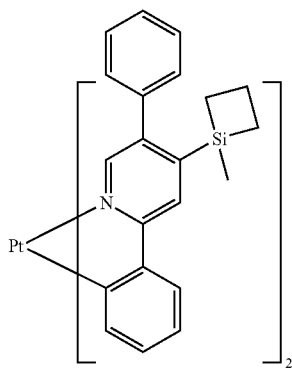
19
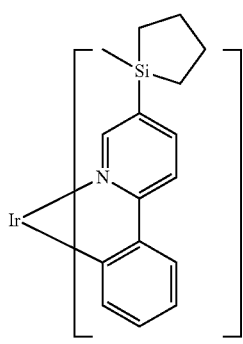
20
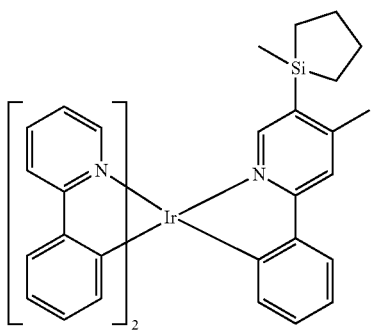
21
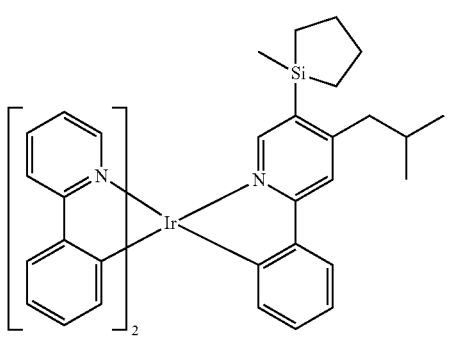
23
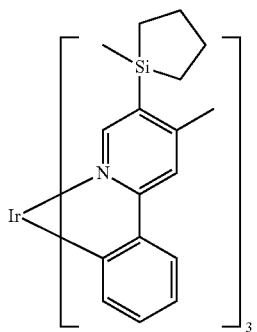
24
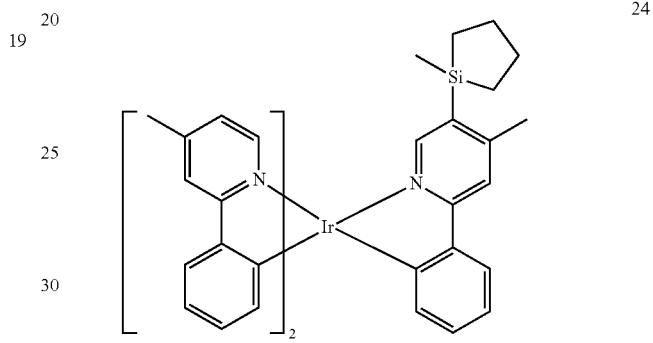
25
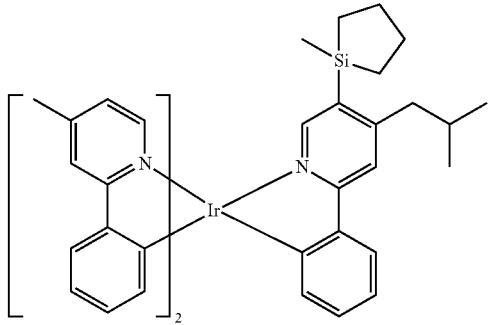
30
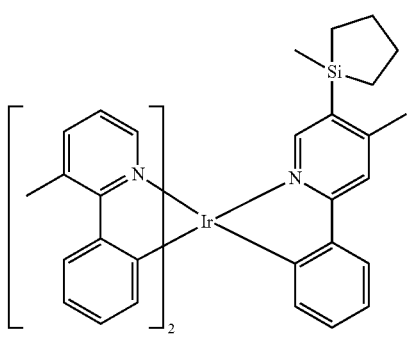

31
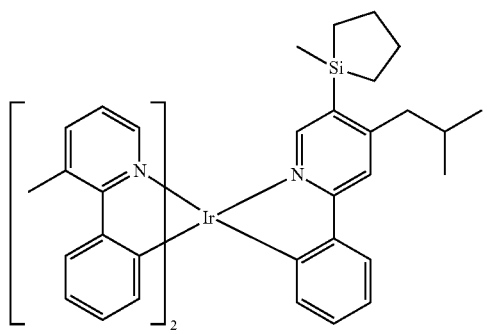
32
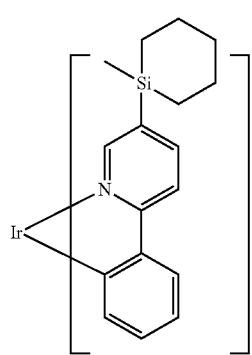
33
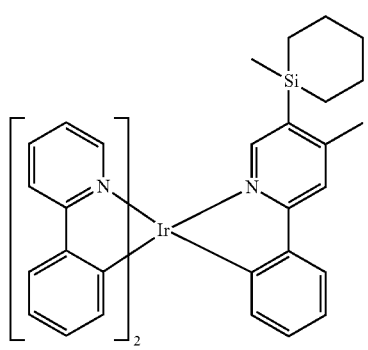
34
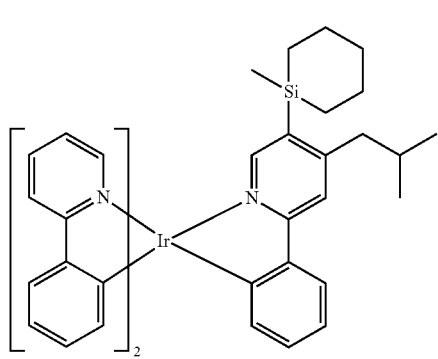
36
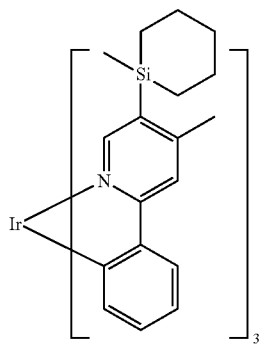
37
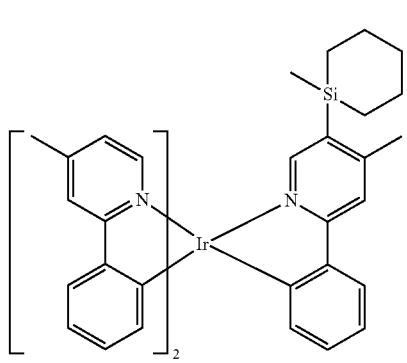
38
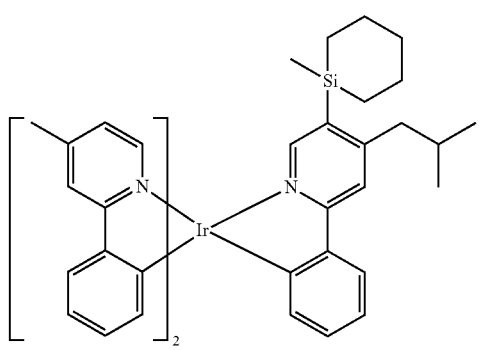
43
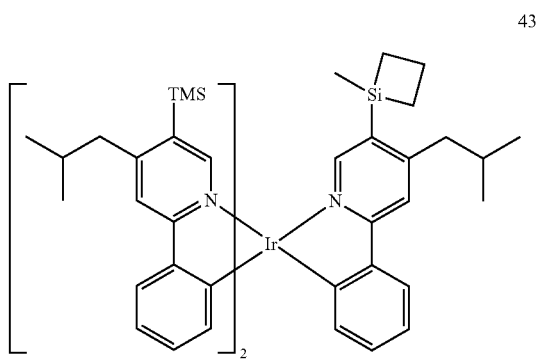

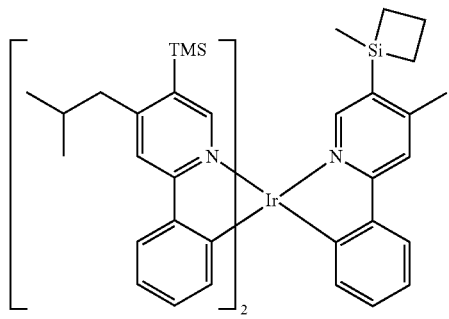
45
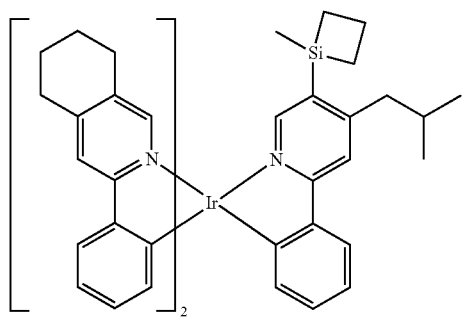
49
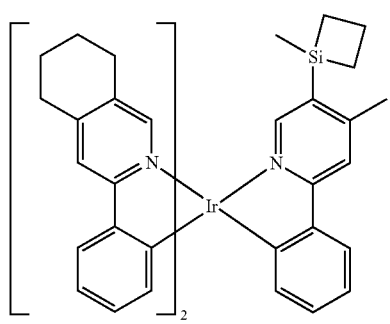
51
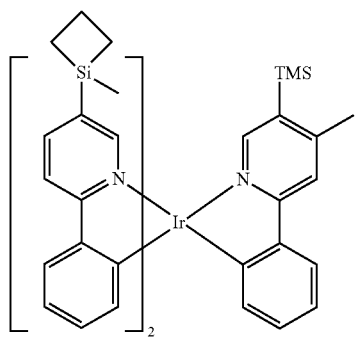
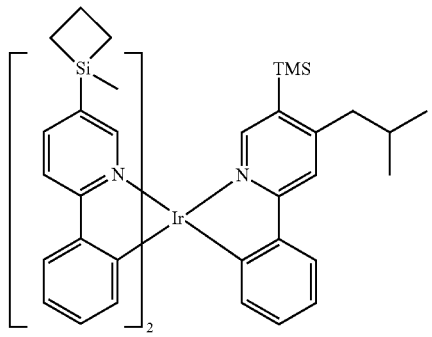
58
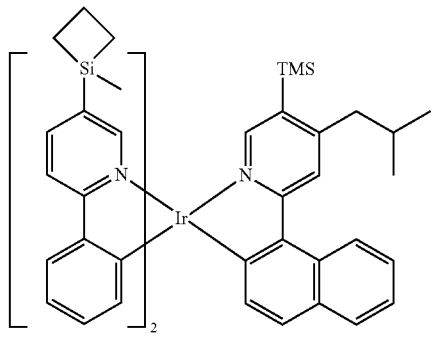
60
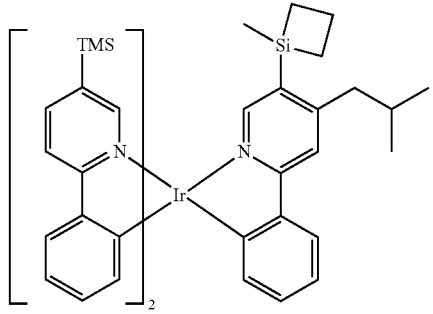
61
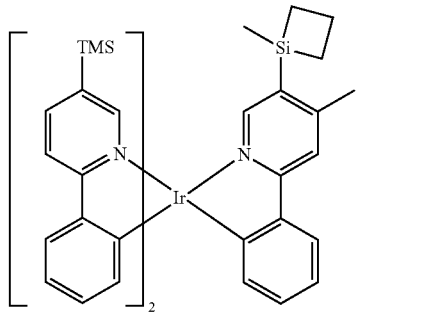
63
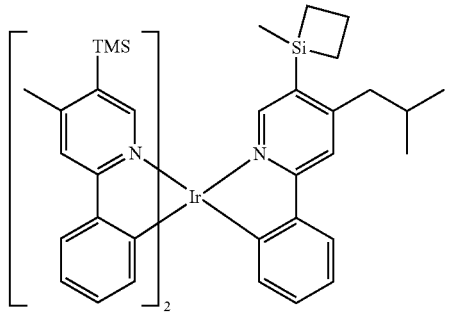
64

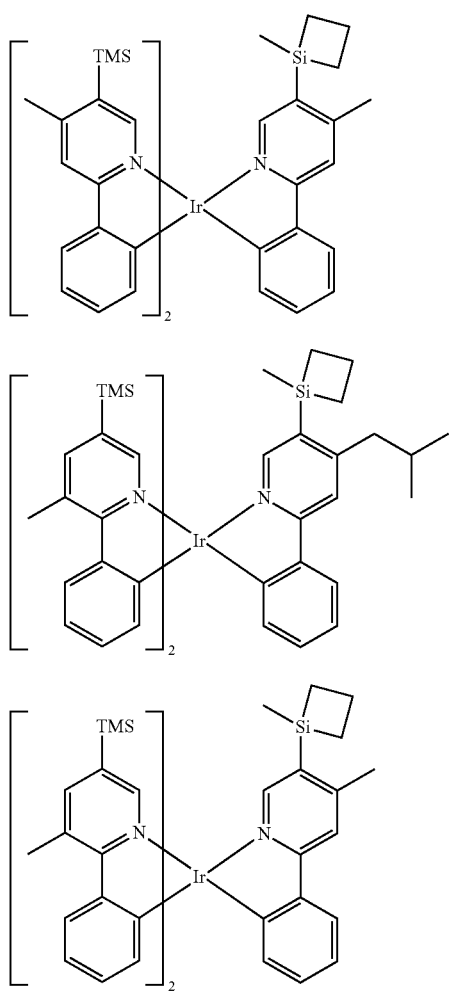

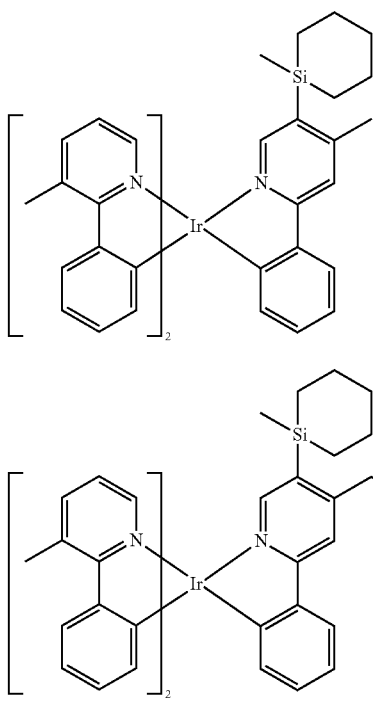

3. An organic light-emitting device comprising:
a first electrode;
a second electrode; and
an organic layer disposed between the first electrode and the second electrode, wherein the organic layer comprises an emission layer and at least one organometallic compound of claim 1.

4. The organic light-emitting device of claim 3, wherein the emission layer comprises the organometallic compound.

* * * * *